(12) United States Patent
Liang et al.

(10) Patent No.: US 11,732,138 B2
(45) Date of Patent: Aug. 22, 2023

(54) DEEP ULTRAVIOLET-EXCITABLE WATER-SOLVATED POLYMERIC DYES

(71) Applicant: BECTON, DICKINSON AND COMPANY, Franklin Lakes, NJ (US)

(72) Inventors: Yongchao Liang, Irvine, CA (US); Jonathan Hollinger, Poway, CA (US); Brian Wall, Poway, CA (US); David Moureau, San Diego, CA (US); Lucy Zhao, San Diego, CA (US); Glenn P. Bartholomew, Escondido, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 17/955,087

(22) Filed: Sep. 28, 2022

(65) Prior Publication Data

US 2023/0235177 A1     Jul. 27, 2023

Related U.S. Application Data

(63) Continuation of application No. 16/226,381, filed on Dec. 19, 2018, now Pat. No. 11,492,493.
(Continued)

(51) Int. Cl.
*C09B 69/10* (2006.01)
*C08G 61/10* (2006.01)
(Continued)

(52) U.S. Cl.
CPC ............ *C09B 69/109* (2013.01); *C08G 61/10* (2013.01); *C08G 61/12* (2013.01); *C09B 69/00* (2013.01);
(Continued)

(58) Field of Classification Search
CPC ..... C09B 69/109; C09B 69/00; C09B 69/101; C09B 69/102; C08G 61/10; C08G 61/12;
(Continued)

(56) References Cited

U.S. PATENT DOCUMENTS 6,808,542 B2   10/2004  Nguyen
7,144,950 B2   12/2006  Bazan et al.
(Continued)

FOREIGN PATENT DOCUMENTS

WO   WO 2004/001379 A2   12/2003
WO   WO 2004/077014 A2    9/2004
(Continued)

OTHER PUBLICATIONS

Bu et al. "Photochemically colour-tuneable white fluorescence illuminants consisting of conjugated polymer nanospheres", Nat Commun., 2014, vol. 5, No. 3799, pp. 1-8.
(Continued)

*Primary Examiner* — Shane Fang
(74) *Attorney, Agent, or Firm* — Bret E. Field; Bozicevic, Field & Francis LLP

(57) ABSTRACT

Water solvated polymeric dyes having a deep ultraviolet excitation spectrum are provided. The subject polymeric dyes include a light harvesting multichromophore having conjugation-modifying repeat units incorporated into the polymer backbone to provide segments of π-conjugated co-monomers having limited π-conjugation between segments. Polymeric tandem dyes are also provided that further include a signaling chromophore covalently linked to the multichromophore in energy-receiving proximity therewith. Also provided are labelled specific binding members that include the subject water solvated polymeric dyes. Methods of evaluating a sample for the presence of a target analyte and methods of labelling a target molecule in which the
(Continued)

subject polymeric dyes find use are also provided. Systems and kits for practicing the subject methods are also provided.

19 Claims, 9 Drawing Sheets

Related U.S. Application Data

(60) Provisional application No. 62/610,478, filed on Dec. 26, 2017.

(51) Int. Cl.
    *C08G 61/12*     (2006.01)
    *C09B 69/00*     (2006.01)
    *G01N 33/58*     (2006.01)
    *G01N 33/542*     (2006.01)
    *G01N 33/533*     (2006.01)

(52) U.S. Cl.
    CPC .......... *C09B 69/101* (2013.01); *C09B 69/102* (2013.01); *G01N 33/582* (2013.01); *C08G 2261/135* (2013.01); *C08G 2261/143* (2013.01); *C08G 2261/145* (2013.01); *C08G 2261/1424* (2013.01); *C08G 2261/1452* (2013.01); *C08G 2261/1644* (2013.01); *C08G 2261/312* (2013.01); *C08G 2261/334* (2013.01); *C08G 2261/344* (2013.01); *C08G 2261/522* (2013.01); *C08G 2261/90* (2013.01); *G01N 33/533* (2013.01); *G01N 33/542* (2013.01)

(58) Field of Classification Search
    CPC ...... C08G 2261/135; C08G 2261/1424; C08G 2261/143; C08G 2261/145; C08G 2261/1452; C08G 2261/1644; C08G 2261/312; C08G 2261/344; C08G 2261/522; C08G 2261/90; G01N 33/582; G01N 33/533; G01N 33/542
    See application file for complete search history.

(56) References Cited

U.S. PATENT DOCUMENTS

| | | |
|---|---|---|
| 7,153,358 B2 | 12/2006 | Weber et al. |
| 7,214,489 B2 | 5/2007 | Bazan et al. |
| 7,241,513 B2 | 7/2007 | Suzuki et al. |
| 7,270,956 B2 | 9/2007 | Bazan et al. |
| 7,318,964 B2 | 1/2008 | Cho et al. |
| 7,629,448 B2 | 12/2009 | Bazan et al. |
| 7,666,594 B2 | 2/2010 | Bazan et al. |
| 7,691,491 B2 | 4/2010 | Saitoh et al. |
| 7,811,755 B2 | 10/2010 | Bazan et al. |
| 7,897,684 B2 | 3/2011 | Bazan et al. |
| 7,914,984 B2 | 3/2011 | Bazan et al. |
| 8,101,416 B2 | 1/2012 | Bazan et al. |
| 8,110,673 B2 | 2/2012 | Bazan et al. |
| 8,158,444 B2 | 4/2012 | Gaylord et al. |
| 8,227,187 B2 | 7/2012 | Bazan et al. |
| 8,309,672 B2 | 11/2012 | Bazan et al. |
| 8,338,532 B2 | 12/2012 | Bazan et al. |
| 8,354,239 B2 | 1/2013 | Gaylord et al. |
| 8,362,193 B2 | 1/2013 | Gaylord et al. |
| 8,383,762 B2 | 2/2013 | Beaujuge et al. |
| 8,455,613 B2 | 6/2013 | Gaylord et al. |
| 8,546,081 B2 | 10/2013 | Bazan et al. |
| 8,575,303 B2 | 11/2013 | Gaylord et al. |
| 8,617,814 B2 | 12/2013 | Bazan et al. |
| 8,669,055 B2 | 3/2014 | Bazan et al. |
| 8,759,444 B2 | 6/2014 | Bazan et al. |
| 8,802,450 B2 | 8/2014 | Gaylord et al. |
| 8,822,633 B2 | 9/2014 | Marrocco et al. |
| 8,835,113 B2 | 9/2014 | Bazan et al. |
| 8,841,072 B2 | 9/2014 | Bazan et al. |
| 8,969,509 B2 | 3/2015 | Liu et al. |
| 8,993,335 B2 | 3/2015 | Bazan et al. |
| 9,085,799 B2 | 7/2015 | Bazan et al. |
| 9,139,869 B2 | 9/2015 | Gaylord et al. |
| 9,159,465 B2 | 10/2015 | Bazan et al. |
| 9,371,559 B2 | 6/2016 | Bazan et al. |
| 9,383,353 B2 | 7/2016 | Gaylord et al. |
| 9,547,008 B2 | 1/2017 | Gaylord et al. |
| 9,691,990 B2 | 6/2017 | Mun et al. |
| 9,719,998 B2 | 8/2017 | Liang et al. |
| 9,722,252 B2 | 8/2017 | Liu et al. |
| 9,758,625 B2 | 9/2017 | Bartholomew |
| 10,228,375 B2 | 3/2019 | Liang et al. |
| 2003/0154647 A1 | 8/2003 | Nguyen |
| 2004/0142344 A1 | 7/2004 | Bazan et al. |
| 2005/0031801 A1 | 2/2005 | Shundo et al. |
| 2005/0191229 A1 | 9/2005 | Chiang et al. |
| 2008/0064042 A1 | 3/2008 | Bazan et al. |
| 2008/0293164 A1 | 11/2008 | Gaylord et al. |
| 2009/0214969 A1 | 8/2009 | Coggan et al. |
| 2009/0230362 A1 | 9/2009 | Bazan et al. |
| 2010/0136702 A1 | 6/2010 | Bazan et al. |
| 2011/0177007 A1 | 7/2011 | Rajagopalan |
| 2011/0256549 A1 | 10/2011 | Gaylord et al. |
| 2012/0028828 A1 | 2/2012 | Gaylord et al. |
| 2012/0252986 A1 | 10/2012 | Liu et al. |
| 2013/0190193 A1 | 7/2013 | Bazan et al. |
| 2015/0226746 A1 | 8/2015 | Bazan et al. |
| 2016/0266131 A1 | 9/2016 | Liang et al. |
| 2016/0266132 A1 | 9/2016 | Gaylord et al. |
| 2016/0341720 A1 | 11/2016 | Bazan et al. |
| 2016/0349267 A1 | 12/2016 | Gaylord et al. |
| 2017/0115298 A1 | 4/2017 | Gaylord et al. |
| 2018/0009990 A1 | 1/2018 | Bartholomew |
| 2018/0163054 A1 | 6/2018 | Bartholomew |
| 2019/0144601 A1* | 5/2019 | Easwaran ............ G01N 33/533 252/519.33 |

FOREIGN PATENT DOCUMENTS

| | | |
|---|---|---|
| WO | WO 2004/092324 A2 | 10/2004 |
| WO | WO 2005/086617 A2 | 9/2005 |
| WO | WO 2006/074471 A2 | 7/2006 |
| WO | WO 2006/074482 A2 | 7/2006 |
| WO | WO 2006/083932 A2 | 8/2006 |
| WO | WO 2008/100344 A2 | 8/2008 |
| WO | WO 2010/151807 A1 | 12/2010 |
| WO | WO 2011/091086 A1 | 7/2011 |
| WO | WO 2016/073052 A1 | 5/2016 |
| WO | WO 2016/144652 A1 | 9/2016 |
| WO | WO 2016/144653 A1 | 9/2016 |
| WO | WO 2017/030450 A1 | 2/2017 |
| WO | WO 2017105927 A1 | 6/2017 |
| WO | WO 2017105928 A1 | 6/2017 |
| WO | WO 2017/180998 A2 | 10/2017 |
| WO | WO 2017172608 A1 | 10/2017 |
| WO | WO 2018/009581 A1 | 1/2018 |
| WO | WO 2018/013389 A1 | 1/2018 |
| WO | WO 2018/111774 A1 | 6/2018 |

OTHER PUBLICATIONS

Feng et al. "Water-soluble fluorescent conjugated polymers and their interactions with biomacromolecules for sensitive biosensors", Chem. Soc. Rev., 2010, 39, 2411-2419.

Gaylord et al. "DNA Hybridization Detection with Water-Soluble Conjugated Polymers and Chromophore-Labeled Single-Stranded DNA", J. Am. Chem. Soc., vol. 125, No. 4, pp. 896-900 (2003).

Gather et al. "An alignable fluorene thienothiophene copolymer with deep-blue electroluminescent emission at 410 nm", Chemical Communications (Cambridge, United Kinadom), 2008 [Upub: Jan. 7, 2008], Vol. 9, pp. 1079-1081.

Liu et al., "Blue-Light-Emitting Fluorene-Based Polymers with Tunable Electronic Properties", Chem. Mater. 2001, 13, pp. 1984-1991.

(56) References Cited

OTHER PUBLICATIONS

Liu et. al. "Optimization of the Molecular Orbital Energies of Conjugated Polymers for Optical Amplification of Fluorescent Sensors", J. Am. Chem. Soc. 2006, 128, pp. 1188-1196.

Liu et al. "Tuning HOMO and LUMO energy levels of blue light-emitting polyfluorene derivatives", Polymeric Materials: Science and Engineering, 2001, vol. 84, pp. 1041-1042.

Marsitzky et al. "Self-Encapsulation of Poly-2,7-fluorenes in a Dendrimer Matrix", Journal of the American Chemical Society (Jul. 25, 2001), 123(29), 6965-6972.

Morales et al. "Amine-Reactive Fluorene Probes: Synthesis, Optical Characterization, Bioconjugation, and Two-Photon Fluorescence Imaging", Bioconjugate Chem., vol. 19, Dec. 17, 2008, pp. 2559-2567.

Morin et al. "Syntheses of Conjugated Polymers Derived from N-Alkyl-2,7-carbazoles", Macromolecules, 2001 [Epub: Jun. 6, 2001], vol. 34, No. 14, pp. 4680-4682.

Pan et al., "Synthesis and properties of fluorenyl-pyridinyl alternatingcopolymers for light-emitting diodes", Polymer International, vol. 63, No. 6, Jun. 2014, pp. 1105-1111.

Ritchie et al., "Effect of meta-linkages on the photoluminescence and electroluminescence properties of light-emitting polyfluorene alternating copolymers", J. Mater. Chem. 2006, 16, pp. 1651-1656.

Traina et al. "Design and Synthesis of Monofunctionalized, Water-Soluble Conjugated Polymers for Biosensing and Imaging Applications", J. Am. Chem. Soc., 2011, 133 (32) 12600-12607.

Wang et al., "Effect of Transannular π-π Interaction on Emission Spectral Shift and Fluorescence Quenching in Dithia[3.3]paracyclophane-Fluorene Copolymers", Macromolecules, 2006, 39, pp. 7277-7285.

Wu et al. "Synthesis and Characterization of Poly(fluorene)-Based Copolymers Containing Various 1,3,4-Oxadiazole Dendritic Pendants", Macromolecules, 2006, 39(13), 4298-4305.

Wu et al. "Synthesis and characterization of new fluorene-acceptor alternating and random copolymers for light-emitting applications", Polymer, 2006 [Epub: Dec. 7, 2005] vol. 47, No. 2 pp. 527-538.

Yang et al., "Enhancement of color purity in blue-emitting fluorene-pyridine-based copolymers by controlling the chain rigidity and effective conjugation length", Polymer, vol. 45 No. 3, Feb. 2004, pp. 865-872.

Zhang et al., "Novel fluorene/trifluoromethylphenylene copolymers: Synthesis, spectra stability and electroluminescence", Dyes and Pigments, vol. 94, No. 3, Sep. 2012, pp. 380-385.

Zhu et al. "Water-Soluble Conjugated Polymers for Imaging, Diagnosis, and Therapy", Chem. Rev. 2012, 112 (8), pp. 4687-4735.

Zalipsky et al. "Functionalized poly(ethylene glycol) for preparation of biologically relevant conjugates," Bioconjugate Chemistry 1995, vol. 6, No. 2, pp. 150-165.

\* cited by examiner

Dye 3

DEEP ULTRAVIOLET-EXCITABLE WATER-SOLVATED POLYMERIC DYES

CROSS-REFERENCE TO RELATED APPLICATIONS

Pursuant to 35 U.S.C. § 119 (e), this application claims priority to the filing date of U.S. Provisional Patent Application Ser. No. 62/610,478, filed Dec. 26, 2017, the disclosure of which application is incorporated herein by reference.

INTRODUCTION

Fluorescent dyes are compounds which, when irradiated with light of a wavelength which they absorb, emit light of a (usually) different wavelength. Fluorescent dyes find use in a variety of applications in biochemistry, biology and medicine, e.g. in diagnostic kits, in microscopy or in drug screening. Fluorescent dyes are characterized by a number of parameters allowing a user to select a suitable dye depending on the desired purpose. Parameters of interest include the excitation wavelength maximum, the emission wavelength maximum, the Stokes shift, the extinction coefficient, the fluorescence quantum yield and the fluorescence lifetime. Dyes may be selected according to the application of interest in order to, e.g., allow penetration of exciting radiation into biological samples, to minimize background fluorescence and/or to achieve a high signal-to-noise ratio.

Molecular recognition involves the specific binding of two molecules. Molecules which have binding specificity for a target biomolecule find use in a variety of research and diagnostic applications, such as the labelling and separation of analytes, flow cytometry, in situ hybridization, enzyme-linked immunosorbent assays (ELISAs), western blot analysis, magnetic cell separations and chromatography. Target biomolecules may be detected by labelling with a fluorescent dye.

SUMMARY

Water solvated polymeric dyes having a deep ultraviolet excitation spectrum are provided. The subject polymeric dyes include a light harvesting multichromophore having conjugation-modifying repeat units incorporated into the polymer backbone to provide segments of π-conjugated co-monomers having limited π-conjugation between segments. Polymeric tandem dyes are also provided that further include a signaling chromophore covalently linked to the multichromophore in energy-receiving proximity therewith. Also provided are labelled specific binding members that include the subject water solvated polymeric dyes. Methods of evaluating a sample for the presence of a target analyte and methods of labelling a target molecule in which the subject polymeric dyes find use are also provided. Systems and kits for practicing the subject methods are also provided.

BRIEF DESCRIPTION OF THE FIGURES

It is understood that the drawings, described below, are for illustration purposes only. The drawings are not intended to limit the scope of the present teachings in any way.

DEFINITIONS

Figure 1:
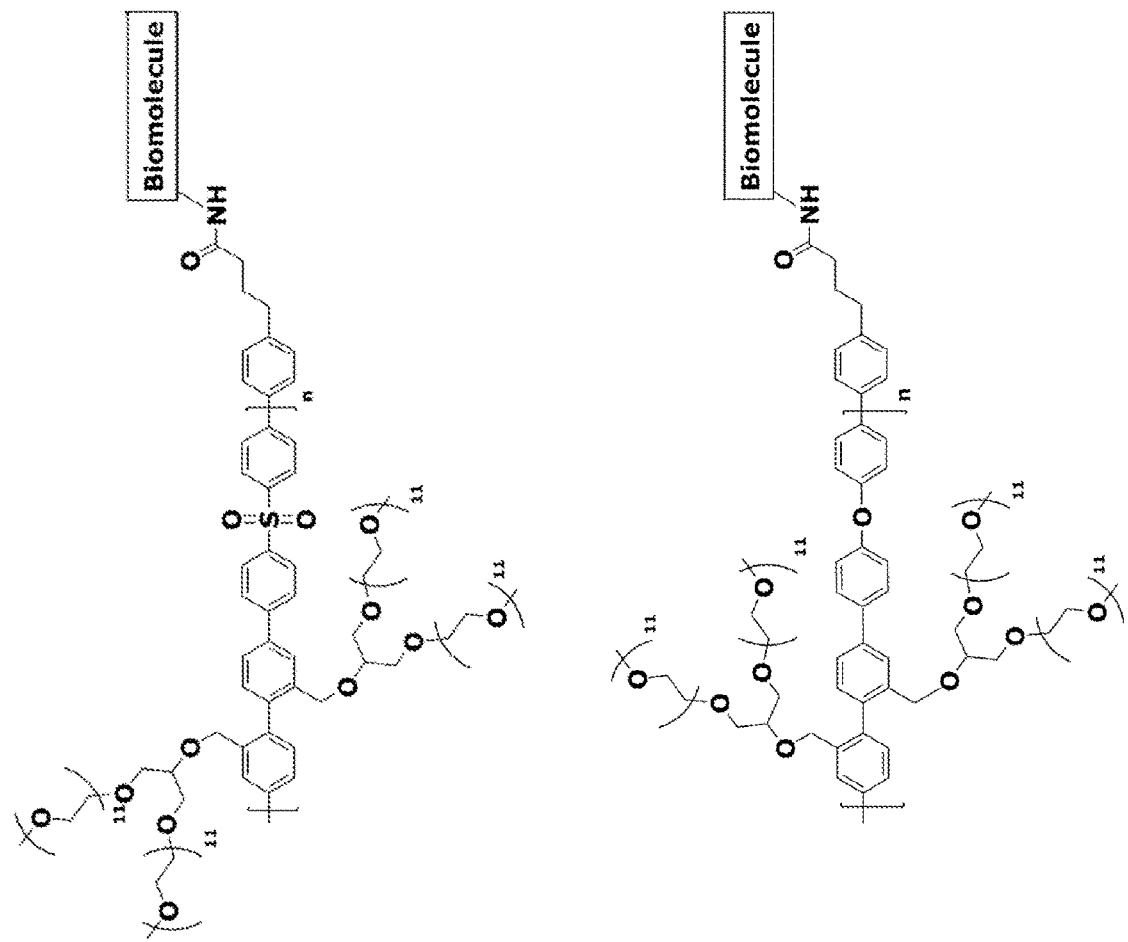
FIG. 1 depicts exemplary co-monomers, conjugation-modifying repeat units and polymeric dyes of the present disclosure.
Figure 2:
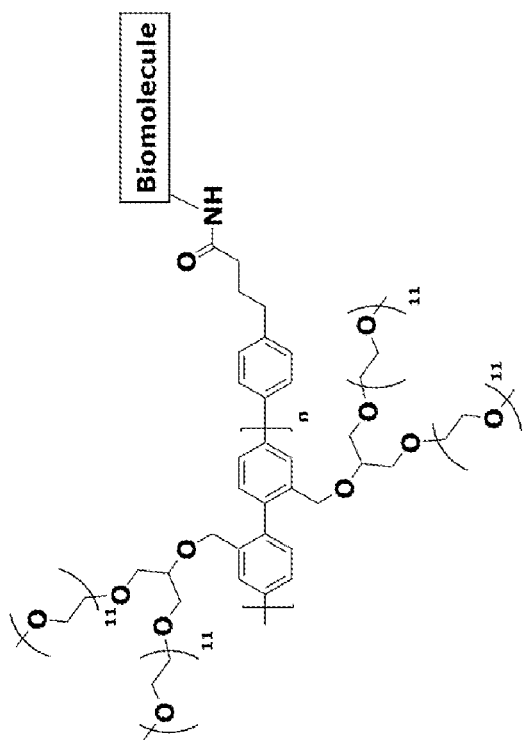
FIG. 2 depicts an exemplary pi-conjugated segment of an exemplary polymeric dye of the present disclosure.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Still, certain terms are defined below for the sake of clarity and ease of reference.

It must be noted that as used herein and in the appended claims, the singular forms "a", "an", and "the" include plural referents unless the context clearly dictates otherwise. For example, the term "a dye" refers to one or more dyes, i.e., a single dye and multiple dyes. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "sample" relates to a material or mixture of materials, in some cases in liquid form, containing one or more analytes of interest. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample". As used herein, the term "a biological sample" refers to a whole organism or a subset of its tissues, cells or component parts (e.g. body fluids, including, but not limited to, blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

As used herein, the terms "support bound" and "linked to a support" are used interchangeably and refer to a moiety (e.g., a specific binding member) that is linked covalently or non-covalently to a support of interest. Covalent linking may involve the chemical reaction of two compatible functional groups (e.g., two chemoselective functional groups, an electrophile and a nucleophile, etc.) to form a covalent bond between the two moieties of interest (e.g. a support and a specific binding member). In some cases, non-covalent linking may involve specific binding between two moieties of interest (e.g., two affinity moieties such as a hapten and an antibody or a biotin moiety and a streptavidin, etc.). In certain cases, non-covalent linking may involve absorption to a substrate.

As used herein, the term "polypeptide" refers to a polymeric form of amino acids of any length, including peptides that range from 2-50 amino acids in length and polypeptides that are greater than 50 amino acids in length. The terms "polypeptide" and "protein" are used interchangeably herein. The term "polypeptide" includes polymers of coded and non-coded amino acids, chemically or biochemically modified or derivatized amino acids, and polypeptides having modified peptide backbones in which the conventional backbone has been replaced with non-naturally occurring or synthetic backbones. A polypeptide may be of any convenient length, e.g., 2 or more amino acids, such as 4 or more amino acids, 10 or more amino acids, 20 or more amino acids, 50 or more amino acids, 100 or more amino acids, 300 or more amino acids, such as up to 500 or 1000 or more amino acids. "Peptides" may be 2 or more amino acids, such as 4 or more amino acids, 10 or more amino acids, 20 or more amino acids, such as up to 50 amino acids. In some embodiments, peptides are between 5 and 30 amino acids in length.

As used herein the term "isolated," refers to an moiety of interest that is at least 60% free, at least 75% free, at least 90% free, at least 95% free, at least 98% free, and even at least 99% free from other components with which the moiety is associated with prior to purification.

A "plurality" contains at least 2 members. In certain cases, a plurality may have 5 or more, such as 10 or more, 100 or more, 1000 or more, 10,000 or more, 100,000 or more, $10^6$ or more, $10^7$ or more, $10^8$ or more or $10^9$ or more members.

Numeric ranges are inclusive of the numbers defining the range.

As used herein, the term "specific binding" refers to the ability of a capture agent (or a first member of a specific binding pair) to preferentially bind to a particular analyte (or a second member of a specific binding pair) that is present, e.g., in a homogeneous mixture of different analytes. In some instances, a specific binding interaction will discriminate between desirable and undesirable analytes in a sample with a specificity of 10-fold or more for a desirable analyte over an undesirable analytes, such as 100-fold or more, or 1000-fold or more. In some cases, the affinity between a capture agent and analyte when they are specifically bound in a capture agent/analyte complex is at least $10^{-8}$ M, at least $10^{-9}$ M, such as up to $10^{-10}$ M.

As used herein, the terms "affinity" and "avidity" have the same meaning and may be used interchangeably herein. "Affinity" refers to the strength of binding, increased binding affinity being correlated with a lower Kd.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

As used herein, the terms "evaluating", "determining," "measuring," and "assessing," and "assaying" are used interchangeably and include both quantitative and qualitative determinations.

The term "separating", as used herein, refers to physical separation of two elements (e.g., by size or affinity, etc.) as well as degradation of one element, leaving the other intact.

As used herein, the term "linker" or "linkage" refers to a linking moiety that connects two groups and has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. In some cases, the linker backbone includes a linking functional group, such as an ether, thioether, amino, amide, sulfonamide, carbamate, thiocarbamate, urea, thiourea, ester, thioester or imine. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the terms "polyethylene oxide", "PEO", "polyethylene glycol" and "PEG" are used interchangeably and refer to a polymeric group including a chain described by the formula —$(CH_2—CH_2—O—)_n$— or a derivative thereof. In some embodiments, "n" is 5000 or less, such as 1000 or less, 500 or less, 200 or less, 100 or less, 50 or less, 40 or less, 30 or less, 20 or less, 15 or less, such as 3 to 15, or 10 to 15. It is understood that the PEG polymeric group may be of any convenient length and may include a variety of terminal groups and/or further substituent groups, including but not limited to, alkyl, aryl, hydroxyl, amino, acyl, acyloxy, and amido terminal and/or substituent groups. PEG groups that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165; and by Zhu et al in "Water-Soluble Conjugated Polymers for Imaging, Diagnosis, and Therapy", Chem. Rev., 2012, 112 (8), pp 4687-4735.

As used herein, the term "alkyl" by itself or as part of another substituent refers to a saturated branched or straight-chain monovalent hydrocarbon radical derived by the removal of one hydrogen atom from a single carbon atom of a parent alkane. Alkyl groups of interest include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group includes from 1 to 20 carbon atoms. In some embodiments, an alkyl group includes from 1 to 10 carbon atoms. In certain embodiments, an alkyl group includes from 1 to 6 carbon atoms, such as from 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Amino" refers to the group —NH$_2$. The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Aryl" by itself or as part of another substituent refers to a monovalent aromatic hydrocarbon radical derived by the removal of one hydrogen atom from a single carbon atom of an aromatic ring system. Aryl groups of interest include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group includes from 6 to 20 carbon atoms. In certain embodiments, an aryl group includes from 6 to 12 carbon atoms. Examples of an aryl group are phenyl and naphthyl.

"Substituted aryl", unless otherwise constrained by the definition for the aryl substituent, refers to an aryl group substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Heteroaryl" by itself or as part of another substituent, refers to a monovalent heteroaromatic radical derived by the removal of one hydrogen atom from a single atom of a heteroaromatic ring system. Heteroaryl groups of interest include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, triazole, benzotriazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$-moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Substituted heteroaryl", unless otherwise constrained by the definition for the substituent, refers to an heteroaryl group substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

The term "alkaryl" or "aralkyl" refers to the groups -alkylene-aryl and substituted alkylene-aryl where alkylene, substituted alkylene and aryl are defined herein.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like. "Substituted alkylene" refers to an alkylene group having from 1 to 3 hydrogens replaced with substituents as described for carbons in the definition of "substituted" below.

"Substituted" refers to a group in which one or more hydrogen atoms are independently replaced with the same or different substituent(s). Substituents of interest include, but are not limited to, alkylenedioxy (such as methylenedioxy), -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —NR$^{62}$C(O)NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —C(O)O$^-$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, where R$^{60}$, R$^{61}$ and R$^{62}$ are as defined above. For example, a substituted group may bear a methylenedioxy substituent or one, two, or three substituents selected from a halogen atom, a (1-4C)alkyl group and a (1-4C)alkoxy group. When the group being substituted is an aryl or heteroaryl group, the substituent(s) (e.g., as described herein) may be referred to as "aryl substituent(s)".

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

Other definitions of terms may appear throughout the specification.

DETAILED DESCRIPTION

As summarized above, water solvated polymeric dyes having a deep ultraviolet excitation spectrum are provided. The subject polymeric dyes include a light harvesting multichromophore having conjugation-modifying repeat units incorporated into the polymer backbone to provide segments of π-conjugated co-monomers having limited π-conjugation between segments. In some cases, the polymeric dye includes a plurality of π-conjugated segments separated by conjugation-modifying repeat units. Polymeric tandem dyes are also provided that further include a signaling chromophore covalently linked to the polymeric dye in energy-receiving proximity therewith. Also provided are labelled specific binding members that include the subject water solvated polymeric dyes. Methods of evaluating a sample for the presence of a target analyte and methods of labelling a target molecule in which the subject polymeric dyes find use are also provided. Systems and kits for practicing the subject methods are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

In further describing the subject invention, water solvated polymeric dyes including light harvesting multichromophores and related polymeric tandem dyes further including a signaling chromophore are described first in greater detail. Next, labelled specific binding members which include the subject polymeric dyes are described. Then, methods of interest in which the subject polymeric dyes find use are reviewed. Systems and kits that may be used in practicing methods of the present disclosure are also described.

Polymeric Dyes

As summarized above, the present disclosure provides water solvated polymeric dyes having a deep ultraviolet excitation spectrum and/or a deep UV absorption maximum. Deep ultraviolet (Deep UV or DUV) is a region of the electromagnetic spectrum from about 200 nm to about 350 nm, such as from 250 nm to 350 nm. Deep UV includes ultraviolet B (UVB) and ultraviolet C (UVC) radiation, where UVB radiation has wavelengths in the range of 290 to 320 nm and UVC radiation has wavelengths in the range of 200 nm to 290 nm.

Figure 7:
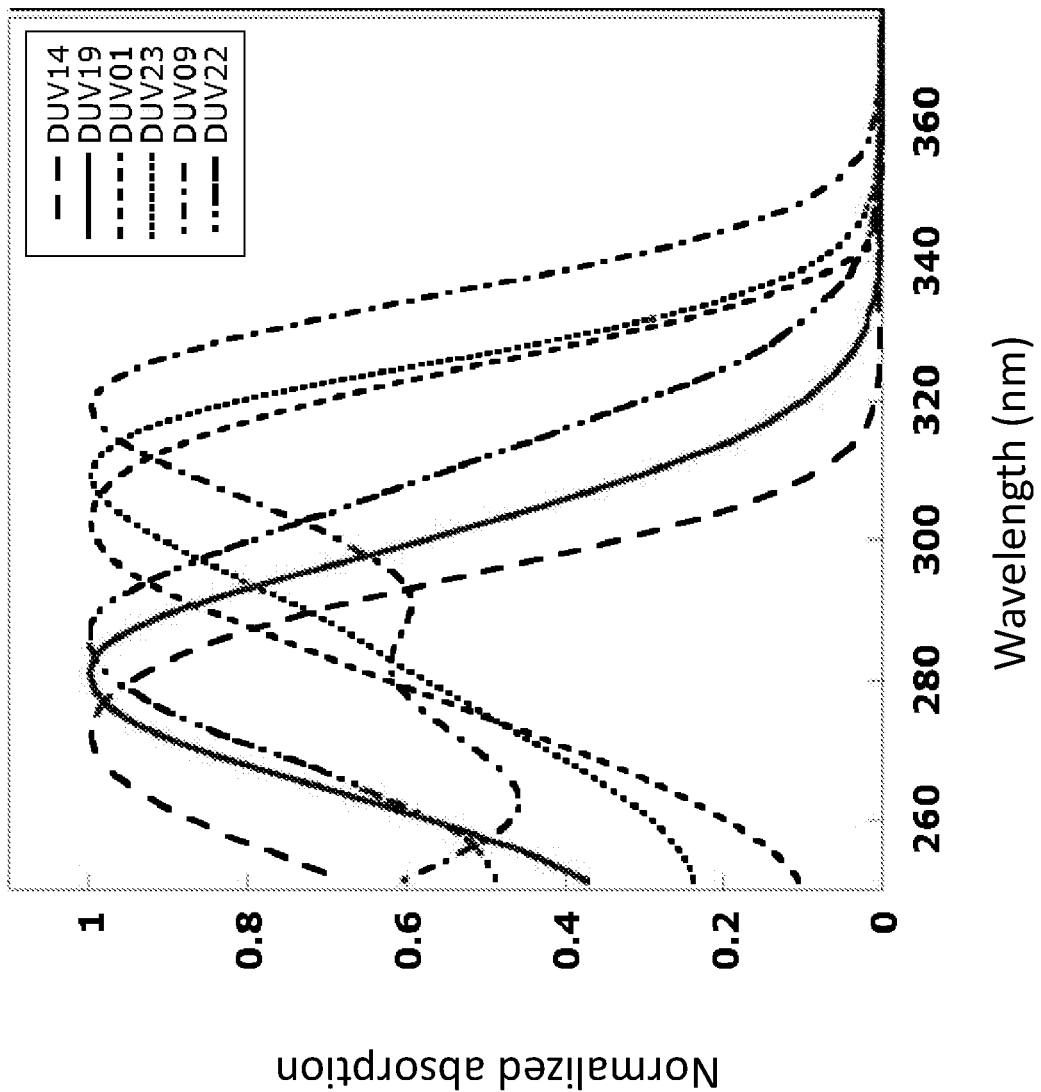
FIG. 7 shows the normalized absorption spectra of several exemplary polymeric dyes having deep ultraviolet excitation spectrum and absorption maxima of 350 nm or less.
Figure 8:
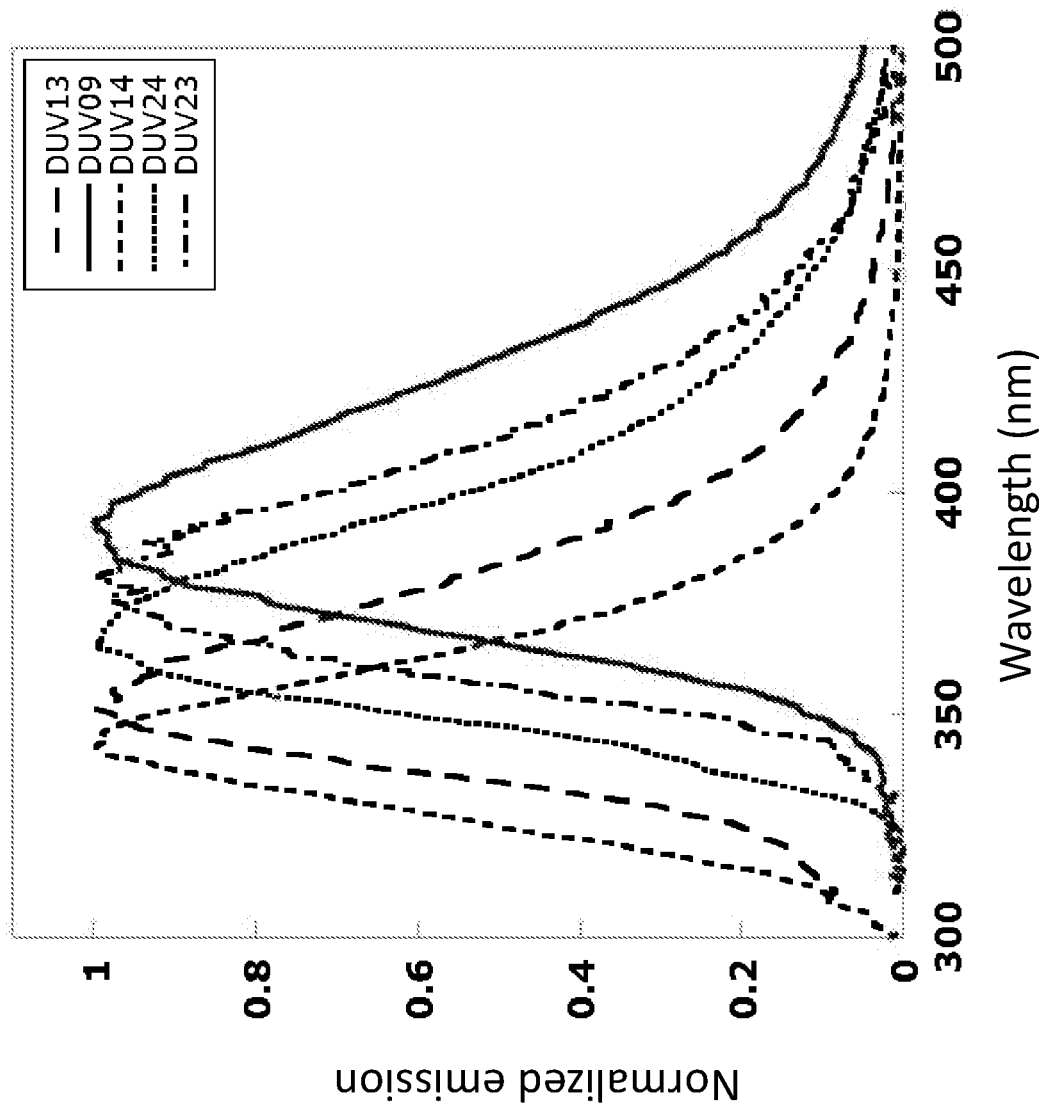
FIG. 8 shows the normalized emission spectra of several exemplary polymeric dyes of the present disclosure.
Figure 9:
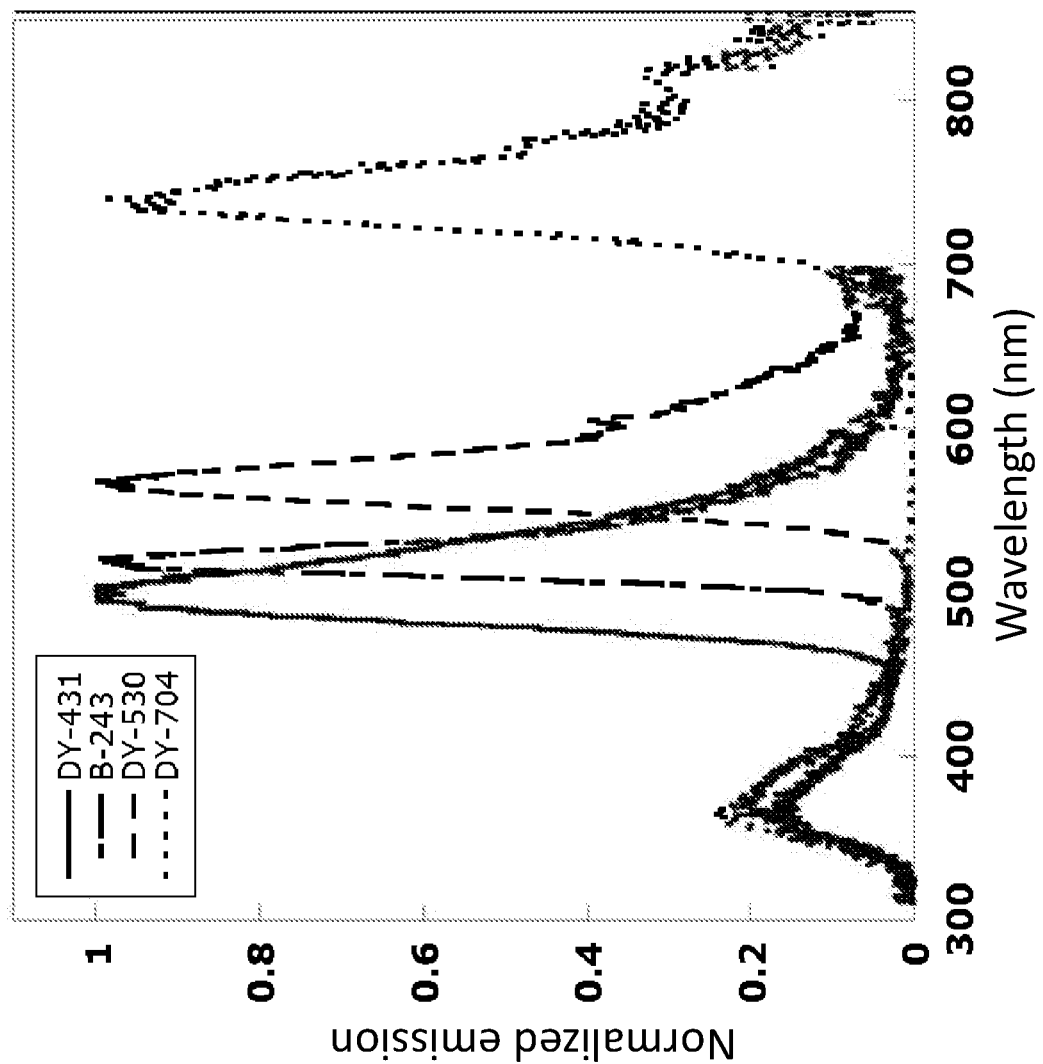
FIG. 9 shows the normalized emission spectra of several exemplary polymeric tandem dyes having the polymeric dye structure of Dye 1 as depicted in FIG. 3 conjugated to various signaling chromophores (linked Dye).

The term "deep ultraviolet excitation spectrum" can refer to the absorption spectrum of a polymeric dye that has a full width at half maximum (FWHM) defining a wavelength range that is inside the deep UV region of the electromagnetic spectrum. As such, the absorption profile of such a polymeric dye is located in the deep UV region. FIG. 7 shows the normalized absorption spectra of several exemplary polymeric dyes having FWHM defining wavelengths in the deep UV. The subject polymeric dyes can absorb strongly at wavelengths in the range from 250 nm to 350 nm.

The term "deep UV absorption maximum" refers to an absorption maximum wavelength of a polymeric dye that is in the deep UV region of the electromagnetic spectrum, e.g., an absorption maximum wavelength of 350 nm or less, such as an absorption maximum wavelength in the range of 200 nm to 350 nm, e.g., 200 to 250 nm, 250 nm to 290 nm, 290 to 320 nm or 320 nm to 350 nm. In some embodiments, a "deep UV absorption maximum" is an absorption maximum wavelength of 340 nm or less, such as 330 nm or less, 320 nm or less, 310 nm or less, 300 nm or less, 290 nm or less, 280 nm or less, 270 nm or less, or even less. FIG. 7 shows the normalized absorption spectra of several exemplary polymeric dyes having deep UV absorption maxima of 350 nm or less and deep ultraviolet excitation spectra have FWHM in the range of 200 nm to 350 nm.

The subject water solvated polymeric dyes find use in a variety of multiplexed applications where a panel of fluorescent dyes can be independently excited to provide emissions for high parameter analyses. The polymeric dyes can be used directly as fluorescent labels or coupled with a small molecule acceptor signaling chromophore in a tandem dye to provide for a variety of emission wavelengths over a range of 320 to 1200 nm. In multi-color applications, use multiple excitation sources can achieving multiplicity and a high number of parameters. In addition to narrow peak width, minimizing absorption at other common excitation sources is important for higher parameter experiments. The degree of cross-source excitation can be tuned for the subject polymeric dyes by selection of a particular structure, co-monomers, and mixtures of co-blocks.

The subject polymeric dyes include a light harvesting multichromophore having segment(s) of π-conjugated co-monomers and conjugation-modifying repeat unit(s). The light harvesting multichromophore of the subject polymeric dyes can provide a desirable absorption profile in the deep UV range without significant absorption at longer wavelengths. A desired deep UV absorption profile can be accomplished by incorporating conjugation-modifying repeat units in the main chain (or backbone) of a polymeric dye, to connect adjacent pi-conjugated segments via covalent bond (s) which units can prevent or reduce the degree of p-orbital overlap (and thus limit the π-conjugation) across these covalent bond(s). The conjugation-modifying repeat units are capable of modulating (e.g., reducing) the extended pi-conjugation that would otherwise be present along a polymeric dye backbone of conjugated co-monomers lacking such repeat units. Without such conjugation-modifying repeat units, a polymeric dye composed solely of the remaining pi-conjugated co-monomers would have extended electronic delocalization and narrow band gaps. The conjugation-modifying repeat units of the subject polymeric dyes directly connect and modulate conjugation between adjacent segments of pi-conjugated co-monomers to provide a desirable effective conjugation length. By limiting the effective conjugation length of the resulting light harvesting multichromophore, wider electronic band gaps can be achieved to provide an absorption profile including short wavelengths of light in the deep UV range. As such, the subject polymeric dyes expand the spectral space into the deep UV over spectral coverage provided by conventional dyes and instruments.

Conjugation Modifying Repeat Units

As used herein, the term "conjugation modifying repeat unit" refers to a divalent unit of the polymer backbone that is connected to adjacent segments of pi-conjugated co-monomers and which includes, within the unit, linking covalent bond(s) that prevent or reduce p-orbital overlap across the covalent bond(s) thereby limiting electronic delocalization between the two adjacent pi-conjugated segments. In some cases, the linking covalent bonds can be defined by a divalent atom, group or linker that is directly covalently linked to adjacent units of the polymer backbone. In certain cases, the linking covalent bond is defined by a conjugation modifying repeat unit including two unsaturated groups (e.g., aryl, heteroaryl or alkenyl groups) that are separated in the repeat unit by a sterically strained single covalent bond.

The conjugation-modifying repeat unit can limit electron delocalization along the polymer backbone and thus limit the effective conjugation length. In some cases, the conjugation-modifying repeat unit incorporates into the backbone of the polymeric dye, an atom, functional group or linker (Z) that provides saturated or partially saturated covalent bonds which limit or prevent pi-conjugation across those covalent bonds. In certain cases, the conjugation-modifying repeat unit includes a strained single covalent bond (Z) linking two aryl or heteroaryl groups but limiting p-orbital overlap across the bond. The single covalent bond can be strained by torsion created by incorporation of adjacent sterically hindered substituents on the aryl or heteroaryl that twist the two aryl or heteroaryl groups out of planarity.

The subject polymeric dyes can include a plurality of π-conjugated segments of co-monomers connected via conjugation modifying repeat units. The π-conjugated segments can include a single co-monomer, two or more co-monomers or a larger plurality of co-monomers. In some instances, the π-conjugated segments have an effective conjugation length of 30 or less, such as 20 or less, 18 or less, 16 or less, 14 or less, 12 or less, 10 or less, 8 or less, 6 or less, or 5 or less. Any convenient arrangements of π-conjugated segments and conjugation modifying repeat units can be utilized to provide for a desired effective conjugation length. In some cases, the polymeric dye is an alternating co-polymer of particular π-conjugated segments and conjugation modifying repeat units. In certain cases, the polymeric dye is a random co-polymer of co-monomers where the conjugation modifying repeat units are incorporated into the polymer with a frequency or % molarity to give an average π-conjugated segment size that provides a desired effective conjugation length in the polymer.

A conjugation-modifying repeat unit can comprise two aryl or heteroaryl groups covalently linked to each other via a conjugation-modifying atom, group or linker (Z) that prevents or limits conjugation between the two aryl or heteroaryl groups, e.g., a unit of the formula —Ar$^1$—Z—Ar$^2$— wherein Ar$^1$ and Ar$^2$ are the two aryl or heteroaryl groups and Z is the conjugation-modifying atom, group or linker (Z). The two aryl or heteroaryl groups (e.g., Ar$^1$ and Ar$^2$) can be 1,4-linked or 1,3-linked to the polymeric dye backbone, and can be unsubstituted or further substituted, e.g., with a water solubilizing group (e.g., as described herein). The two aryl or heteroaryl groups (e.g., Ar$^1$ and Ar$^2$) can be monocyclic or bicyclic. In some cases, the two aryl or heteroaryl groups (e.g., Ar$^1$ and Ar$^2$) are independently selected from 1,4-phenyl, 1,3-phenyl, 2,5-pyridyl, 2,6-pyridyl and 3,5-pyridyl, optionally further substituted. In certain cases, the conjugation-modifying repeat unit has a formula —Ar¹—Z—Ar²— wherein Ar¹ and Ar² are each independently a 1,4-phenyl or a 2,5-pyridyl, optionally further substituted. In some instances, a conjugation-modifying repeat unit has a structure of formula (XI):

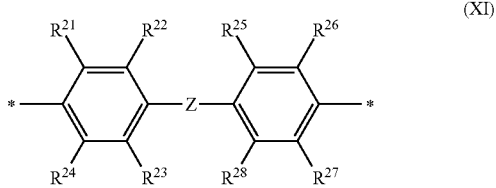

wherein:

Z is selected from a covalent bond, a saturated atom, a saturated group and a functional group, with the proviso that when Z is a covalent bond at least two (e.g., 2, 3 or 4) of $R^{22}$, $R^{23}$, $R^{25}$ and $R^{28}$ are not H;

$R^{21}$-$R^{28}$ are independently selected from H, alkyl, substituted alkyl, aryl, substituted aryl, heteroaryl, substituted heteroaryl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide, and a water solubilizing group, and wherein one or more of $R^{22}$, $R^{23}$, $R^{25}$ and $R^{28}$ is optionally cyclically linked to Z to provide a benzo-fused carbocycle or heterocycle ring; and each * is a site for covalent attachment to the backbone of the polymeric dye. In some instances of formula (XI), when Z is a covalent bond all of $R^{22}$, $R^{23}$, $R^{25}$ and $R^{28}$ are not H, such that there is reduced p-orbital overlap across Z due to steric strain. As such, z can be a sterically strained single covalent bond in a conjugation-modifying repeat unit of formula (XI).

In certain embodiments of formula (XI), Z is selected from a saturated carbon atom, a saturated heteroatom, a functional group and a saturated linker. A saturated carbon atom (Z) of formula (XI) can be covalently bonded to the adjacent phenyl groups via two single saturated covalent bonds, thereby preventing or limiting orbital overlap between the two phenyl rings. In certain instances, Z is $C(R^5)(R^6)$— wherein $R^5$ and $R^6$ are independently H, alkyl or substituted alkyl. Similarly, a saturated heteroatom (Z) of formula (XI) refers to a heteroatom, such as oxygen, sulfur, nitrogen or silicon that is covalently bonded to the adjacent phenyl groups via two single saturated covalent bonds, thereby preventing or limiting orbital overlap between the two phenyl rings. In certain instances, Z is O, S or NR' or —Si($R^5$)($R^6$)— wherein R', $R^5$ and $R^6$ are independently H, alkyl or substituted alkyl. Similarly, a saturated linker can provide a backbone of three or more saturated covalent bonds between the two adjacent phenyl rings of formula (XI). Any convenient linkers can find use in the repeat unit of formula (XI). Linkers of interest that find use as Z in formula (XI) include, but are not limited to, alkyl linkers, such as a $C_2$-$C_{12}$ substituted or unsubstituted alkyl linker or a $C_2$-$C_6$ substituted or unsubstituted alkyl linker, a polyethylene glycol linker (e.g., —O—(CH₂CH₂O)$_n$— where n is 1-6, such as 1, 2, 3, 4, 5 or 6) or a modified polyethylene glycol (PEG) linker (e.g., a substituted PEG, or a terminal modified PEG, e.g., —Z—(CH₂CH₂O)$_n$—).

A functional group (Z) of formula (XI) can refer to a heteroatom-containing group of atoms having characteristic properties, which provides a linkage between the two phenyl groups of formula (XI) but that prevents or limits conjugation between the phenyl groups. Functional groups of interest that find use in conjugation modifying repeat units include, but are not limited to, oxygen, sulfur and/or nitrogen containing functional groups, such as a sulfonyl, a keto, an amide, ester, carbonate, carbamate or urea. Exemplary functional groups include —S(O)—, —SO₂—, —SO₂NR'—, —S(O)O—, —C(O)—, —C(O)NR'—, —C(O)O—, —OC(O)NR'—, —OC(O)O—, —NR'C(O) NR'—, where R' is H, alkyl or substituted alkyl. Exemplary conjugation-modifying repeat units of interest include, but are not limited to:

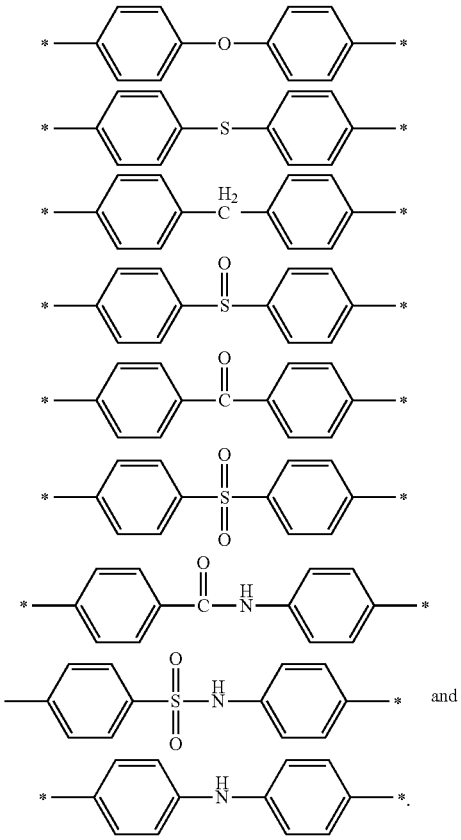

In some embodiments of formula (XI), Z is a covalent bond, at least one of $R^{22}$ and $R^{23}$ is not H and at least one of $R^{25}$ and $R^{28}$ is not H. In some cases, three of $R^{22}$, $R^{23}$, $R^{25}$ and $R^{28}$ are not H. In some instances, all of $R^{22}$, $R^{23}$, $R^{25}$ and $R^{28}$ are not H. In some instances, two or more of $R^{22}$, $R^{23}$, $R^{25}$ and $R^{28}$ are water solubilizing groups. In certain instances, $R^{23}$ and $R^{25}$ are each H. In such cases, the Z bond of the conjugation-modifying repeat unit is torsionally strained by the selection of substituents at $R^{22}$, $R^{23}$, $R^{25}$ and/or $R^{28}$ thereby reduce planarity and orbital overlap between the two adjacent phenyl rings. In such cases, the conjugation-modifying repeat unit can modulate (e.g., limit) electronic delocalization between flanking π-conjugated segments or co-monomers to which the two 1,4-phenyl rings of formula (XI) are conjugated.

In some embodiments of formula (XI), Z is a covalent bond and the conjugation-modifying repeat unit comprises the structure:

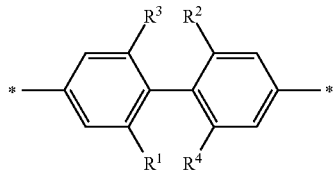

(XIII)

wherein:

R$^1$ to R$^4$ are independently selected from hydrogen, alkyl, substituted alkyl, halogen (e.g., fluoro), cyano,

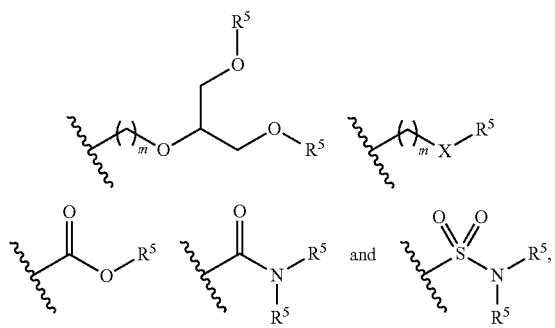

wherein X is O, S, CONH or NH, with the proviso that R$^1$ and R$^2$ are not hydrogen; each R$^5$ is independently —(CH$_2$CH$_2$O)$_p$R' wherein p is an integer from 0 to 50 and R' is H, an alkyl or a substituted alkyl; and m is an integer from 0 to 10. In certain instances of formula (XIII), at least two of R$^1$ to R$^4$ are selected from:

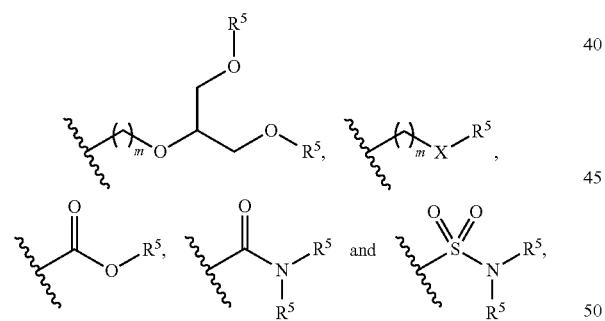

wherein X is O, S, CONH or NH, wherein each R$^5$ is independently —(CH$_2$CH$_2$O)$_p$R' wherein p is an integer from 0 to 50 and R' is H, an alkyl or a substituted alkyl. In certain instances of formula (XIII), R$^1$ and R$^2$ are selected from:

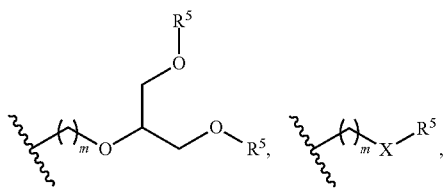

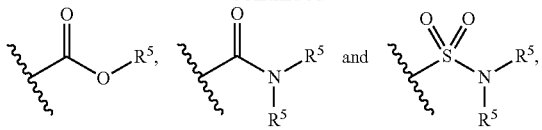

wherein X is O, S, CONH or NH, wherein each R$^5$ is independently —(CH$_2$CH$_2$O)$_p$R' wherein each p is independently an integer from 0 to 50 (such as 6-50, 6-40, 6-30, 8-30, 10-30 or 10-20, e.g., 10, 11, 12, 13, 14, 15, 16, 17, 18, 19 or 20) and R' is H, an alkyl or a substituted alkyl.

Exemplary conjugation-modifying repeat units of interest include, but are not limited to:

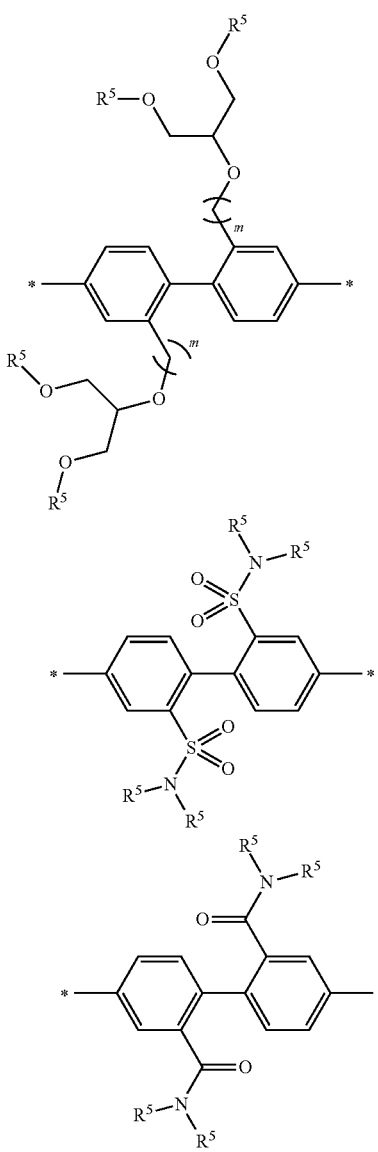

each R$^5$ is independently —(CH$_2$CH$_2$O)$_p$R' wherein p is an integer from 0 to 50 (e.g., 0 to 30, 0 to 20, or 10 to 20) and R' is H, a lower alkyl or a substituted lower alkyl. In certain instances of conjugation-modifying repeat units, in a R$^5$ water soluble polymer, p is 7, 8, 9, 10, 11, 12, 13, 14, 15, 16, 17, 18, 19 or 20; and R' is methyl. In certain cases, each p is 10, 11 or 12.

In some instances of formula (XI), Z is C($R^5$)($R^6$)— wherein $R^5$ and $R^6$ are each cyclically linked to an adjacent phenyl ring of formula (XI), e.g., cyclically linked to the $R^{22}$ or $R^{23}$ position, or cyclically linked to the $R^{25}$ or $R^{28}$ provide a benzo-fused carbocycle or heterocycle ring. In certain instances of formula (XI), Z is —C($R^5$)($R^6$)—, wherein $R^5$ is cyclically linked to $R^{22}$ to provide a partially saturated carbocycle (e.g., 5 or 6 membered carbocycle) that is optionally further substituted, and $R^6$ is cyclically linked to $R^{28}$ provide a partially saturated carbocycle (e.g., 5 or 6 membered carbocycle) that is optionally further substituted. In certain embodiments of formula (XI), the conjugation-modifying repeat unit has a structure of formula (XII):

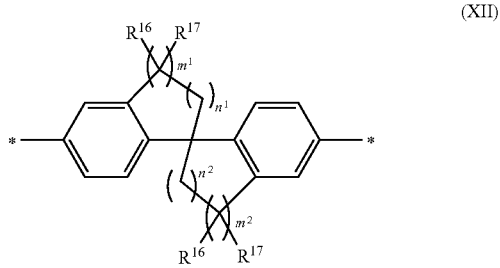

(XII)

wherein:

$n^1$, $n^2$, $m^1$ and $m^2$ are independently 0-3, wherein $n^1+m^1$ and $n^2+m^2$ are each independently 2-3;

$R^{16}$ and $R^{17}$ are each independently selected from H, alkyl, substituted alkyl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide and a water solubilizing group; and each * is a site for covalent attachment to the backbone of the polymeric dye. In certain instances of formula (XII), $n^1+m^1$ and $n^2+m^2$ are each 2. In certain instances of formula (XII), $n^1+m^1$ and $n^2+m^2$ are each 3. In certain instances of formula (XII), each $R^{16}$ and $R^{17}$ are H. In certain instances of formula (XII), $m^2$ and $m^2$ are each 1, and at least one of $R^{16}$ and $R^{17}$ is not H. In certain instances of formula (XII), $m^2$ and $m^2$ are each 1, and at least one or both of $R^{16}$ and $R^{17}$ is a water solubilizing group.

Exemplary conjugation-modifying repeat units of interest include, but are not limited to:

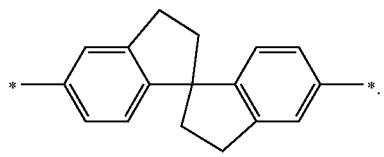

As used herein, the terms "light harvesting multichromophore", "polymeric dye" and "conjugated polymer" are used interchangeably and refer to a conjugated polymer which has a structure capable of harvesting light with a particular absorption maximum wavelength and converting it to emitted light at a longer emission maximum wavelength. In some cases, the light harvesting multichromophore is itself fluorescent. Conjugated polymers (CPs) are characterized by a delocalized electronic structure and may have an effective conjugation length that is substantially shorter than the length of the polymer chain, because the backbone may contain a large number of conjugated segments in close proximity. In some cases, conjugated polymers are efficient for light harvesting and provide for optical amplification via Forster energy transfer to an acceptor.

As used herein the term "unit" refers to a structural subunit of a polymer. The term unit is meant to include monomers, co-monomers, co-blocks, conjugated segments, repeating units, and the like. A "repeating unit" is a subunit of a polymer that is defined by the minimum number of distinct structural features that are required for the unit to be considered monomeric, such that when the unit is repeated n times, the resulting structure describes the polymer or a block thereof. In some cases, the polymer may include two or more different repeating units, e.g., when the polymer is a multiblock polymer or a random arrangement of units, each block may define a distinct repeating unit, e.g., an n-block and a m-block. It is understood that a variety of arrangements of n and/or m repeating units or blocks are possible and that in the depicted formula of the subject multichromophores described herein any convenient linear arrangements of n and m co-blocks of various lengths are included within the structure of the overall polymer. It is understood that the polymer may also be represented by a formula in terms of mol % values of each unit in the polymer and that such formula may represent a variety of arrangements of repeat unit, such as random or multiblock polymer. In some cases, a repeating unit of the polymer includes a single monomer group. In certain instances, a repeating unit of the polymer includes two or more monomer groups, i.e., co-monomer groups, such as two, three, four or more co-monomer groups. As used herein, the term "co-monomer" or "co-monomer group" refers to a structural unit of a polymer that may itself be part of a repeating unit of the polymer. In some embodiments, the conjugated polymer includes a block copolymer that is composed of blocks of polymerized monomers. In such cases, the block copolymer may be described as having distinct repeating units each corresponding to a distinct co-block of the polymer. In some cases, the polymer is a diblock copolymer that contains two different co-blocks. In such cases, the polymer may be described as including co-blocks, where each co-block may be composed of co-monomers, such as one, two, three or more co-monomers.

The multichromophore may have any convenient length. In some cases, the particular number of monomeric repeating units or segments of the multichromophore may fall within the range of 2 to 500,000, such as 2 to 100,000, 2 to 30,000, 2 to 10,000, 2 to 3,000 or 2 to 1,000 units or segments, or such as 5 to 100,000, 10 to 100,000, 100 to 100,000, 200 to 100,000, or 500 to 50,000 units or segments. In some instances, the particular number of monomeric repeating units or segments of the multichromophore may fall within the range of 2 to 1,000, such as 2 to 500, 2 to 100, 3 to 100, 4 to 100, 5 to 100, 6 to 100, 7 to 100, 8 to 100, 9 to 100 or 10 to 100 units or segments.

The multichromophore may be of any convenient molecular weight (MW). In some cases, the MW of the multichromophore may be expressed as an average molecular weight. In some instances, the polymeric dye has an average molecular weight in the range of 500 to 500,000, such as from 1,000 to 100,000, from 2,000 to 100,000, from 10,000 to 100,000 or even an average molecular weight in the range of 50,000 to 100,000.

In some embodiments, the multichromophore includes a particular co-monomer (e.g., an aryl or heteroaryl co-monomer) that constitutes 5% or more by molarity (e.g., 5 mol %)

of the multichromophore, such as 10% or more, 15% or more, 20% or more, 25% or more, 30% or more, 40% or more, 45% or more, 50% or more, 60% or more, 70% or more, or even more by molarity of the multichromophore. In such cases, the multichromophore may include 5 or more repeating units, such as 10 or more, 20 or more, 30 or more, 40 or more, 50 or more, 60 or more, 70 or more, 80 or more, 90 or more, 100 or more, 200 or more, 500 or more, 1000 or more, 10,000 or more, or even more repeating units. In such cases, the multichromophore may include 5 or more co-monomer units, such as 10 or more, 20 or more, 30 or more, 40 or more, 50 or more, 60 or more, 70 or more, 80 or more, 90 or more, 100 or more, 200 or more, 500 or more, 1000 or more, 10,000 or more, or even more co-monomer units. In certain embodiments, a co-monomer (e.g., aryl or heteroaryl co-monomer) of interest constitutes 25% or more by molarity of the multichromophore, such as 30% or more, 40% or more, 45% or more, 50% or more, or even more by molarity of the multichromophore, which includes 5 or more repeating units, such as 10 or more, 20 or more, 30 or more, 40 or more, 50 or more, 60 or more, 70 or more, 80 or more, 90 or more, 100 or more repeating units.

In some embodiments, the multichromophore includes a plurality of first optically active units forming a conjugated system or system of conjugated segments (e.g., as described herein), having an absorption wavelength (e.g., as described herein) at which the first optically active units absorb light to form an excited state. The subject multichromophore may have one or more desirable spectroscopic properties, such as a particular deep UV absorption profile or deep UV maximum wavelength (e.g., as described herein), a particular emission maximum wavelength, extinction coefficient, quantum yield, and the like. The subject polymeric dyes and polymeric tandem dyes provide for a deep UV absorption spectrum and a variety of emission profiles which depend on a variety of factors such as the selected co-monomers, linking groups, substituents and optional linked signaling chromophores of which the polymers are composed.

In some embodiments, the multichromophore itself has an emission maximum wavelength in the range of 300 to 900 nm, such as 300 to 850 nm, 300 to 600 nm, 300 to 500 nm, 300 to 500 nm, 300 to 500 nm, 350 to 500 nm or 400 to 500 nm, where specific examples of emission maxima of interest include, but are not limited to: 340 nm±5 nm, 350 nm±5 nm, 360 nm±5 nm, 370 nm±5 nm, 380 nm±5 nm, 390 nm±5 nm, 400 nm±5 nm, 410 nm±5 nm, 420 nm±5 nm, or 430 nm±5 nm. In certain instances, the multichromophore is linked to an acceptor signaling chromophore, which polymeric tandem dye has an emission maximum wavelength selected from the group consisting of 395 nm±5 nm, 460 nm±5 nm, 490 nm±5 nm, 550 nm±5 nm, 560 nm±5 nm, 605 nm±5 nm, 650 nm±5 nm, 680 nm±5 nm, 700 nm±5 nm and 805 nm±5 nm. In some instances, the polymeric tandem dye has an emission maximum wavelength in the range of 375 to 900 nm (such as in the range of 380 nm to 900 nm, 390 nm to 900 nm, or 400 nm to 900 nm).

In some instances, the multichromophore has an extinction coefficient of $5 \times 10^5$ $cm^{-1}M^{-1}$ or more, such as $6 \times 10^5$ $cm^{-1}M^{-1}$ or more, $7 \times 10^5$ $cm^{-1}M^{-1}$ or more, $8 \times 10^5$ $cm^{-1}M^{-1}$ or more, $9 \times 10^5$ $cm^{-1}M^{-1}$ or more, such as $1 \times 10^6$ $cm^{-1}M^{-1}$ or more, $1.5 \times 10^6$ $cm^{-1}M^{-1}$ or more, $2 \times 10^6$ $cm^{-1}M^{-1}$ or more, $2.5 \times 10^6$ $cm^{-1}M^{-1}$ or more, $3 \times 10^6$ $cm^{-1}M^{-1}$ or more, $4 \times 10^6$ $cm^{-1}M^{-1}$ or more, $5 \times 10^6$ $cm^{-1}M^{-1}$ or more, $6 \times 10^6$ $cm^{-1}M^{-1}$ or more, $7 \times 10^6$ $cm^{-1}M^{-1}$ or more, or $8 \times 10^6$ $cm^{-1}M^{-1}$ or more. In such cases, the multichromophore may have 5 or more repeating units, such as 6 or more, 7 or more, 8 or more, 9 or more, 10 or more, 50 or more, 100 or more, or even more repeating units. In some embodiments, the multichromophore has a molar extinction coefficient of $5 \times 10^5$ $M^{-1}cm^{-1}$ or more. In certain embodiments, the multichromophore has a molar extinction coefficient of $1 \times 10^6$ $M^{-1}cm^{-1}$ or more.

In some instances, the multichromophore has an extinction coefficient of 40,000 $cm^{-1}M^{-1}$ per repeating unit or more, such as 45,000 $cm^{-1}M^{-1}$ per repeating unit or more, 50,000 $cm^{-1}M^{-1}$ per repeating unit or more, 55,000 $cm^{-1}M^{-1}$ per repeating unit or more, 60,000 $cm^{-1}M^{-1}$ per repeating unit or more, 70,000 $cm^{-1}M^{-1}$ per repeating unit or more, 80,000 $cm^{-1}M^{-1}$ per repeating unit or more, 90,000 $cm^{-1}M^{-1}$ per repeating unit or more, 100,000 $cm^{-1}M^{-1}$ per repeating unit or more, or even more. In some instances, the 40,000 $cm^{-1}M^{-1}$ per repeating unit or more described herein is an average extinction coefficient. In certain instances, the repeat unit of the multichromophore may include a single monomer, two co-monomers, or three or more co-monomers. In some instances, the multichromophore has an extinction coefficient of 40,000 $cm^{-1}M^{-1}$ per co-monomer or more, such as 45,000 $cm^{-1}M^{-1}$ per co-monomer or more, 50,000 $cm^{-1}M^{-1}$ per co-monomer or more, 55,000 $cm^{-1}M^{-1}$ per co-monomer or more, 60,000 $cm^{-1}M^{-1}$ per co-monomer or more, 70,000 $cm^{-1}M^{-1}$ per co-monomer or more, 80,000 $cm^{-1}M^{-1}$ per co-monomer or more, 90,000 $cm^{-1}M^{-1}$ per co-monomer or more, 100,000 $cm^{-1}M^{-1}$ per co-monomer or more, or even more. In some instances, the 40,000 $cm^{-1}M^{-1}$ per co-monomer or more is an average extinction coefficient.

π-Conjugated Segments

As summarized above, the subject polymeric dyes include π-conjugated segments whose effective conjugation length are controlled by the incorporation of conjugation-modifying repeat units (e.g., as described herein) into the polymer. The terms "π-conjugated segment" and "segment of π-conjugated co-monomers" are used interchangeably herein and refer to a region of pi-conjugated co-monomers in the polymeric backbone, or on a conjugated branch of the polymeric backbone. The terms "π-conjugated" and "pi-conjugated" are used interchangeably herein. Any convenient arrangements of π-conjugated segments and conjugation modifying repeat units can be utilized to provide for a desired effective conjugation length and resulting spectroscopic properties. It is understood that, in some cases, the subject multichromophores may include co-blocks (e.g., n and m co-blocks) or a random arrangement of repeating units or co-monomers. It is understood that the formula herein depict a representation of the polymeric dye, and that the chemical structure of the polymer may vary in length and/or the particular arrangement of co-monomers, depending on the method of synthesis. The subject multichromophores may include any convenient linear arrangements of n and m co-blocks of various lengths within the structure of the overall polymer. The subject multichromophores may include any convenient linear arrangements of co-monomers of within the structure of the overall polymer, depending on the particular synthesis and polymerization method used. In some cases, the linear arrangements of co-monomers depicted in the structures herein are random. In addition, the multichromophores may include any convenient arrangements of co-monomers within such n and/or m co-blocks, including random, alternating or block arrangements of co-monomers. Unless indicated to the contrary, all possible arrangements of co-monomers are meant to be included in the polymeric dyes described herein. A variety of polymer synthesis methods may be utilized to prepare co-monomers and co-blocks of interest in the preparation of the subject multichromophores. It is understood that in some cases, the polymerization methods may produce a composition including a population of conjugated polymers that includes some variation with respect to the particular length and/or terminal groups (i.e., end groups) present in each conjugated polymer of the population. The formulae depicted herein may refer to a single compound or to a population or sub-population of polymeric compounds. As used herein, * denotes a site for covalent attachment to the unsaturated backbone of a conjugated polymer. It is understood that the formulae depicted herein of the subject polymers is one representation of the structure and that other representations, such as a representation indicating mol % ratios of particular co-monomers in the conjugated polymer may also be used.

The π-conjugated segments of the subject polymeric dye can be composed of any convenient co-monomers capable of pi-conjugation, such as aryl or heteroaryl co-monomers, alkynyl co-monomers (e.g., ethynylene) or segments and alkenyl co-monomers (e.g., vinylene) or segments. Aryl or heteroaryl co-monomers of interest which find use in the π-conjugated segments include, but are not limited to, phenyl co-monomers, biphenyl co-monomers, benzooxazole co-monomers, benzothiazole co-monomers, poly-phenylene co-monomers, and fused tricyclic co-monomers, such as fluorene co-monomers, carbazole co-monomers, silole co-monomers and bridged biphenyl co-monomers. The aryl or heteroaryl co-monomers may be optionally further substituted, e.g., as described herein.

Various co-monomers which find use in π-conjugated segments of the subject polymeric dyes are now described in more detail.

In some embodiments, the polymeric dye comprises a plurality of π-conjugated segments each comprising one or more co-monomers selected from the following structures (a)-(k):

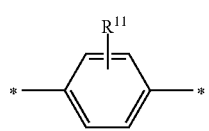
(a)

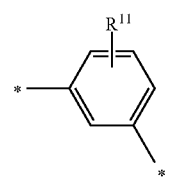
(b)

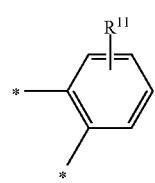
(c)

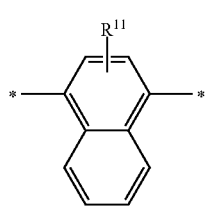
(d)

-continued

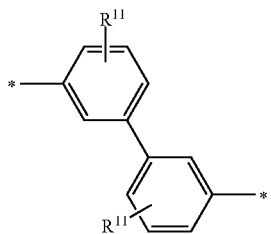
(e)

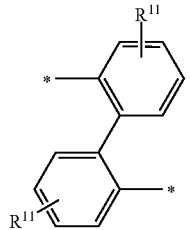
(f)

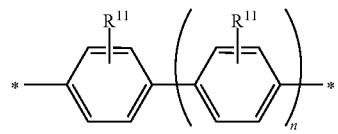
(g)

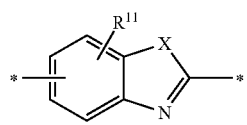
(h)

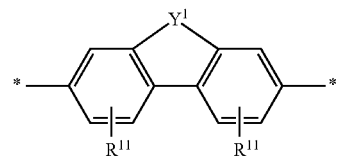
(i)

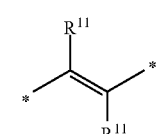
(j)

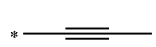
(k)

wherein:

X is O or S;

n is 1-6 (e.g., 1, 2 or 3);

$Y^1$ is selected from $—C(R^{11})_2—$, $—Si(R^{11})_2—$, $—NR^{11}—$, $—C(R^{11})_2C(R^{11})_2—$ and $—C(R^{11})_2C(R^{11})_2—$;

$R^{11}$ is one or more optional substituents each independently selected from hydrogen, aryl, substituted aryl, heteroaryl, substituted heteroaryl, alkyl, substituted alkyl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide and a water solubilizing group; and each * is a site for covalent attachment to the backbone of the polymer.

In certain cases of structures (a)-(k), each $R^{11}$ is independently selected from H, F, methyl, trifluoromethyl, cyano,

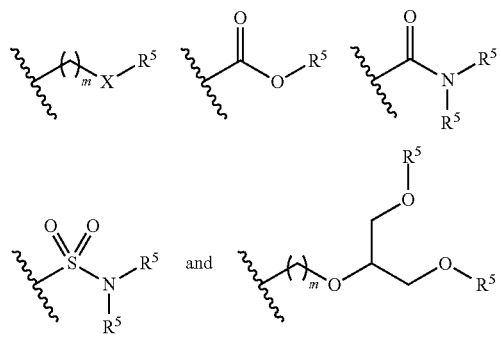

wherein:

X is O or S;

m is an integer from 0-10; and $R^5$ is —$(CH_2CH_2O)_pR'$ wherein R' is H, alkyl or substituted alkyl (e.g., methyl) and p is an integer from 0-40.

In some embodiments, the polymeric dye comprises a plurality of π-conjugated segments each comprising one or more co-monomers selected from alkynyl co-monomers (e.g., ethynylene) and alkenyl co-monomers (e.g., vinylene) of structures (j)-(k):

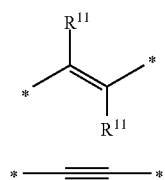

where $R^{11}$ is selected from hydrogen, aryl, substituted aryl, heteroaryl, substituted heteroaryl, alkyl, substituted alkyl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide and a water solubilizing group (e.g., as described herein).

Aryl or Heteroaryl Co-Monomers

As summarized above, the subject polymeric dyes include conjugated segments of aryl or heteroaryl co-monomers linked via covalent bonds, vinylene groups or ethynylene groups. In addition to the co-monomers described in the exemplary formulae above, a variety of aryl and heteroaryl co-monomers find use in the subject polymeric dyes. Any convenient aryl and heteroaryl co-monomers may be utilized in the subject multichromophores, e.g., in a band gap modifying unit, and may be evenly or randomly distributed along the conjugated polymer as described herein.

In some instances, the aryl or heteroaryl co-monomer is a substituted or unsubstituted phenyl, biphenyl or pyridyl co-monomer. In certain embodiments, the aryl or heteroaryl co-monomer is selected from substituted or unsubstituted 1,4-phenyl, a substituted or unsubstituted 1,3-phenyl, a substituted or unsubstituted 4,4'-biphenyl, a substituted or unsubstituted 2,5-pyridyl, and a substituted or unsubstituted 2,6-pyridyl. In certain instances, the co-monomer is an optionally substituted aryl or heteroaryl co-monomer selected from one of the following structures:

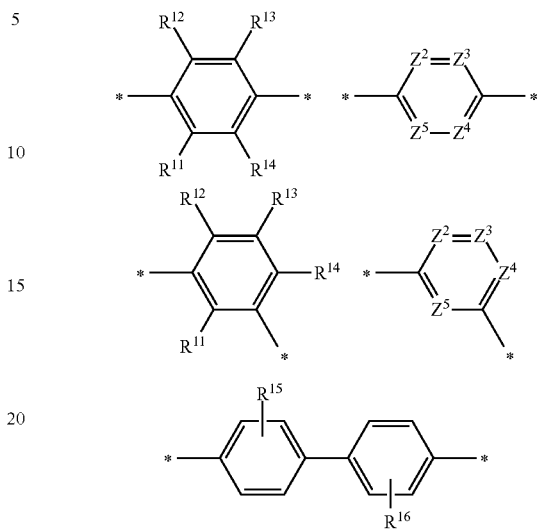

where $Z^2$-$Z^5$ are each independently CR or N, where at least one $Z^2$-$Z^5$ is N; and each R and each $R^{11}$-$R^{16}$ are independently selected from the group consisting of hydrogen, water solubilizing group, halogen, cyano, alkoxy, substituted alkoxy, alkyl and substituted alkyl. In certain embodiments, one and only one of $Z^2$-$Z^5$ is N. In certain embodiments, two and only two of $Z^2$-$Z^5$ is N. In certain instances, $R^{11}$, $R^{12}$ and $R^{14}$ are each H. In some instances, $R^{12}$ and $R^{14}$ are each H. In some instances, $R^{11}$ and $R^{13}$ are each H. In some cases, $R^{15}$ and $R^{16}$ are each H. In some instances, the halogen is fluoro.

In some cases, the aryl or heteroaryl co-monomer (e.g., structure (a)) is selected from one of the following:

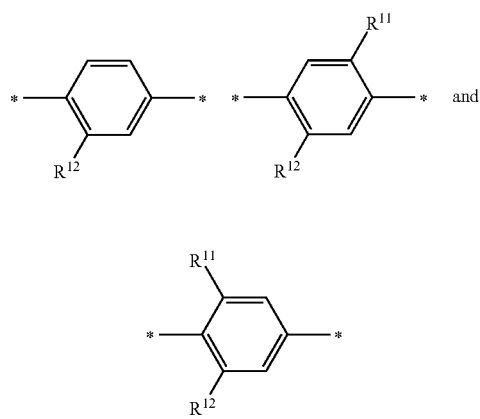

wherein $R^{11}$ and $R^{12}$ are independently hydrogen, aryl, substituted aryl, heteroaryl, substituted heteroaryl, alkyl, substituted alkyl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide and a water solubilizing group. In certain cases, the aryl or heteroaryl co-monomer selected from one of the following:

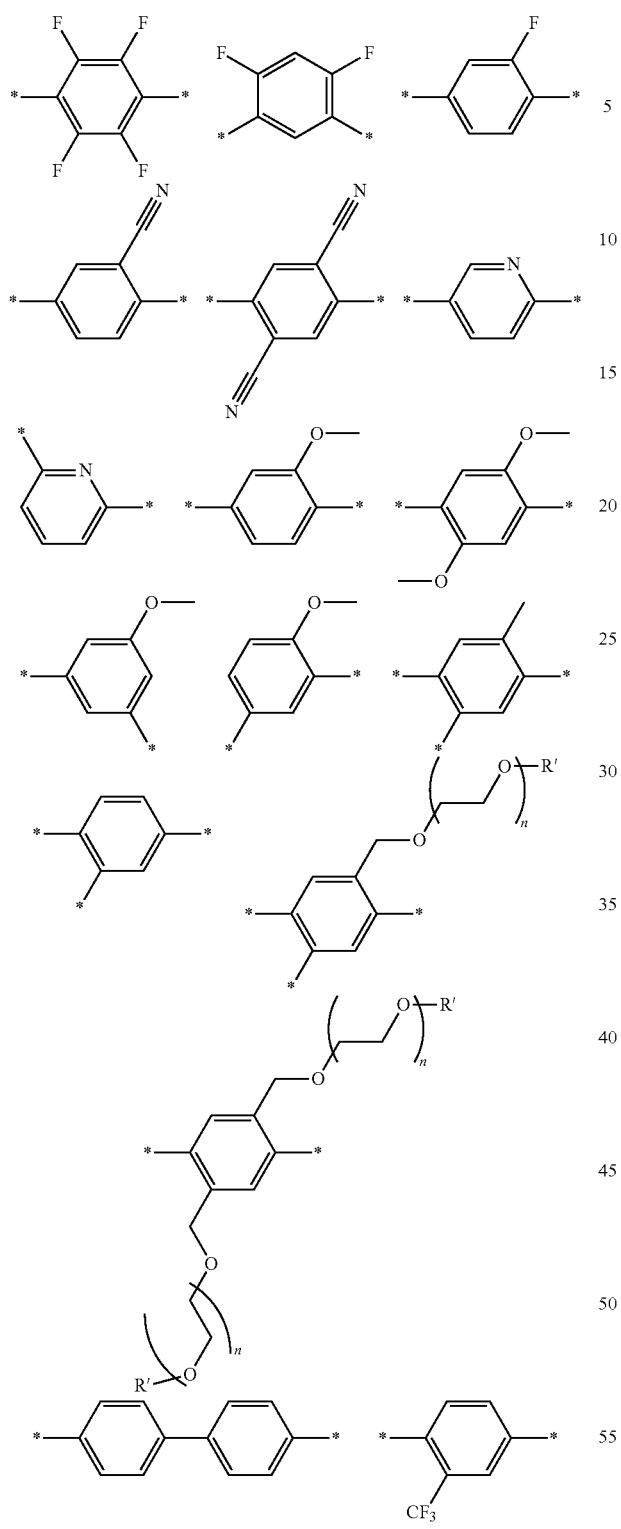

where n is 1-20 and R' is H or lower alkyl. In some embodiments of the aryl or heteroaryl co-monomer structures, n is an integer from 6 to 20, such as 12-20 or 12-16 or 16-20.

Also provided are substituted phenylene co-monomers that are substituted with a further aryl or heteroaryl group which is itself optionally further substituted. The aryl or heteroaryl-substituted phenylene co-monomers can provide for extended pi-conjugation into a sidechain group of the co-monomer. In certain cases, the co-monomer is a heteroaryl-substituted phenylene co-monomer. Selection of particular aryl and heteroaryl substituents that extend as conjugated sidechain groups from the 1,4- or 1,3-phenylene co-monomer can provide for fine-tuning of the spectroscopic properties of the subject deep UV absorbing polymeric dyes. In some embodiments, the substituted phenylene co-monomer is selected from the following structures:

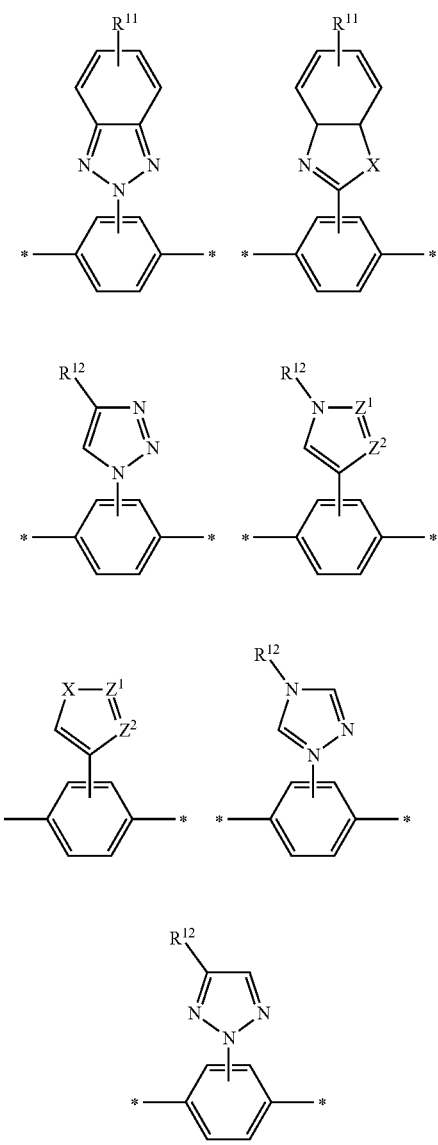

wherein
X is O or S;
$Z^1$ and $Z^2$ are independently selected from $CR^{12}$ and N; and
each $R^{11}$ to $R^{12}$ is independently hydrogen, aryl, substituted aryl, heteroaryl, substituted heteroaryl, alkyl, substituted alkyl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide and a water solubilizing group.

In some cases, the aryl or heteroaryl co-monomer has structure (h):

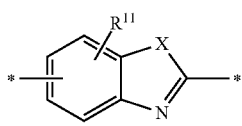

wherein X is O or S; and R[11] is one or more substituents, each independently selected from hydrogen, aryl, substituted aryl, heteroaryl, substituted heteroaryl, alkyl, substituted alkyl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide and a water solubilizing group. In some cases, the aryl or heteroaryl co-monomer of structure (h) is selected from the following co-monomers:

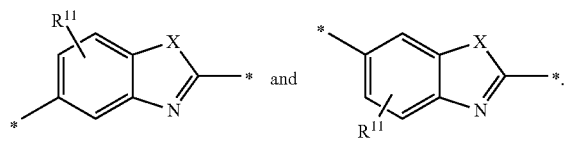

In certain instance, the aryl or heteroaryl co-monomer is a substituted or unsubstituted poly-phenylene co-monomer, e.g., of structure (g) described above. In certain instances, the co-monomer of structure (g) is selected from:

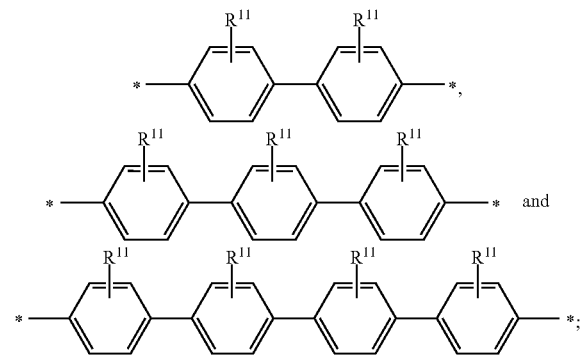

and
wherein R[11] is one or more optional substituents each independently selected from hydrogen, aryl, substituted aryl, heteroaryl, substituted heteroaryl, alkyl, substituted alkyl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide and a water solubilizing group; and each * is a site for covalent attachment to the backbone of the polymer.

In certain instances of the aryl or heteroaryl co-monomers described herein, each R[11] to R[14] is independently selected from H, F, methyl, trifluoromethyl, cyano,

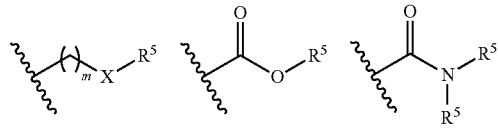

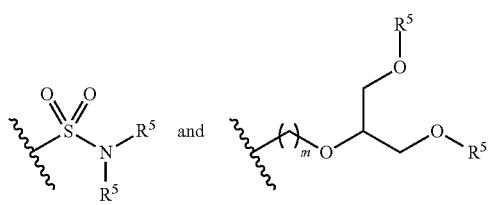

wherein:

X is O or S;

m is an integer from 0-10; and

R[5] is —(CH$_2$CH$_2$O)$_p$R' wherein R' is H, alkyl or substituted alkyl (e.g., methyl) and p is an integer from 0-40.

In some embodiments, the multichromophore includes a substituted aryl or heteroaryl co-monomer described by one of the following structures:

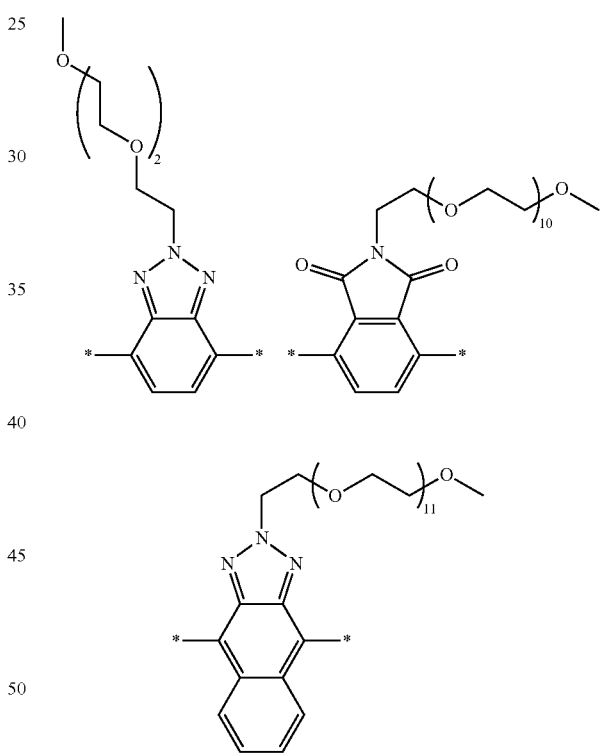

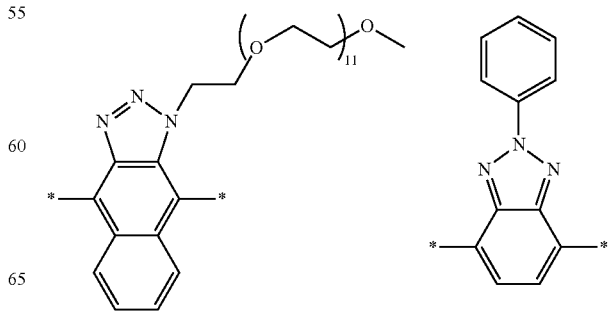

-continued
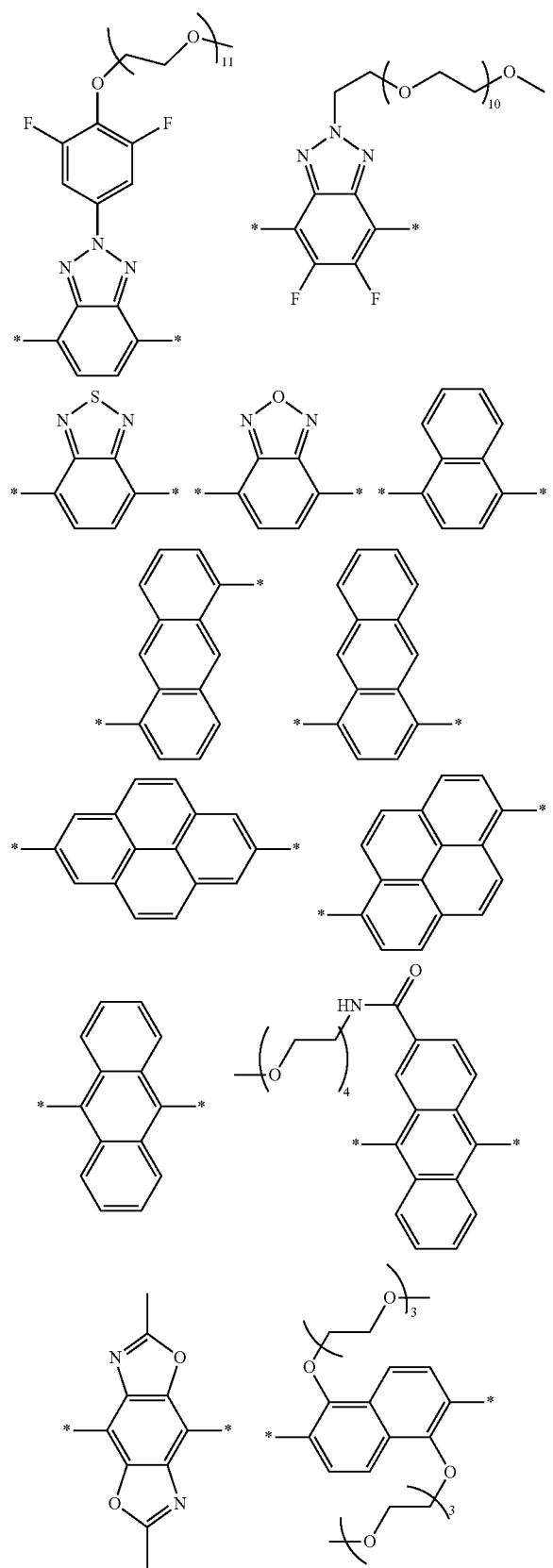
-continued
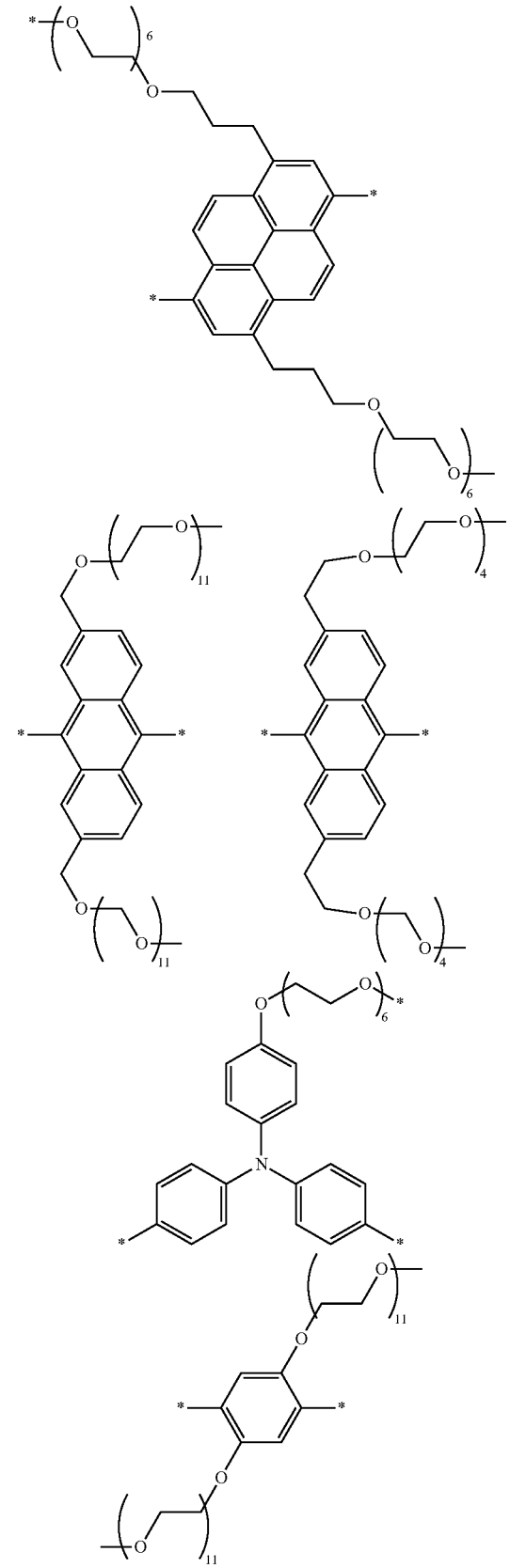

31
-continued
32
-continued
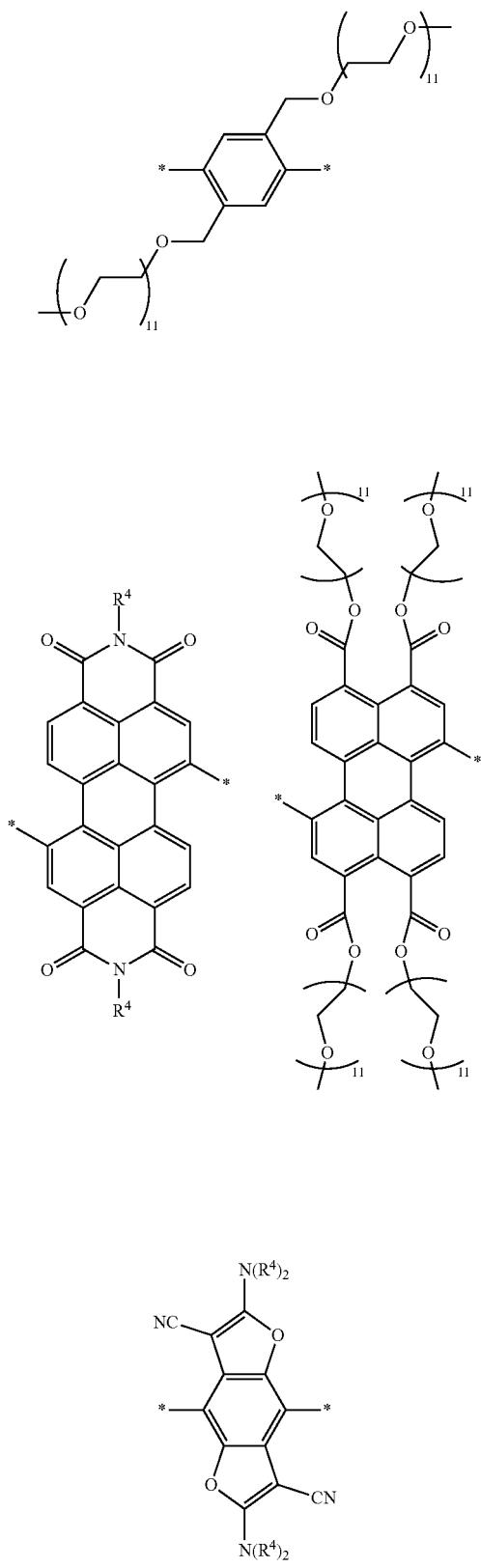
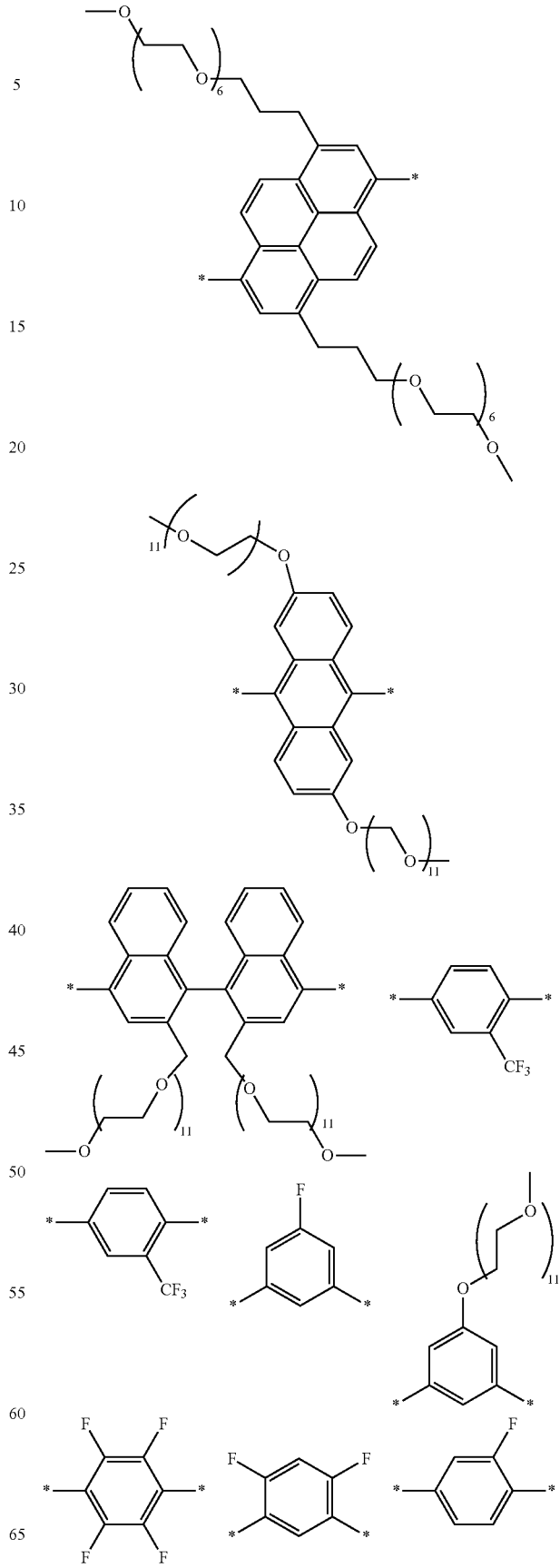

33
-continued
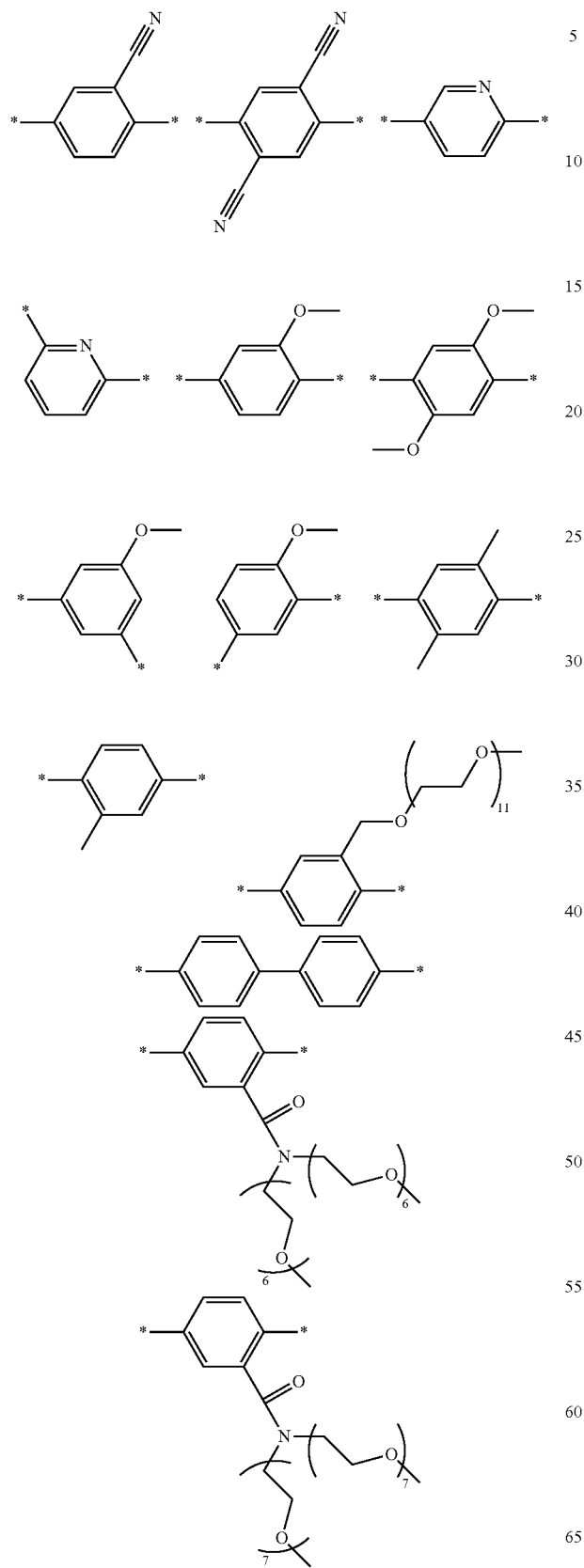
34
-continued
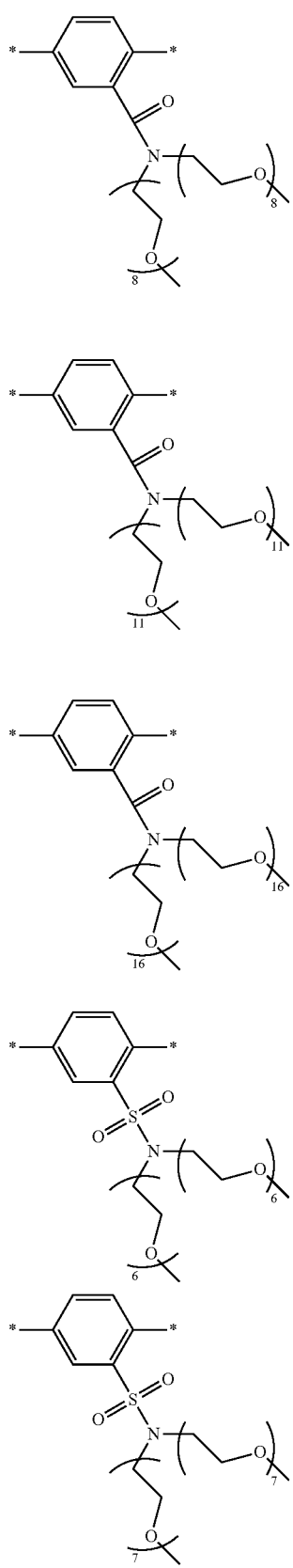

-continued

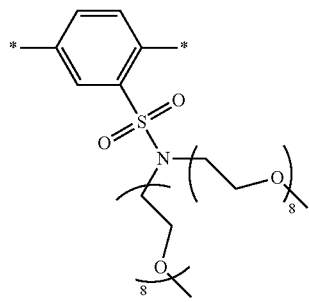

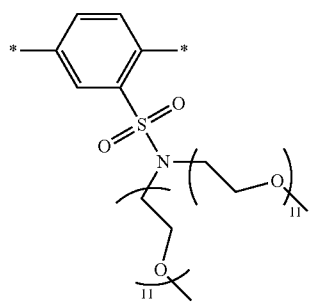

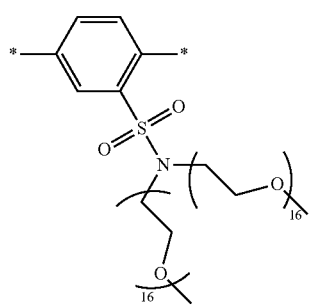

In some embodiments, the multichromophore includes a substituted aryl co-monomer described by the following structure:

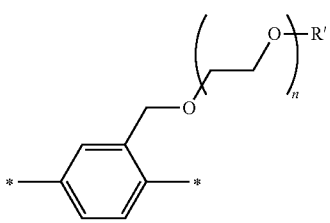

where n is 1-20 and R' is H or lower alkyl. In certain instances, n is 3 to 12. In some embodiments, the multichromophore includes a substituted aryl co-monomer described by the following structure:

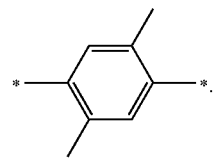

where each n is independently 1-20 and each R' is independently H or lower alkyl. In certain embodiments of the substituted aryl or heteroaryl co-monomer structures shown above, n is 3. In some instances, n is 6, 7, 8, 9, 10, 11, 12, 13, 14, 15, 16, 17, 18, 19 or 20. In certain instances, R' is methyl. In certain instances, R' is hydrogen. In some embodiments, the multichromophore includes a substituted aryl co-monomer described by the following structure:

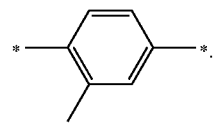

In some embodiments, the multichromophore includes a substituted aryl co-monomer described by the following structure:

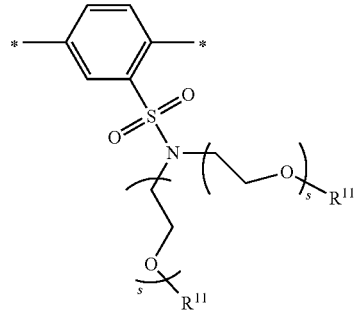

In some embodiments of any of the formula described herein (e.g., formula (I)-(V)), the multichromophore includes a substituted aryl co-monomer (e.g., M1-M3) having on the following structures:

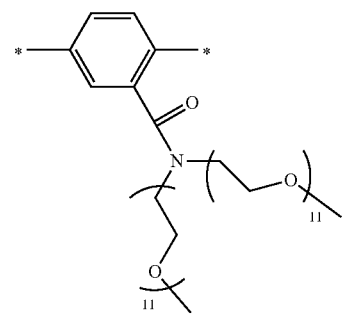
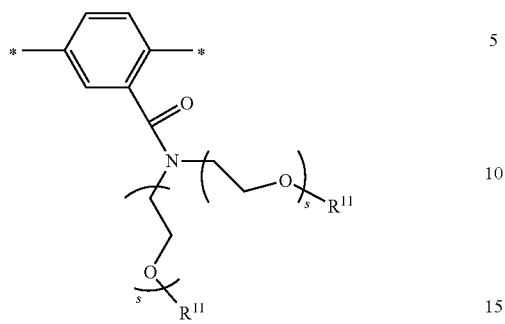
wherein s is 1-50 (e.g., 6-50 6-40, 6-30 or 6-20); and each $R^{11}$ is independently H, alkyl or substituted alkyl. In some embodiments, the multichromophore includes a substituted aryl co-monomer including a branched non-ionic WSG described by one of the following structures:
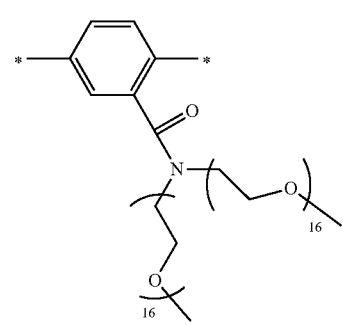
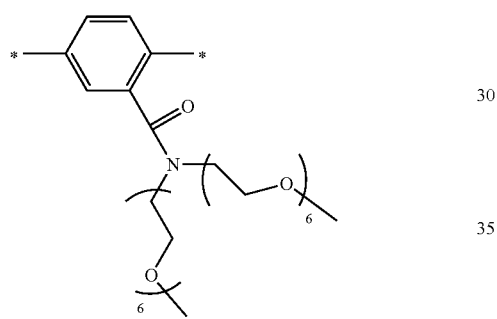
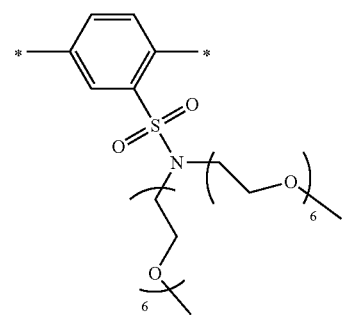
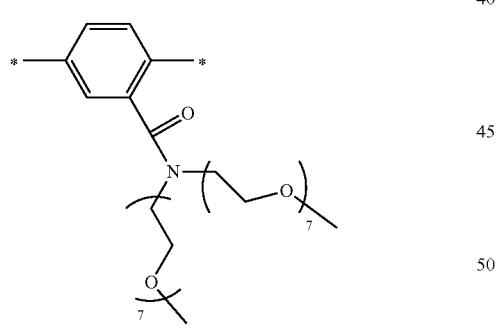
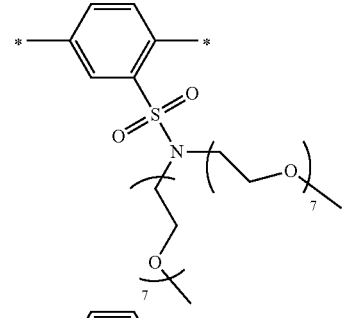
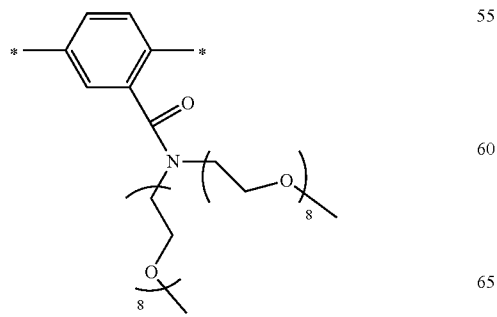
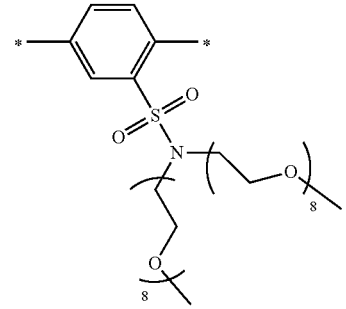

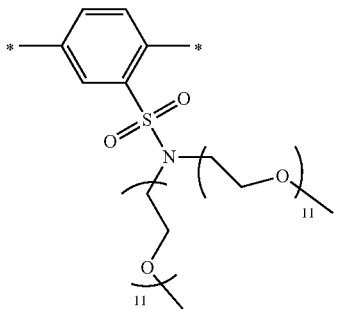

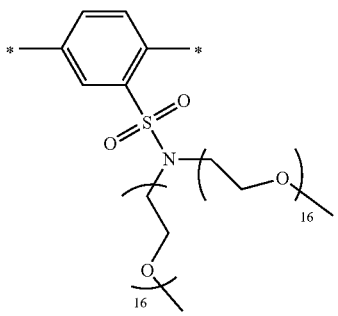

In some embodiments of formulae described herein, e.g., formula (I)-(IV), the aryl or heteroaryl co-monomers, e.g., $L^1$, $L^2$, $M^1$, $M^2$ and $M^3$ are independently selected from one of formulae (XXIII)-(XXVI):

(XXIII)

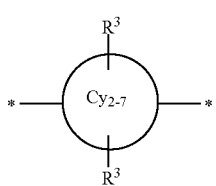

(XXIV)

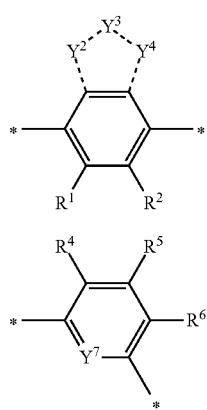

(XXV)

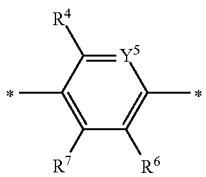

(XXVI)

wherein $Cy_{2-7}$ is an aryl or heteroaryl group comprising 2 to 7 fused and/or unfused rings;

$Y^2$, $Y^3$ and $Y^4$ are independently selected from —$CR^3$—, $NR^3$, N, O, S and —C(=O)— and together form a 5 or 6 membered fused aryl or heteroaryl ring;

each $R^3$ is one or more ring substituents independently selected from H, halogen, alkyl, substituted alkyl, aryl, substituted aryl, heteroaryl, substituted heteroaryl, acyl, substituted acyl, sulfonic acid, cyano, alkoxy substituted alkoxy and -$T^1$-$Z^1$;

$R^1$ and $R^2$ are independently selected from H, halogen, alkyl, substituted alkyl, aryl, substituted aryl, heteroaryl, substituted heteroaryl, acyl, substituted acyl, sulfonic acid, cyano, alkoxy, substituted alkoxy and -$T^1$-$Z^1$, or $R^1$ and $R^2$ together form a 5- or 6-membered fused aryl, heteroaryl, cycloalkyl or heterocycle ring which can be optionally substituted;

$Y^5$ is N or $CR^5$ and $Y^7$ is N or $CR^7$;

$R^4$-$R^7$ are independently selected from H, halogen, alkyl, substituted alkyl, aryl, substituted aryl, heteroaryl, substituted heteroaryl, acyl, substituted acyl, sulfonic acid, cyano, alkoxy, substituted alkoxy and -$T^1$-$Z^1$;

$Z^1$ is a chemoselective functional group or a linked signaling chromophore; and $T^1$ is a linker.

$Cy_{2-7}$ is an aryl or heteroaryl group that can include 2, 3, 4, 5, 6 or 7 rings which can be fused together to form one fused ring system or may be unfused (i.e., linked together via single covalent bonds). In some cases, $Cy_{2-7}$ is includes 2 or 3 unfused aryl and/or heteroaryl rings. In certain instances, $Cy_{2-7}$ is composed of 5 and/or 6 membered carbocyclic and/or heterocyclic rings. In certain cases, $Cy_{2-7}$ is a bicyclic, tricyclic or quadricyclic aryl or heteroaryl group, such as naphthalene, anthracene, acridine, or quinoline, etc.

In certain embodiments of formulae (XXIII)-(XXVI), the co-monomers (e.g., $M^1$, $M^2$ and $M^3$) are independently selected from one of the following structures (a) to (x):

(a)

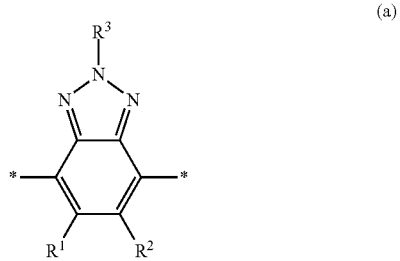

-continued
(b) 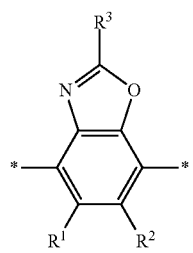
(c) 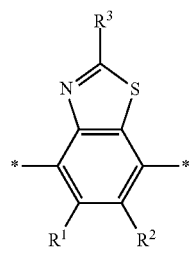
(d) 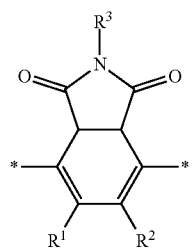
(e) 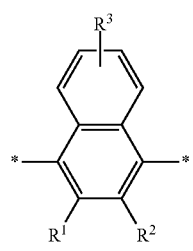
(f) 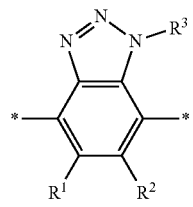
(g) 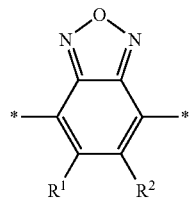
(h) 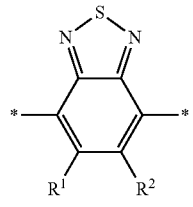
-continued
(i) 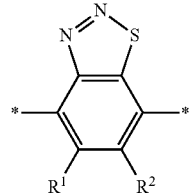
(j) 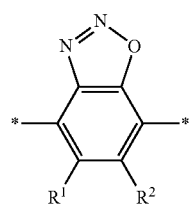
(k) 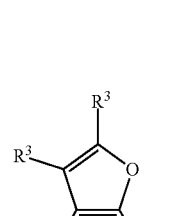
(l) 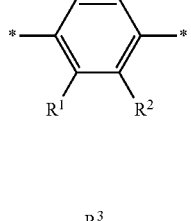
(m) 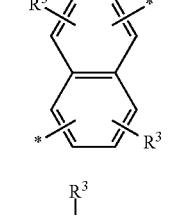
(n) 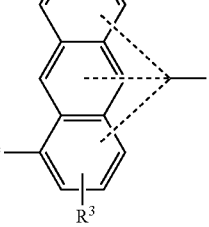

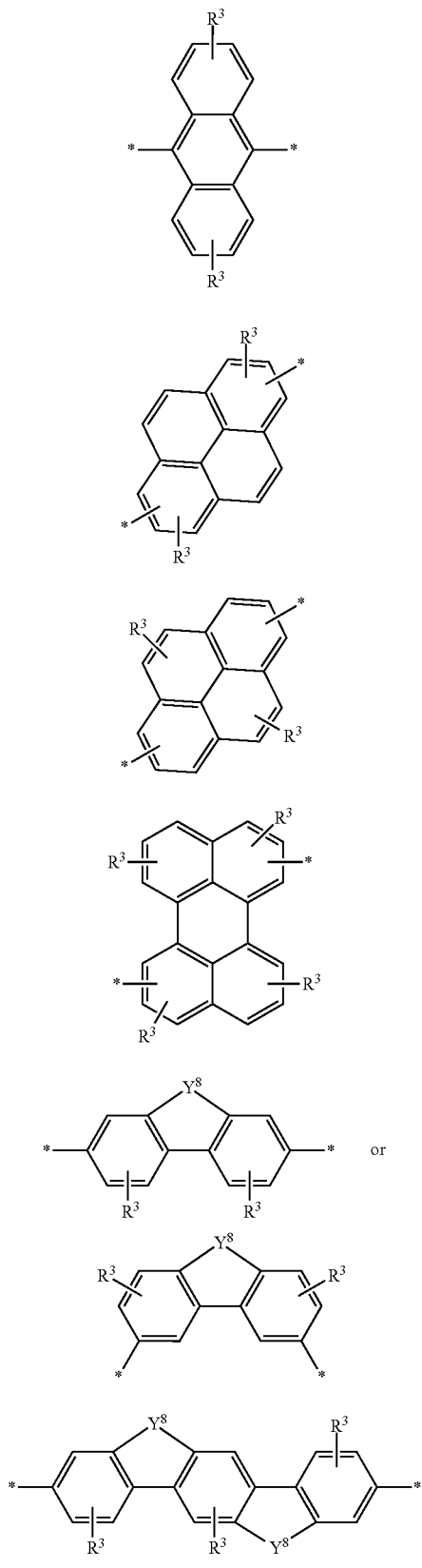

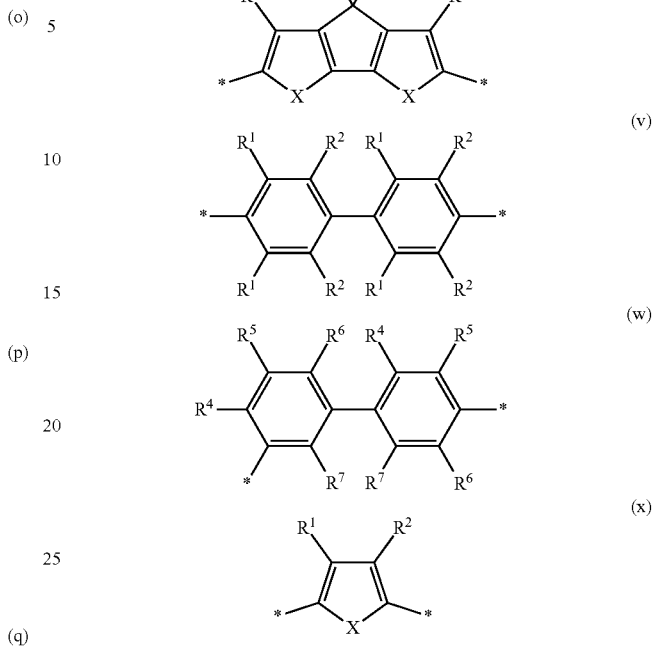

wherein:

each $Y^8$ is independently $C(R^3)_2$, $—C(R^3)_2C(R^3)_2—$, $—C(R^3)_2Si(R^3)_2—$, $NR^3$ or $Si(R^3)_2$;

X is S or O; each $R^3$ is independently H, a water solubilizing group (e.g., as described herein), amino, substituted amino, halogen, cyano, alkyl, substituted alkyl, aryl, substituted aryl, heteroaryl, substituted heteroaryl, acyl, substituted acyl, sulfonic acid, cyano, alkoxy, substituted alkoxy and $-T^1-Z^1$;

$R^1$ and $R^2$ are independently selected from H, halogen, alkyl, substituted alkyl, aryl, substituted aryl, heteroaryl, substituted heteroaryl, acyl, substituted acyl, sulfonic acid, cyano, alkoxy, substituted alkoxy and $-T^1-Z^1$, or $R^1$ and $R^2$ together form a 5- or 6-membered fused aryl, heteroaryl, cycloalkyl or heterocycle ring which can be optionally substituted (e.g., with an $R^3$ group);

$Z^1$ is a chemoselective functional group or a linked signaling chromophore; and $T^1$ is a linker.

In certain instances, $Y^8$ is $C(R^3)_2$. In certain instances, $Y^8$ is $—C(R^3)_2C(R^3)_2—$. In certain instances, $Y^8$ is $NR^3$. In certain instances, $Y^8$ is $Si(R^3)_2$. In certain embodiments of formula (a)-(x), when the co-monomer is a linking co-monomer, at least one of $R^1$-$R^7$ is $-T^1-Z^1$. In certain embodiments of formula (a)-(x), the co-monomer includes a water-solubilizing group (e.g., as described herein). In certain embodiments of formula (s), $R^3$ is H, halogen (e.g., F) or alkoxy (e.g., methoxy). It is understood that in any of the structures of (a)-(x) described herein, a N heteroatom can be included to convert a phenyl or fused benzo ring into a pyridyl or fused pyrido ring. Such heteroatom substituted versions of formula (a)-(x) are meant to be included in the present disclosure. In some instances of formula (XXIII)-(XXVI), one or more of the co-monomers have the structure of one of formula (s), where a benzo ring is replaced with a pyrido ring:

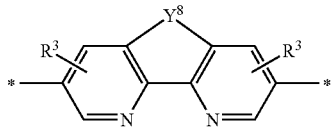
(5)
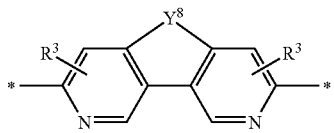
(10)
where $Y^8$ is independently $C(R^4)_2$, $-C(R^4)_2C(R^4)_2-$, $NR^4$ or $Si(R^4)_2$.
In some instances of formula (XXIII)-(XXVI) and (a)-(x), the co-monomers ($M^2$, $M^3$ and $M^4$) are independently selected from one of the following structures (ba) to (cd):
(ba)
(bb)
(bc)
(bd)
(be)
(bf)
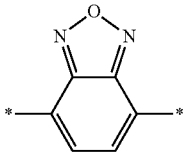
(bg)
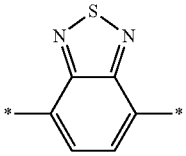
(bh)
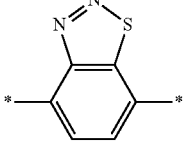
(bi)
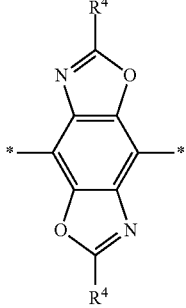
(bj)
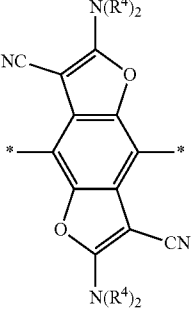
(bk)
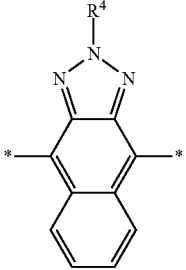
(bl)
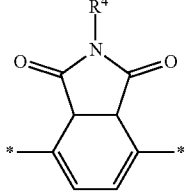

47
-continued
(bm)
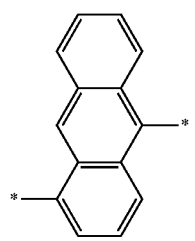
(bn)
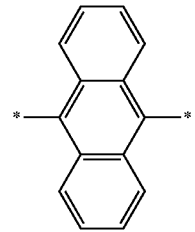
(bo)
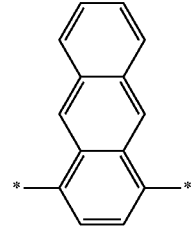
(bp)
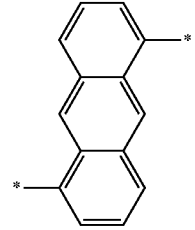
(bq)
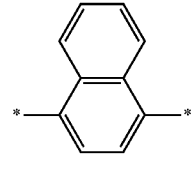
(br)
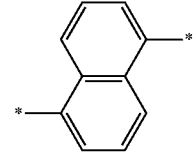
(bs)
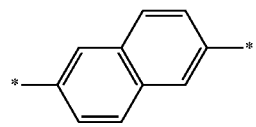
(bt)
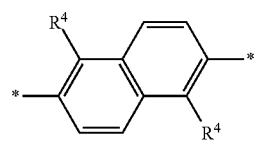
48
-continued
(bu)
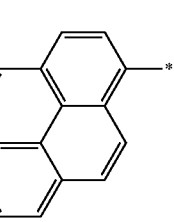
(bv)
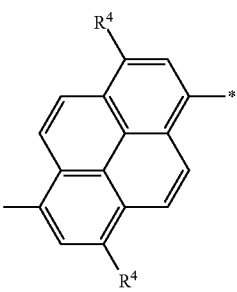
(bw)
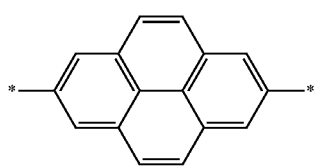
(bx)
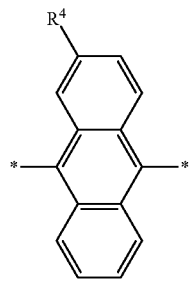
(by)
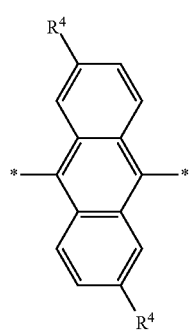
(bz)
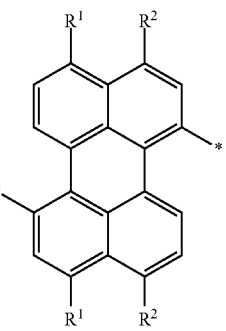

49

-continued

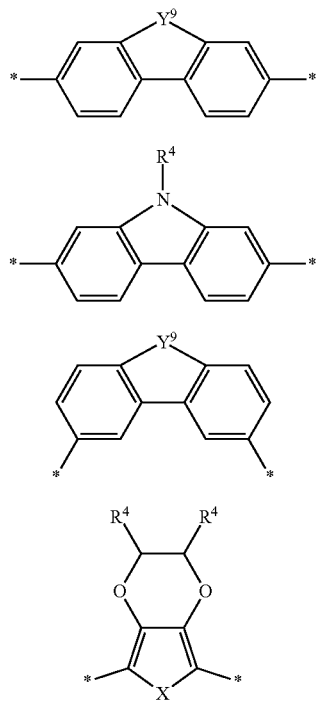

wherein:
Y⁹ is $C(R^4)_2$, $—C(R^4)_2C(R^4)_2—$ or $Si(R^4)_2$;
X is S or O;
each $R^4$ is independently H, a water solubilizing group (e.g., as described herein), alkyl, substituted alkyl, aryl, substituted aryl, heteroaryl, substituted heteroaryl, acyl, substituted acyl, sulfonic acid, cyano, alkoxy, substituted alkoxy and $-T^1-Z^1$; and
$R^1$ and $R^2$ are independently selected from H, halogen, alkyl, substituted alkyl, aryl, substituted aryl, heteroaryl, substituted heteroaryl, acyl, substituted acyl, sulfonic acid, cyano, alkoxy, substituted alkoxy and $-T^1-Z^1$, or $R^1$ and $R^2$ together form a 5- or 6-membered fused aryl or heteroaryl ring which can be optionally substituted. In certain embodiments of formula (ba)-(cd), when the co-monomer is a linking co-monomer, at least one of $R^4$ is $-T^1-Z^1$. In certain embodiments of formula (ba)-(cd), $R^4$ includes a water-solubilizing group (e.g., as described herein).

Fused Tricyclic Co-Monomers

Aryl and heteroaryl co-monomers of interest include fused tricyclic co-monomers. A fused tricyclic co-monomer is a co-monomer including a tricyclic aromatic group having three fused rings in a configuration where two aryl or heteroaryl 6-membered rings are fused to a central 5 or 6-membered carbocyclic or heterocyclic ring. In some cases, the fused tricyclic co-monomer includes two benzo or pyrido rings fused to a central 5 or 6 membered carbocyclic or heterocyclic ring. The fused tricyclic co-monomer can be pi-conjugated to adjacent co-monomers of a polymer backbone via any convenient ring atoms of the fused rings. The central 5- or 6-membered ring may be a carbocycle or a heterocycle, aromatic or partially saturated, and may further include a sidechain substituent, e.g., a WSG and/or a linker to a chemoselective tag. A bridged biphenyl co-monomer is a fused tricyclic co-monomer having a biphenyl group where the two phenyl rings are further linked with each other via a central 6 membered carbocyclic or heterocyclic ring. In

50 certain instances, the fused tricyclic co-monomer is described by the following structure:

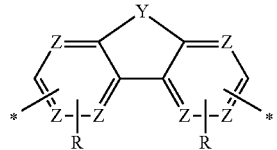

where:
Y is $C(R^3)_2$, $—C(R^3)_2C(R^3)_2—$, $—C(R^3)_2Si(R^3)_2—$, $NR^3$, $Si(R^3)_2$ or Se;
each Z is independently CH, CR or N;
each $R^3$ is independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, $-L^{11}-Z^1$, where $L^{11}$ is a linker and $Z^1$ is a chemoselective tag (e.g., a tag including a chemoselective functional group) and a WSG; and
each R is independently H or one or more aryl or heteroaryl substituents and wherein any two convenient R groups are optionally cyclically linked. In some cases, each R refers to one or two ring substituents independently selected from halogen, sulfonate, alkoxy, substituted alkoxy, alkyl and substituted alkyl and wherein any two convenient R groups are optionally cyclically linked. In certain instances, at least two of Z in each ring is CH or CR. In certain instances, one and only one of Z in each ring is N.

In certain instances, the fused tricyclic co-monomer is described by one of the following structures:

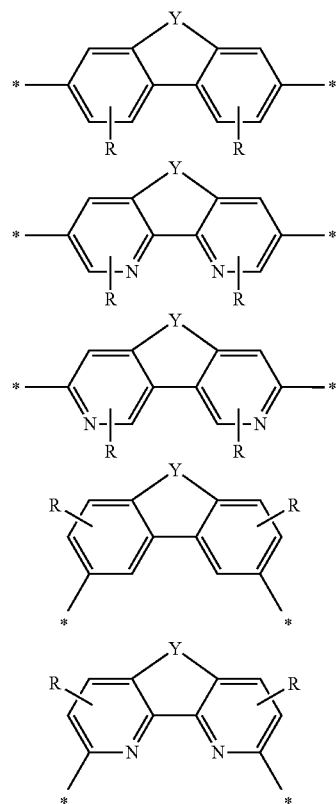

where:

Y is $C(R^3)_2$, $-C(R^3)_2C(R^3)_2-$, $-C(R^3)_2Si(R^3)_2-$, $NR^3$, $Si(R^3)_2$ or Se;

each $R^3$ is independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, $-L^{11}-Z^1$, where $L^{11}$ is a linker and $Z^1$ is a chemoselective tag (e.g., a tag including a chemoselective functional group) and a WSG; and each R is independently H, $R^3$ or one or more aryl or heteroaryl substituents and wherein any two convenient R groups are optionally cyclically linked. In some cases, each R refers to one or two ring substituents independently selected from halogen, sulfonate, alkoxy, substituted alkoxy, alkyl and substituted alkyl and wherein any two convenient R groups are optionally cyclically linked. The symbol "*" denotes a site for covalent attachment to the unsaturated backbone of a conjugated polymer, e.g., a π conjugated segment, a terminal group, a linker and a linked specific binding member. It is understood that for any of the formulae described herein which includes a 2,7-pi-conjugated fused tricyclic co-monomer, an analogous formula including an analogous 3,6-pi-conjugated co-monomer could also be depicted, and is meant to be encompassed by the present disclosure. In certain cases, the fused tricyclic co-monomer is a fluorene co-monomer where Y is $C(R^3)_2$. In some cases, the fused tricyclic co-monomer is a carbazole co-monomer where Y is $NR^3$. In some cases, the fused tricyclic co-monomer is a silole co-monomer where Y is $Si(R^3)_2$. In some cases, the fused tricyclic co-monomer is a bridged biphenyl co-monomer where Y is $-C(R^3)_2C(R^3)_2-$ or is $-C(R^3)_2Si(R^3)_2-$. In some cases, the fused tricyclic co-monomer is a bridged biphenyl co-monomer where Y is $-CHR^3CHR^3-$. In certain instances of any of the fused tricyclic co-monomers described herein, each R is independently selected from H, halogen, alkoxy, substituted alkoxy, alkyl and substituted alkyl. In certain cases, each R is independently selected from H, fluoro, chloro, methoxy, substituted alkoxy, alkyl and substituted alkyl.

In certain embodiments of the fused tricyclic co-monomer, the co-monomer includes two R substituent groups that are cyclically linked to provide a carbocyclic or heterocyclic ring A that is optionally further substituted:

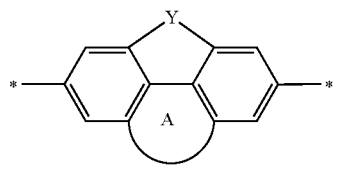

wherein Y is $C(R^3)_2$, $-C(R^3)_2C(R^3)_2-$, $-C(R^3)_2Si(R^3)_2-$, $NR^3$, $Si(R^3)_2$ or Se; and each $R^3$ is independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, $-L^{11}-Z^1$, where $L^{11}$ is a linker and $Z^1$ is a chemoselective tag (e.g., a tag including a chemoselective functional group) and a WSG. In certain cases, the fused tricyclic co-monomer has the structure:

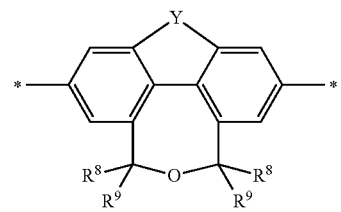

wherein each $R^8$-$R^9$ is independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, $-L^{11}-Z^1$, where $L^{11}$ is a linker and $Z^1$ is a chemoselective tag (e.g., a tag including a chemoselective functional group) and a WSG. In some cases of the co-monomer, Y is $C(R^3)_2$.

In certain instances, the fused tricyclic co-monomer is described by one of the following structures:

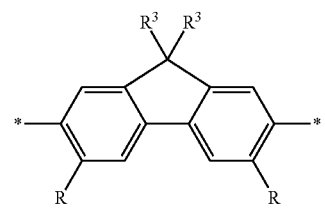

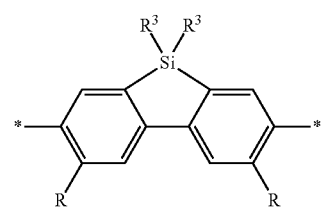

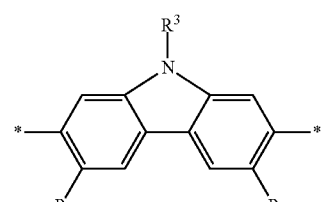

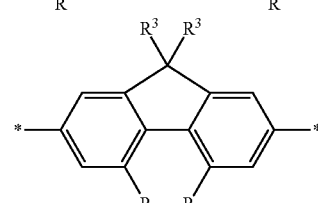

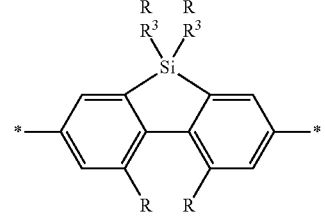

-continued

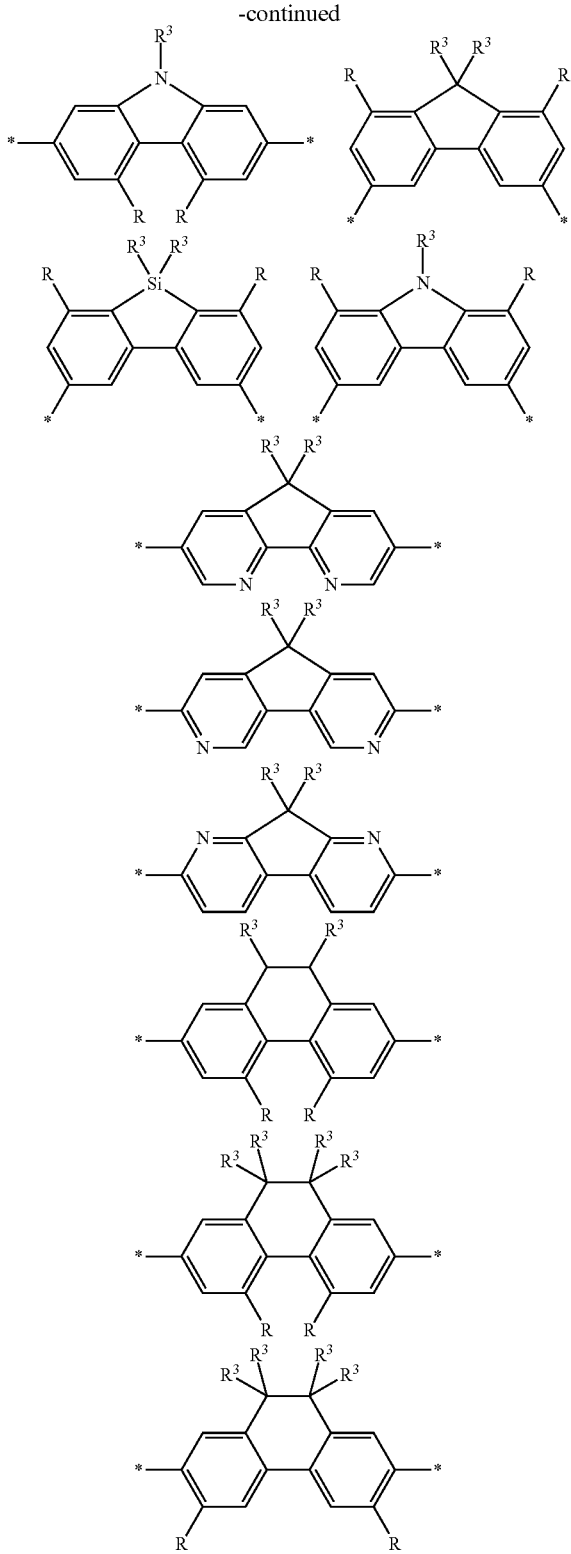

wherein:

each $R^3$ is independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, $-L^{11}-Z^1$, where $L^{11}$ is a linker and $Z^1$ is a chemoselective tag (e.g., a tag including a chemoselective functional group) and a WSG (e.g., as described herein); and each R is independently H, $R^3$ or one or more aryl or heteroaryl substituents. In some cases, each R refers to one or two ring substituents independently selected from halogen, sulfonate, alkoxy, substituted alkoxy, alkyl and substituted alkyl. In some cases, each R is fluoro or methoxy. In some cases, at least one $R^3$ is a WSG. In some cases, at least one $R^3$ is $-L^{11}-Z^1$.

In certain instances, the fused tricyclic co-monomer is described by the structure:

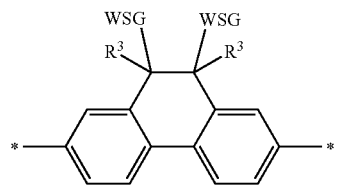

wherein each WSG is a branched or linear water soluble group, and each $R^3$ is H, alkyl, substituted alkyl. In certain cases, each WSG is a linear WSG (e.g., as described herein). In certain instances, the fused tricyclic co-monomer is described by the structure:

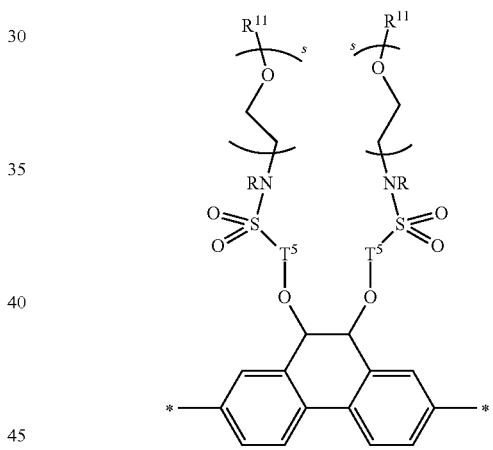

wherein $T^5$ is an optional linker; each s is independently an integer from 6 to 100 (e.g., 6 to 50); and each R and $R^{11}$ is independently hydrogen, an alkyl or a substituted alkyl.

A fused 6-5-6 tricyclic co-monomer is a co-monomer including a tricyclic aromatic group having three fused rings in the configuration 6-5-6, i.e. two benzo ring fused to a central 5 membered ring. The 5-membered ring may be a carbocycle or a heterocycle and may further include a sidechain substituent at the ring atom that is not fused to a benzo ring. In certain instances, the fused 6-5-6 tricyclic co-monomer is described by the following structure:

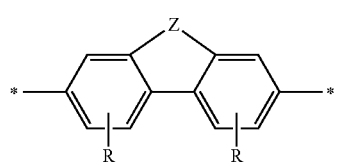

where: Z is —C(R$^1$)$_2$—, Si(R$^1$)$_2$— or —N(R$^1$)—; each R is independently H or one or more aryl substituents; and each R$^1$ is independently selected from branched non-ionic water soluble group (WSG), an alkyl, a substituted alkyl, an aralkyl, a substituted aralkyl, a PEG moiety and -L$^{11}$-Z$^1$, where L$^{11}$ is a linker and Z$^1$ is a chemoselective tag (e.g., a tag including a chemoselective functional group) or a WSG. As used in any of the formulae described herein, * denotes a site for covalent attachment to the unsaturated backbone of a conjugated polymer or an end group. In some embodiments, when Z is —N(R$^1$)—, the fused 6-5-6 tricyclic co-monomer is a carbazole co-monomer. Any convenient carbazole co-monomers may be utilized in the subject multichromophores. In some embodiments, when Z is —C(R$^1$)$_2$—, the fused 6-5-6 tricyclic co-monomer is a fluorene co-monomer. Any convenient fluorene co-monomers may be utilized in the subject multichromophores. In certain instances of the fused 6-5-6 tricyclic co-monomer, each R$^1$ is selected from a benzyl group substituted with one, two or more PEG moieties or an alkyl group substituted with two or more PEG moieties. In some embodiments, Z is —Si(R$^1$)$_2$—. It is understood that for any of the fluorene co-monomers described herein, also included in the present disclosure is the corresponding co-monomer where the C atom of Z is replaced with Si.

A fluorene co-monomer is a co-monomer including an aromatic group having a 9H-fluorene core structure substituted at the 9 position with any convenient sidechain substituent(s). In some cases, the fluorene co-monomer is a 9,9-disubstituted fluorene. The fluorene co-monomer is conjugated to adjacent polymeric backbone groups via any convenient positions of the fluorene core structure, such as any two positions of positions 1-8 (see numbering scheme below). In some embodiments, the fluorene core structure is linked to adjacent groups of the polymer backbone via the 2 and 7 positions. In certain embodiments, the fluorene co-monomer is described by the following structure:

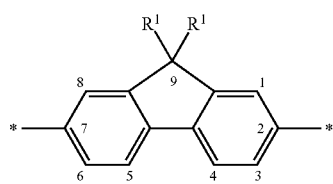

where: each R$^1$ is independently selected from a branched non-ionic water soluble group (WSG) an alkyl, a substituted alkyl, an aralkyl, a substituted aralkyl, a PEG moiety and -L$^{11}$-Z$^1$, where L$^{11}$ is a linker and Z$^1$ is a chemoselective tag (e.g., a tag including a chemoselective functional group) or a WSG. In certain instances of the fluorene co-monomer, each R$^1$ is a branched non-ionic water soluble group (WSG). In certain instances of the fluorene co-monomer, each R$^1$ is selected from a benzyl group substituted with one, two or more PEG moieties or an alkyl group substituted with two or more PEG moieties. The Z$^1$ functional group may find use in covalently linking the multichromophore to an acceptor chromophore (e.g., as described herein). In certain instances, Z$^1$ includes an amino group for covalently linking to the acceptor chromophore. In certain instances, Z$^1$ includes an carboxylic acid group, or derivative thereof, for covalently linking to the acceptor chromophore. In certain embodiments, L$^{11}$ is a branched linker that links to two or more Z$^1$ groups (e.g., WSGs). In certain instances, the fluorene co-monomer is further substituted with a R$^5$ and/or R$^6$ substituent located at one, two or more positions selected from positions 1, 3, 4, 5, 6 and 8, where R$^5$ and R$^6$ are independently selected from a water solubilizing group (WSG) and an aryl substituent (e.g., as described herein).

In certain instances, the fluorene co-monomer is described by the structure:

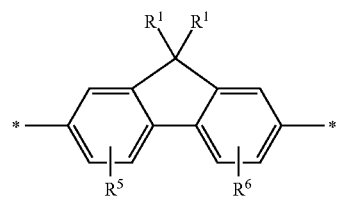

where: each R$^1$ is as defined above; and R$^5$ and R$^6$ are independently selected from H, a water solubilizing group, or an aryl substituent (e.g., as described herein).

In some instances, the fluorene co-monomer is described by the structure:

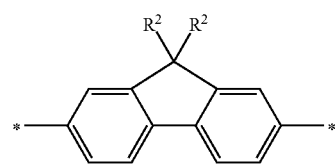

where each R$^2$ is a alkyl substituted with a water solubilizing group or a branched linker connected to two or more water solubilizing groups (e.g., a PEG-disubstituted benzyl or a PEG substituted alkyl). In certain instances of the fluorene co-monomer, each R$^2$ is a benzyl group substituted with one, two or three PEG moieties (e.g., —O(CH$_2$CH$_2$O)$_n$R' where R' is H or an alkyl and n is 1-20, e.g., 3-16 such as n is 8-16). In certain instances of the fluorene co-monomer, each R$^2$ is a benzyl group substituted with one —O(CH$_2$CH$_2$O)$_n$R' group (e.g., at the 2, 3 or 4 position), where R' is H or an alkyl and n is 1-20, e.g., 3-16 such as n is 8-16. In certain instances of the fluorene co-monomer, each R$^2$ is a benzyl group substituted with two —O(CH$_2$CH$_2$O)$_n$R' groups (e.g., at the 2,4-, 3,4- or 3,5-positions), where each R' is independently H or an alkyl and each n is independently 1-20, e.g., 3-16 such as n is 8-16. In certain instances of the fluorene co-monomer, each R$^2$ is a benzyl group substituted with three —O(CH$_2$CH$_2$O)$_n$R' groups (e.g., at the 2,4,6-, 2,4,5- or 3,4,5-positions), where each R' is independently H or an alkyl and each n is independently 1-20, e.g., 3-16 such as n is 8-16. In certain instances of the fluorene co-monomer, each R$^2$ is a lower alkyl group substituted with a trivalent branching group each substituted with two PEG moieties (e.g., a —CO—NR''$_2$ or —O(CH$_2$R'')$_2$ trivalent branching group where each R'' is independently a PEG moiety (e.g., —O(CH$_2$CH$_2$O)$_n$R' where R' is H or an alkyl and n is 1-20, e.g., 3-16 such as n is 8-16). In certain instances of the fluorene co-monomer, each R$^2$ is a branched non-ionic water soluble group (WSG) e.g., as described herein.

In certain embodiments, the fluorene co-monomer is described by the following structure:

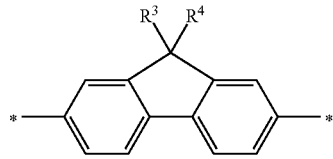

where $R^3$ is an alkyl substituted with a water solubilizing group (e.g., a PEG substituted alkyl) or a branched non-ionic water soluble group (WSG) (e.g., as described herein), and $R^4$ is $L^2$-$Z^2$ wherein $L^2$ is a linker and $Z^2$ is a chemoselective tag (e.g., for conjugation to an acceptor chromophore). In some instances, the fluorene co-monomer is described by the structure:

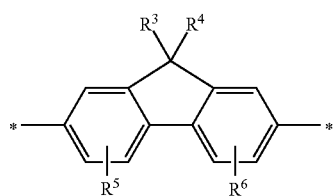

wherein: $R^3$ is a substituent comprising a water solubilizing group (e.g., as described herein) or a branched non-ionic water soluble group (WSG) (e.g., as described herein); $R^4$ is $L^2$-$Z^2$ wherein $L^2$ is a linker and $Z^2$ is a chemoselective tag (e.g., for conjugation to an acceptor chromophore); and $R^5$ and $R^6$ are independently selected from H, a water solubilizing group and an aryl substituent (e.g., an alkyl, a substituted alkyl, an alkoxy, a substituted alkoxy, a halogen or a nitro). In certain instances of the fluorene co-monomer, $R^3$ is a lower alkyl group substituted with a trivalent branching group each substituted with two PEG moieties (e.g., a —CO—NR"$_2$ or —O(CH$_2$R")$_2$ trivalent branching group where each R" is a PEG moiety (e.g., —O(CH$_2$CH$_2$O)$_n$R' where R' is H or an alkyl and n is 6-20, e.g., 8-16 such as n is 12-16). In certain instances of the fluorene co-monomer, $R^3$ is a branched non-ionic water soluble group (WSG) e.g., as described herein.

Any of the fluorene co-monomers described herein may be utilized in the subject multichromophores, e.g., multichromophores of formulae (I)-(IV). In some cases, the multichromophores include, as part of the polymeric backbone, one of the following structures:

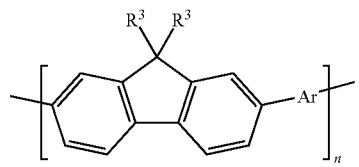

where each $R^3$ is independently a water solubilizing group connected via an optional linker, or an optionally substituted alkyl, aralkyl or aryl group; Ar is an optionally substituted aryl or heteroaryl group; n is an integer from 1 to 100,000; and the terminals are sites for covalent attachment to the unsaturated backbone of a conjugated polymer or an end group. In certain embodiments, each $R^3$ is independently a substituted alkyl group. In certain embodiments, each $R^3$ is independently a substituted aralkyl group. In some cases, each $R^3$ and each Ar are independently substituted (via an optional linker) with a water solubilizing group, an acceptor chromophore, a chemoselective functional group or a specific binding moiety.

Any of the co-monomers described herein (e.g., co-monomers of formula (I)-(V), (a)-(k), (a)-(x) and (ba)-(cd)) can include a water solubilizing group WSG (e.g., as described herein). In some embodiments, the aryl and heteroaryl co-monomer includes a branched non-ionic WSG that is selected from one of the following structures:

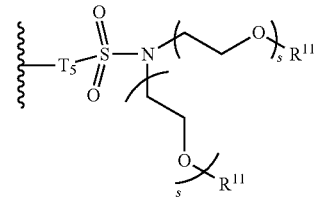

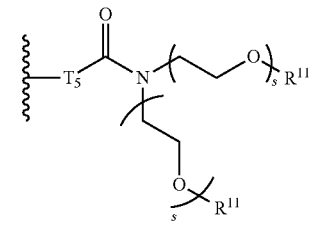

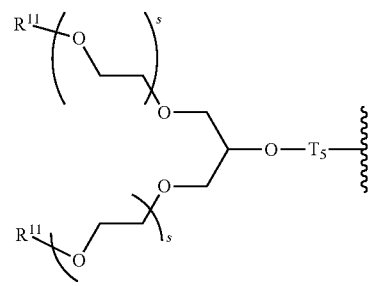

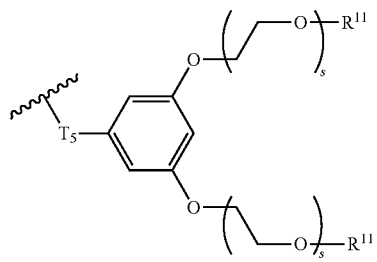

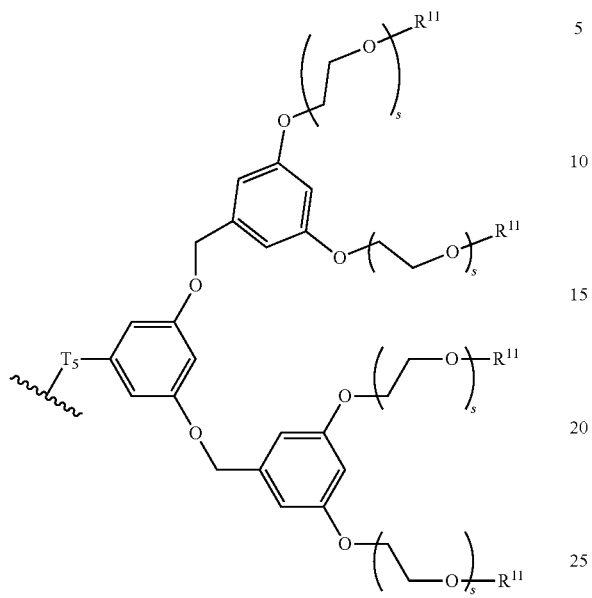

wherein: $T^5$ is an optional linker to the co-monomer; each s is independently an integer from 6 to 50 or 6-30, such as 6 to 20, 11 to 20, 12 to 20, or 12 to 16; and each $R^{11}$ is independently hydrogen, an alkyl or a substituted alkyl. In certain cases, each s is independently 6, 7, 8, 9, 10, 11, 12, 13, 14, 15, 16, 17, 18, 19 or 20. In some cases, each s is 11. In some cases, each s is 12. In some cases, each s is 13. In some cases, each s is 14. In some cases, each s is 15. In some cases, each s is 16. In some cases, each s is 17. In some cases, each s is 18. In some cases, each s is 19. In some cases, each s is 20. In some embodiments, $T^5$ is an alkyl linker, such as a C1-C6 alkyl linker. In some embodiments, $T^5$ is a substituted alkyl linker. In some embodiments, $T^5$ is an alkoxy linker (e.g., —O-alkyl-). In some embodiments, $T^5$ is a substituted alkoxy.

In certain instances of the co-monomers, the aryl and heteroaryl co-monomer includes a WSG (e.g., $R^3$ and/or $R^4$) selected from one of the following structures:

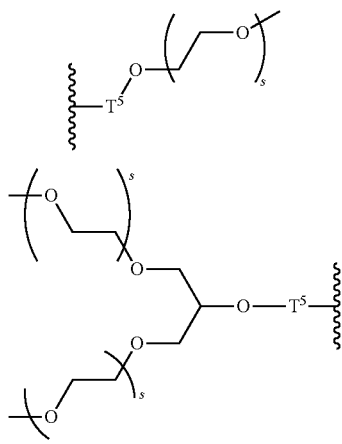

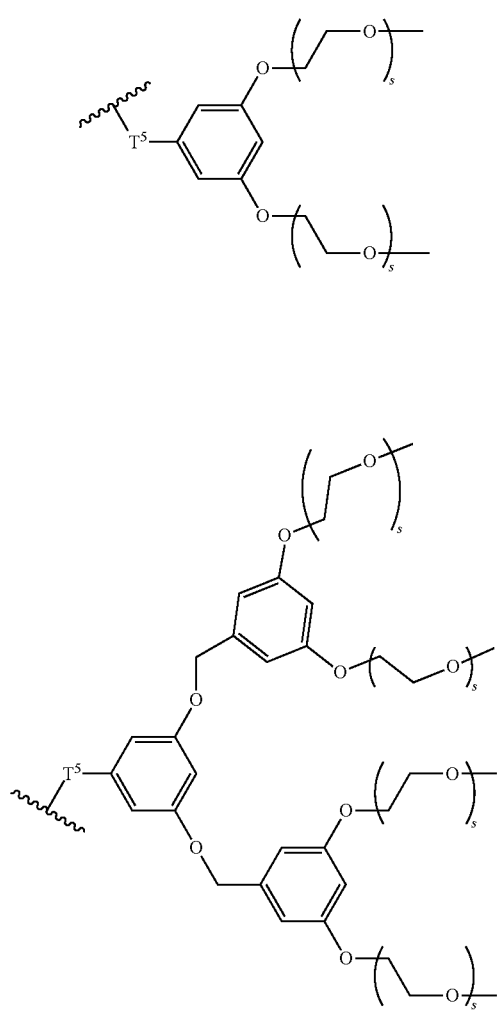

wherein: $T^5$ is an optional linker; and each s is an integer from 1 to 50. In certain instances, each s is independently 1 to 20, such as 3 to 20, 3 to 15, 3 to 12, or 6 to 20 or 6 to 12 or 12-16. In certain cases, each s is independently 1, 2, 3, 4, 5, 6, 7, 8, 9, 10, 11 or 12. In some cases, each s is 3. In some cases, each s is 4. In some cases, each s is 5. In some cases, each s is 6. In some cases, each s is 7. In some cases, each s is 8. In some cases, each s is 9. In some cases, each s is 10. In some cases, each s is 11. In some embodiments, $T^5$ is an alkyl linker, such as a C1-C6 alkyl linker. In some embodiments, $T^5$ is a substituted alkyl linker. In some embodiments, $T^5$ is an alkoxy linker (e.g., —O-alkyl-). In some embodiments, $T^5$ is a substituted alkoxy.

In certain embodiments of the formulae described herein, e.g., formulae (I)-(IV), the co-monomers (e.g., $M^1$, $M^2$ and/or $M^3$) are independently selected from one of the following structures:

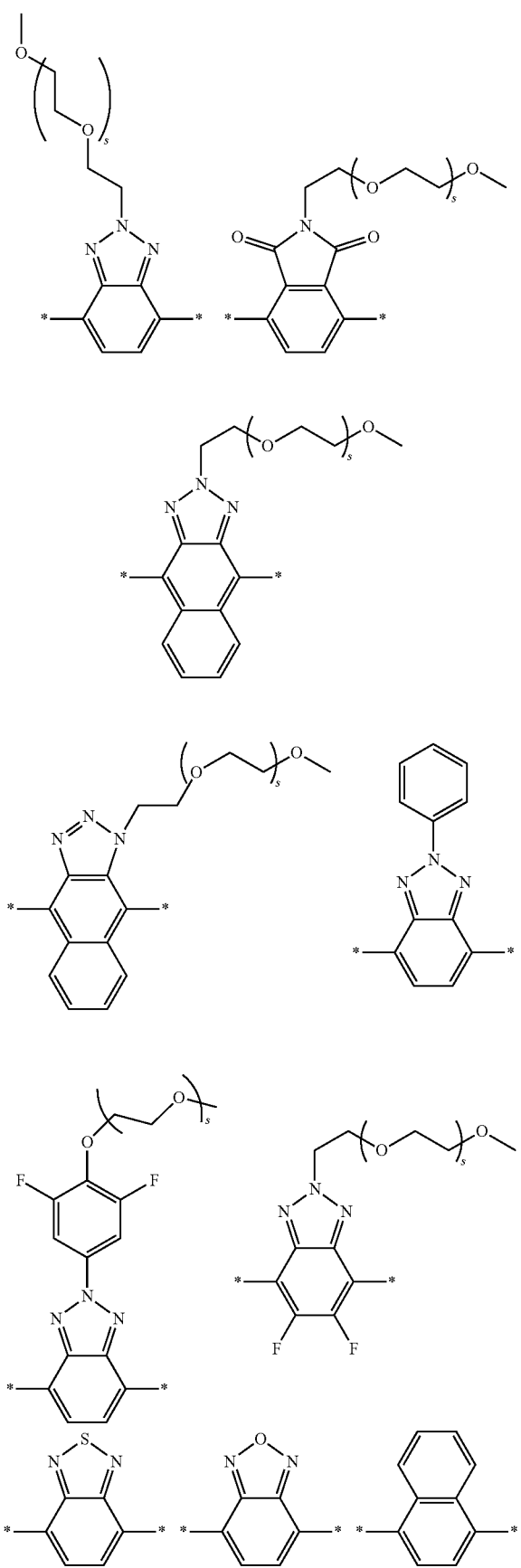
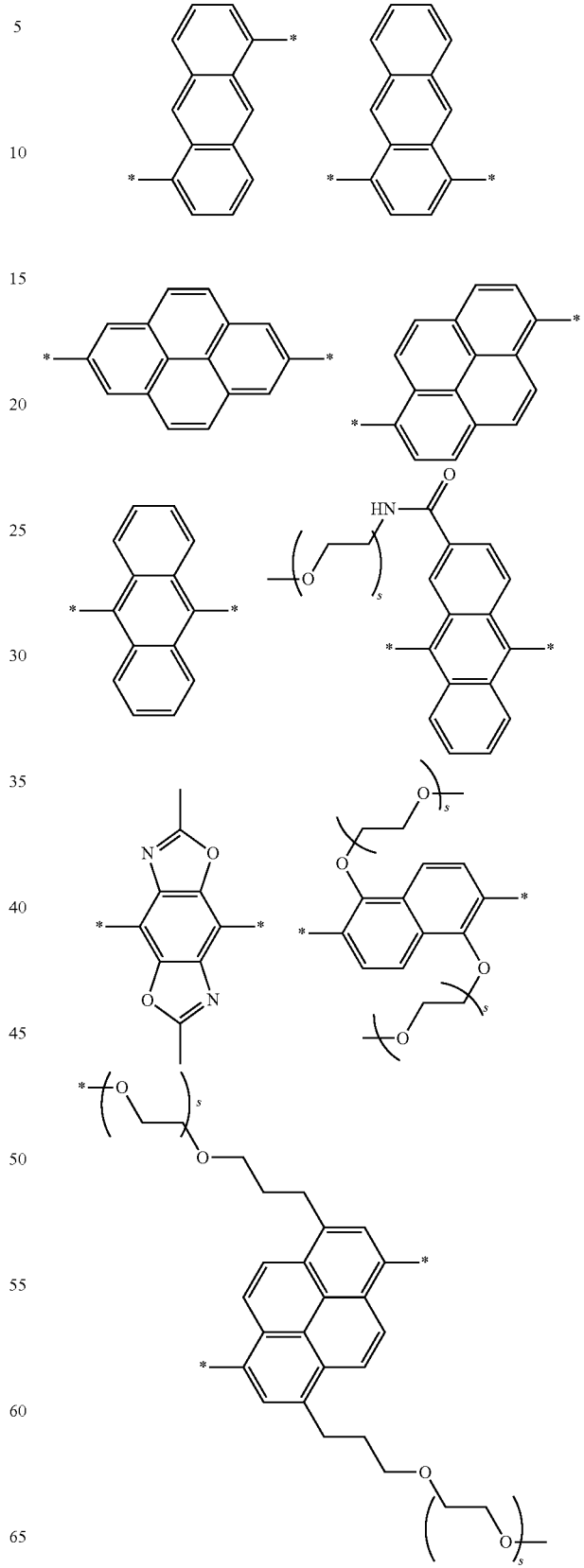

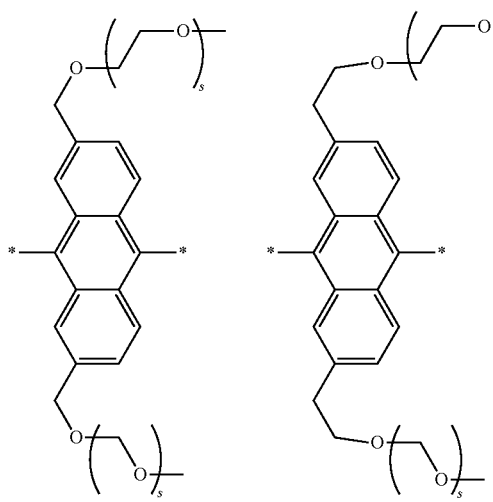
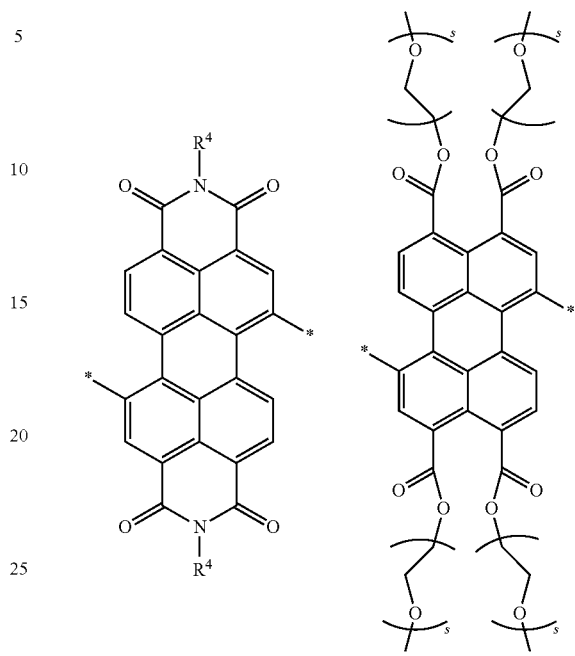
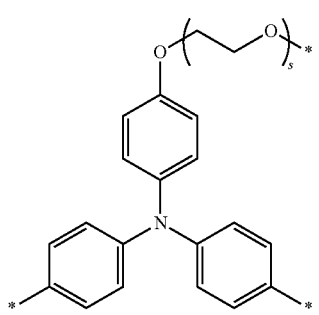
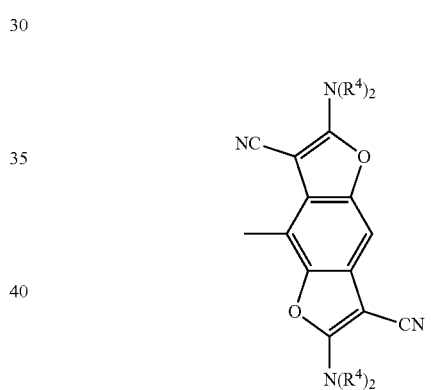
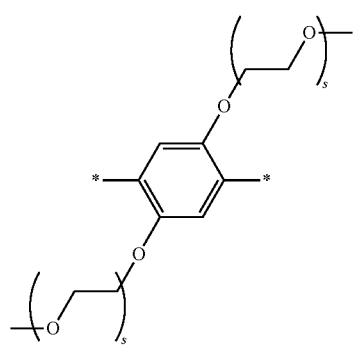
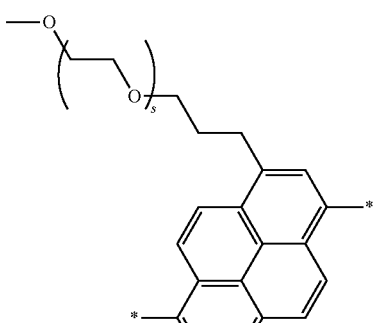
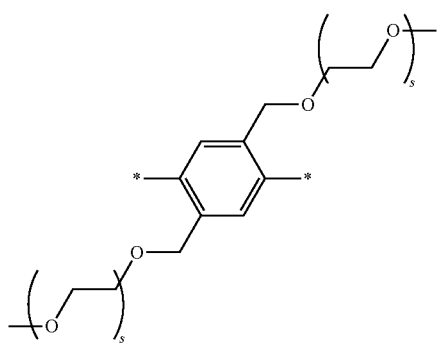
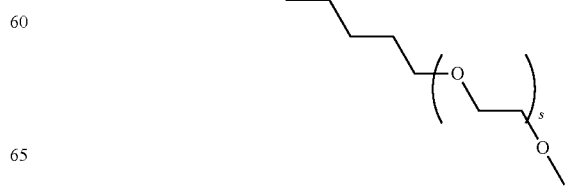

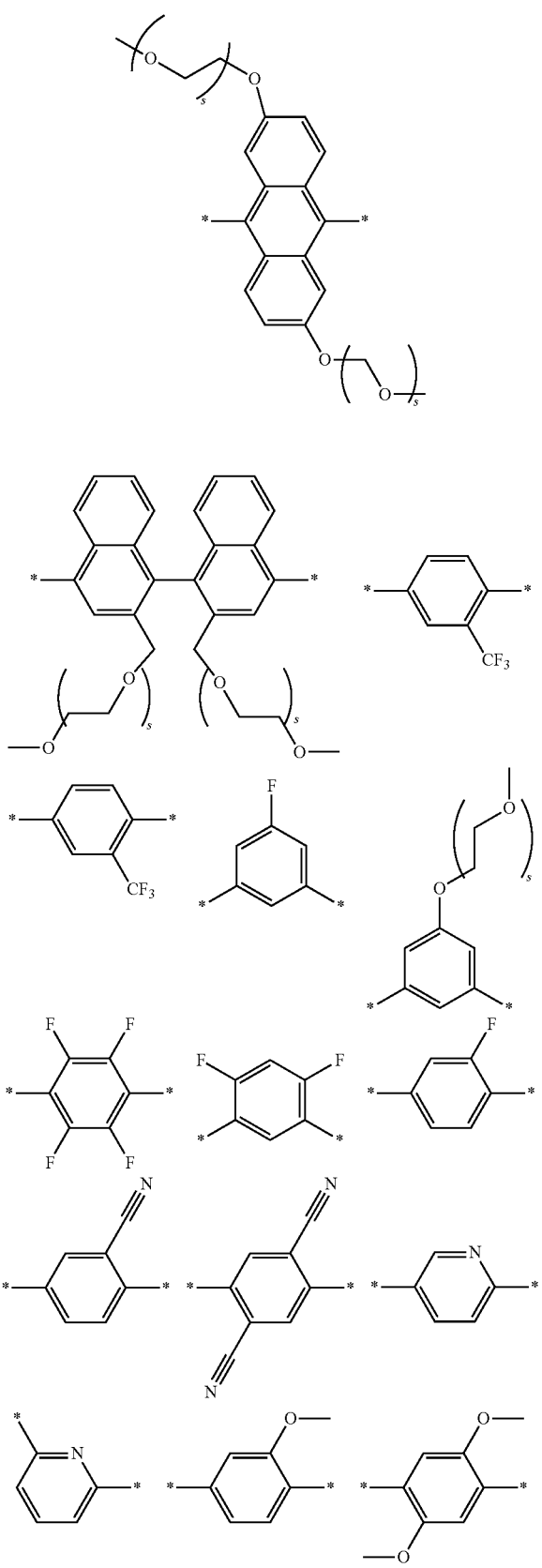

where each s is independently 1-30, such as 6-30, such as 6 to 20, 11 to 20, 12 to 20, or 12 to 16. In certain cases, each s is independently 6, 7, 8, 9, 10, 11, 12, 13, 14, 15, 16, 17, 18, 19 or 20. In some cases, each s is 4. In some cases, each s is 5. In some cases, each s is 6. In some cases, each s is 7. In some cases, each s is 8. In some cases, each s is 9. In some cases, each s is 10. In some cases, each s is 11. In some cases, each s is 12. In some cases, each s is 13. In some cases, each s is 14. In some cases, each s is 15. In some cases, each s is 16. In some cases, each s is 17. In some cases, each s is 18. In some cases, each s is 19. In some cases, each s is 20.

In some instances, the multichromophore (e.g., of formulae (I)-(IV)) includes a co-monomer (e.g., $L^1$) linked to a signaling chromophore having the one of the following structures:

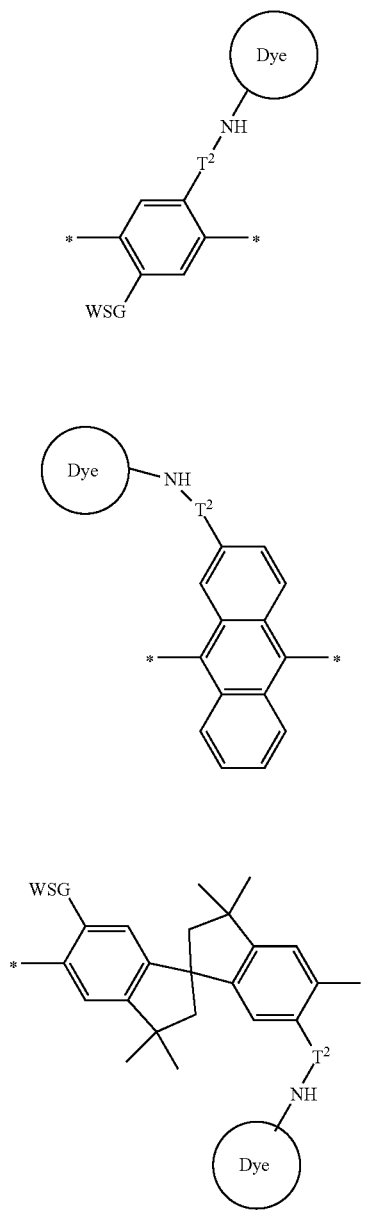

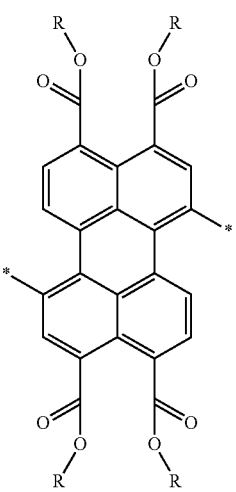

a′

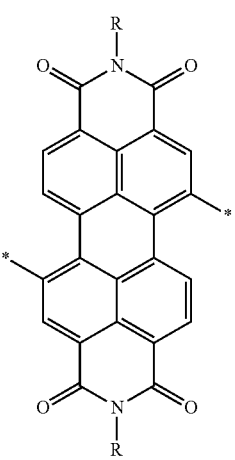

b′

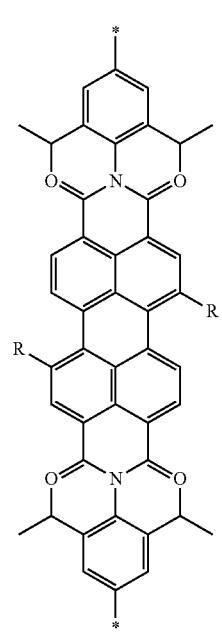

c′ wherein WSG is an optional water soluble group; $T^2$ is a linker; and Dye is the signaling chromophore.

In certain embodiments, the aryl or heteroaryl co-monomer is an optionally substituted co-monomer selected from 2,1,3-benzothiadiazole, 2,1,3-benzoxadiazole, benzoxidazole, benzoselenadiazole, benzotellurodiazole, naphthoselenadiazole, 4,7-di(thien-2-yl)-2,1,3-benzothiadiazole, squaraine dyes, quinoxalines, perylene, perylene diimides, diketopyrrolopyrrole, thienopyrazine low bandgap commercial dyes, olefins, and cyano-substituted olefins and isomers thereof. In some instances, aryl and heteroaryl co-monomers which find use in the subject multichromophores are selected from a′-m′ having the structure:

69
-continued

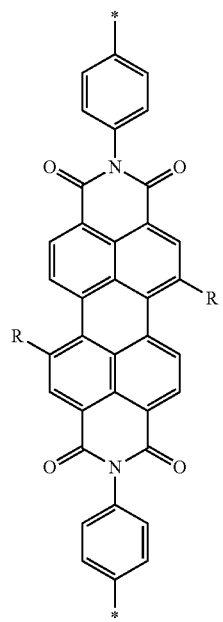

d'

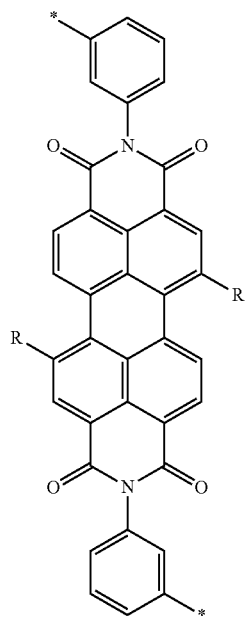

e'

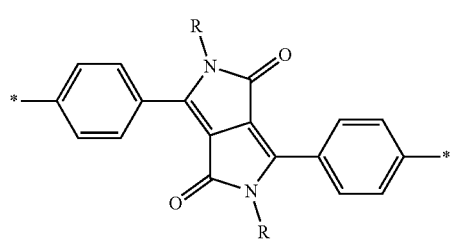

f'

70
-continued

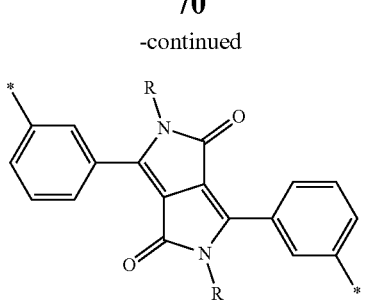

g'

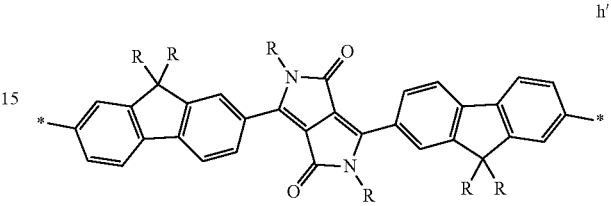

h'

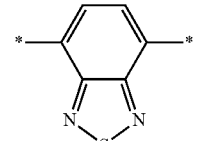

i'

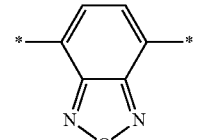

j'

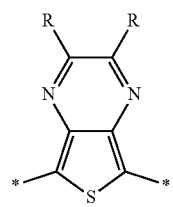

k'

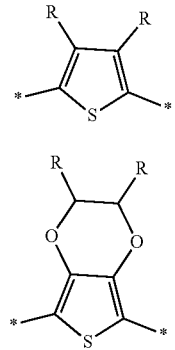

l' m' wherein *=a site for covalent attachment to unsaturated backbone and each R is independently H, a non-ionic side group capable of imparting solubility in water (e.g., a WSG), or -$L^2$-$Z^2$, where $L^2$ is a linker and $Z^2$ is a chemoselective tag or a linked metal complex. In certain instances of a'-m', each R is H or a water solubilizing group (e.g., as described herein). In certain cases, each R is an alkyl or a benzyl substituted with one or more $(CH_2)_x(OCH_2CH_2)_yOCH_3$ where each x is independently an integer from 0-20, each y is independently an integer from 0 to 50. In certain instances of a'-m', each R is $(CH_2)_3(OCH_2CH_2)_{11}OCH_3$. In certain instances of a'-m', each R is H or a non-ionic branched WSG, e.g., as described herein.

In some embodiments, the multichromophore includes an absorbance-modifying co-monomer having the following structure:

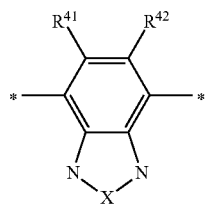

where X is O or S, $R^{41}$ and $R^{42}$ are each independently, H, halogen, a WSG, an alkyl, a substituted alkyl, an alkoxy and a substituted alkoxy. In certain instances, X is O. In some instances, X is S. In certain embodiments, X is O and $R^{41}$ and $R^{42}$ are each H. In certain embodiments, X is S and $R^{41}$ and $R^{42}$ are each H.

Any of the absorbance-modifying co-monomers described above may be utilized in the subject multichromophores, e.g., multichromophores of formulae (I)-(IV).

Water Solubilizing Groups

The repeat units of the subject polymeric dyes can be substituted at any convenient positions with a water solubilizing group. As used herein, the terms "water solubilizing group", "water soluble group" and WSG are used interchangeably and refer to a group or substituent that is well solvated in aqueous environments e.g., under physiological conditions, and that imparts improved water solubility upon the molecules to which it is attached. In some embodiments, a WSG increases the solubility of the multichromophore in a predominantly aqueous solution, as compared to a control multichromophore which lacks the WSG. The water solubilizing groups may be any convenient hydrophilic group that is well solvated in aqueous environments.

A water soluble polymeric dye of the present disclosure has solubility under aqueous conditions that makes it especially suitable for application to a variety of biological assays. The subject water soluble polymers, and conjugates thereof, can be resistant to undesirable aggregation which provides advantageous fluorescence and spectroscopic properties in various biological assays. Aggregation of dyes is undesirable because it can lead to reduced fluorescent signals, e.g., via aggregation-caused quenching of dye fluorescence. The subject water-soluble conjugated polymer dyes can be used as fluorescent reporters for a variety of biosensors and provide signals of exceptional brightness with a range of options for excitation and emission wavelength for applications such as Flow Cytometry, and imaging.

In certain instances, a water soluble polymeric dye has a solubility in water or buffer of 10 mg/mL or more, such as 20 mg/mL or more, 30 mg/mL or more, 40 mg/mL or more, 50 mg/mL or more, 60 mg/mL or more, 70 mg/mL or more, 80 mg/mL or more, 90 mg/mL or more, 100 mg/mL or more, or even more. It is understood that water soluble polymeric dyes may be configured to, under certain conditions, form discrete water solvated nanoparticles in aqueous systems. In certain cases, the water solvated nanoparticles are resistant to aggregation and find use in a variety of biological assays.

Any convenient water solubilizing groups (WSG's) may be included in the multichromophores described herein (e.g., multichromophores of formulae (I)-(IV)) to provide for increased water-solubility. While the increase in solubility may vary, in some instances the increase (as compared to the compound without the WSG(s)) is 2 fold or more, e.g., 5 fold, 10 fold, 25 fold, 50 fold, 100 fold or more. In some cases, the hydrophilic water solubilizing group is charged, e.g., positively or negatively charged. In certain cases, the hydrophilic water solubilizing group is a neutral hydrophilic group. In some embodiments, the WSG is branched (e.g., as described herein). In certain instances, the WSG is linear. In some embodiments, the WSG is a hydrophilic polymer, e.g., a polyethylene glycol, a modified PEG, a peptide sequence, a peptoid, a carbohydrate, an oxazoline, a polyol, a dendron, a dendritic polyglycerol, a cellulose, a chitosan, or a derivative thereof. Water solubilizing groups of interest include, but are not limited to, carboxylate, phosphonate, phosphate, sulfonate, sulfate, sulfinate, sulfonium, ester, polyethylene glycols (PEG) and modified PEGs, hydroxyl, amine, amino acid, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —$SO_3$M', —$PO_3$M', —$NR_3$+, Y', $(CH_2CH_2O)_pR$ and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —$(CH_2CH_2O)_{yy}CH_2CH_2XR^{yy}$, —$(CH_2CH_2O)_{yy}CH_2CH_2X$—, —$X(CH_2CH_2O)_{yy}CH_2CH_2$—, glycol, and polyethylene glycol, wherein yy is selected from 1 to 1000, X is selected from O, S, and $NR^{zz}$, and $R^{zz}$ and $R^{yy}$ are independently selected from H and $C_{1-3}$ alkyl. In some cases, a WSG is $(CH_2)_x(OCH_2CH_2)_yOCH_3$ where each x is independently an integer from 0-20, each y is independently an integer from 0 to 50. In some cases, the water solubilizing group includes a non-ionic polymer (e.g., a PEG polymer) substituted at the terminal with an ionic group (e.g., a sulfonate).

A WSG can include a water-soluble polymer. Water-soluble polymers of interest include, but are not limited to, polyalkylene oxide based polymers, such as polyethylene glycol "PEG" (See. e.g., "Poly(ethylene glycol) Chemistry: Biotechnical and Biomedical Applications", J. M. Harris, Ed., Plenum Press, New York, N.Y. (1992); and "Poly (ethylene glycol) Chemistry and Biological Applications", J. M. Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964, and U.S. Pat. Nos. 4,179,337; 5,075,046; 5,089,261; 5,100,992; 5,134,192; 5,166,309; 5,171,264; 5,213,891; 5,219,564; 5,275,838; 5,281,698; 5,298,643; 5,312,808; 5,321,095; 5,324,844; 5,349,001; 5,352,756; 5,405,877; 5,455,027; 5,446,090; 5,470,829; 5,478,805; 5,567,422; 5,605,976; 5,612,460; 5,614,549; 5,618,528; 5,672,662; 5,637,749; 5,643,575; 5,650,388; 5,681,567; 5,686,110; 5,730,990; 5,739,208; 5,756,593; 5,808,096; 5,824,778; 5,824,784; 5,840,900; 5,874,500; 5,880,131; 5,900,461; 5,902,588; 5,919,442; 5,919,455; 5,932,462; 5,965,119; 5,965,566; 5,985,263; 5,990,237; 6,011,042; 6,013,283; 6,077,939; 6,113,906; 6,127,355; 6,177,087; 6,180,095; 6,194,580; 6,214,966).

Examples of water soluble polymers of interest include, but are not limited to, those containing a polyalkylene oxide, polyamide alkylene oxide, or derivatives thereof, including polyalkylene oxide and polyamide alkylene oxide comprising an ethylene oxide repeat unit of the formula —($CH_2$—$CH_2$—O)—. Further examples of polymers of interest include a polyamide having a molecular weight greater than 1,000 Daltons of the formula —[C(O)—X—C(O)—NH—Y—NH]n- or —[NH—Y—NH—C(O)—X—C(O)]$_n$—, where X and Y are divalent radicals that may be the same or different and may be branched or linear, and n is a discrete integer from 2-100, such as from 2 to 50, and where either or both of X and Y comprises a biocompatible, substantially non-antigenic water-soluble repeat unit that may be linear or branched. Further examples of water-soluble repeat units comprise an ethylene oxide of the formula —($CH_2$—$CH_2$—O)— or —(O—$CH_2$—$CH_2$)—. The number of such water-soluble repeat units can vary significantly, with the number of such units being from 2 to 500, 2 to 400, 2 to 300, 2 to 200, 2 to 100, 6-100, for example from 2 to 50 or 6 to 50, such as 6 to 40, 6 to 30, 6 to 20, 8 to 20 or 10 to 20, e.g., 10, 11, 12, 13, 14, 15, 16, 17, 18, 19, or 20. An example of an embodiment is one in which one or both of X and Y is selected from: —(($CH_2$)$_{n1}$—($CH_2$—$CH_2$—O)$_{n2}$—($CH_2$)— or —(($CH_2$)$_{n1}$—(O—$CH_2$—$CH_2$)$_{n2}$—($CH_2$)$_{n-1}$—), where n1 is 1 to 6, 1 to 5, 1 to 4, or 1 to 3, and where n2 is 2 to 50, 2 to 25, 2 to 15, 2 to 10, 2 to 8, or 2 to 5. A further example of an embodiment is one in which X is —($CH_2$—$CH_2$)—, and where Y is —($CH_2$—$CH_2$—$CH_2$—O)$_3$—$CH_2$—$CH_2$—$CH_2$)— or —($CH_2$—$CH_2$—$CH_2$—O—$CH_2$—$CH_2$)$_3$—$CH_2$)—. In certain instances, the co-monomer includes 2, 3, or 4 WSG each independently having the formula —($CH_2$)$_{n1}$—($CH_2$—$CH_2$—O)$_{n2}$R' where R' is H, C1-6alkyl or substituted C1-6alkyl, n1 is 1 to 6, 1 to 5, 1 to 4, or 1 to 3, and n2 is 2 to 50, such as 6 to 40, 6 to 30, 6 to 20, 8 to 20 or 10 to 20, e.g., 10, 11, 12, 13, 14, 15, 16, 17, 18, 19, or 20.

As used herein a modified polymer, such as a modified PEG, refers to water soluble polymers that have been modified or derivatized at either or both terminals, e.g., to include a terminal substituent (e.g., a terminal alkyl, substituted alkyl, alkoxy or substituted alkoxy, etc) and/or a terminal linking functional group (e.g., an amino or carboxylic acid group suitable for attachment via amide bond formation) suitable for attached of the polymer to the multichromophore (e.g., via a branching group). The subject water soluble polymers can be adapted to include any convenient linking groups.

It is understood that in some cases, the water soluble polymer can include some dispersity with respect to polymer length, depending on the method of preparation and/or purification of the polymeric starting materials. In some instances, the subject water soluble polymers are monodisperse. In some instances, the subject water soluble polymers are substantially monodisperse, e.g., include 20 wt % or less of non-target species, such as 15 wt % or less, 10 wt % or less, 5 wt % or less, 2 wt % or less or 1 wt % or less.

The water soluble polymer can include one or more spacers or linkers. Examples of spacers or linkers include linear or branched moieties comprising one or more repeat units employed in a water-soluble polymer, diamino and or diacid units, natural or unnatural amino acids or derivatives thereof, as well as aliphatic moieties, including alkyl, aryl, heteroalkyl, heteroaryl, alkoxy, and the like, which can contain, for example, up to 18 carbon atoms or even an additional polymer chain.

The water soluble polymer moiety, or one or more of the spacers or linkers of the polymer moiety when present, may include polymer chains or units that are biostable or biodegradable. For example, polymers with repeat linkages have varying degrees of stability under physiological conditions depending on bond lability. Polymers with such bonds can be categorized by their relative rates of hydrolysis under physiological conditions based on known hydrolysis rates of low molecular weight analogs, e.g., from less stable to more stable, e.g., polyurethanes (—NH—C(O)—O—)>polyorthoesters (—O—C((OR)(R'))—O—)>polyamides (—C(O)—NH—). Similarly, the linkage systems attaching a water-soluble polymer to a target molecule may be biostable or biodegradable, e.g., from less stable to more stable: carbonate (—O—C(O)—O—)>ester (—C(O)—O—)>urethane (—NH—C(O)—O—)>orthoester (—O—C((OR)(R'))—O—)>amide (—C(O)—NH—). In general, it may be desirable to avoid use of a sulfated polysaccharide, depending on the lability of the sulfate group. In addition, it may be less desirable to use polycarbonates and polyesters. These bonds are provided by way of example, and are not intended to limit the types of bonds employable in the polymer chains or linkage systems of the water-soluble polymers useful in the modified aldehyde tagged polypeptides disclosed herein.

Branched Non-Ionic Water Soluble Groups

In some cases, a WSG is a branched non-ionic water soluble group. A branched non-ionic water soluble group can be attached to a co-monomer at any convenient location to provide a sidechain group that projects away from the backbone of the conjugated polymer to provide high solvation in an aqueous environment. In some cases, the branched non-ionic water soluble groups (WSG) comprise two or more water soluble polymers (e.g., as described herein) each having 6-100, such as 6-50, 6-40 or 6-30 monomeric units.

A branched non-ionic water soluble group (WSG) comprises a branching group that is linked to the co-monomer to which it is attached and provides further linkages to two, three or more non-ionic water soluble polymers. In some instances, the two or more water soluble polymers that are utilized in the WSG are polyethylene glycol (PEG) groups or modified PEG groups. Any convenient branching groups can be utilized that provide for 3 or more points of attachment (e.g., 4 or more), such as one point of attachment to the co-monomer of the conjugated polymer backbone and two or more attachments (e.g., 2, 3, 4 or more) to non-ionic water soluble polymers. The branching group can be attached to the co-monomer and the non-ionic water soluble polymers via optional linkers utilizing any convenient linking functional groups and linking chemistries. In certain instances, the branching group is non-aromatic. In certain instances, the branching group is cyclic. In some cases, the branching group is a substituted aryl or heteroaryl ring, e.g., a trisubstituted or tetrasubstituted aryl ring, such as a trisubstituted or tetrasubstituted phenyl ring, or a trisubstituted or tetrasubstituted heteroaryl ring, such as a trisubstituted or tetrasubstituted pyridyl ring. In certain instances, the branching group is acyclic. In some instances, the branching group is an atom, e.g., C, Si, N. In certain instances, the branching group is a linking functional group such as an amido or a sulfonamide group. In certain instances, the branching group is an amino acid residue or a branched linker, such as a glycerol or an amino-glycerol.

In some instances, the branched non-ionic WSG is independently selected from: —$Y^1$—($CH_2CH_2O$)$_r$—R'; —$Y^1$—O—CH[($CH_2$)$_q$—O—($CH_2CH_2O$)$_r$—R']$_2$; and —$Y^1$—$CH_2$-Ph($Y^1$—($CH_2CH_2O$)$_r$—R')$_s$; wherein $Y^1$ is selected from a covalent bond, —O—, —CONH—, —NHCO—, NHSO$_2$—, —SO$_2$—NH—, —CONR—, —NRCO—, NRSO$_2$—, —SO$_2$—NR— (e.g., where R is alkyl or substituted alkyl), —(CH$_2$)$_q$—SO$_2$—NH—, —(CH$_2$)$_q$—CONH— and —(CH$_2$)$_q$—O—, q and r are each independently an integer from 1 to 50, s is 1, 2 or 3 and each R' is independently H, alkyl (e.g., methyl) or substituted alkyl.

In some instances, the branched non-ionic WSG has one of the following formulae:

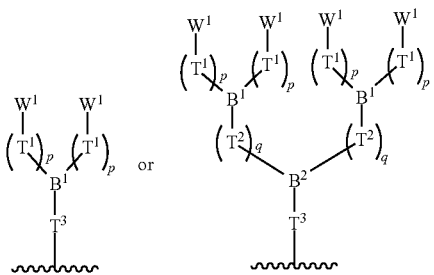

wherein:
each $B^1$ and $B^2$ are independently a branching group;
each $W^1$ is independently a non-ionic water soluble polymer, e.g., comprising 6 or more monomeric units;
$T^3$ is an optional linker to the fused 6-5-6 tricyclic co-monomer; and
each p and q are independently 0 or 1, wherein if present, each $T^1$ and each $T^2$ are independently a linker. In certain instances, each $W^1$ is independently a PEG or modified PEG polymer. In certain instances, each $W^1$ is independently selected from a substituted alkyl, a PEG or modified PEG group and a WSG. In certain instances, each $W^1$ is independently a PEG or modified PEG polymer of 6-30 monomeric units, such as 6-24 or 10-30, 10-24 or 10-20, 12-24, 12-20, 12-16 or 16-20 monomeric units.

In some instances, the branched non-ionic WSG has the following formula:

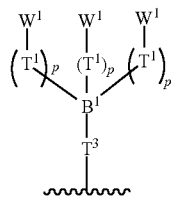

wherein:
each $B^1$ is a branching group;
each $W^1$ is independently a non-ionic water soluble polymer, e.g., comprising 6 or more monomeric units;
$T^3$ is an optional linker to the fused 6-5-6 tricyclic co-monomer; and
each p is independently 0 or 1, wherein if present, each $T^1$ is independently a linker. In certain instances, each $W^1$ is independently a PEG or modified PEG polymer. In certain instances, each $W^1$ is independently selected from a substituted alkyl, a PEG or modified PEG group and a WSG. In certain instances, each $W^1$ is independently a PEG or modified PEG polymer of 6-30 monomeric units, such as 6-24 or 10-30, 10-24 or 10-20, 12-24, 12-20, 12-16 or 16-20 monomeric units. In some embodiments of the branched non-ionic WSG, $B^1$ is a tetra-substituted aryl group (e.g., a 1,3,4,5-phenyl).

In some embodiments of the branched non-ionic WSG (e.g., as depicted in the formulae above), $B^1$ is selected from CH, N, C(=O)N, SO$_2$N, a tri-substituted aryl group (e.g., a 1,3,5-phenyl), a tetra-substituted aryl group, and a tri-substituted heteroaryl group. In some embodiments of the branched non-ionic WSG, each p is 0. In some embodiments of the branched non-ionic WSG, p is 1, and each $T^1$ is selected from —(CH$_2$)$_n$—O—, —O—(CH$_2$)$_n$—, —(CH$_2$)$_n$— and —O—, wherein n is from 1 to 12, e.g., 1 to 6. In some embodiments of the branched non-ionic WSG, each $T^2$ and/or $T^3$ is independently a C1-C12-alkyl linker, e.g., a C1-C6-alkyl linker, wherein one or more backbone atoms are optionally substituted with a heteroatom.

In some embodiments, the branched non-ionic WSG is selected from one of the following structures:

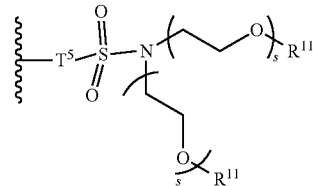

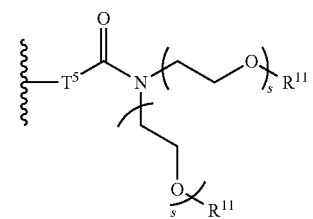

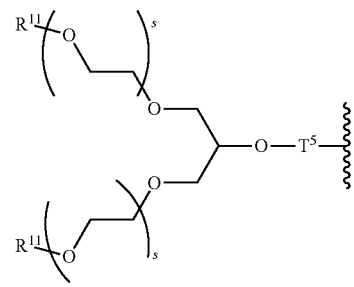

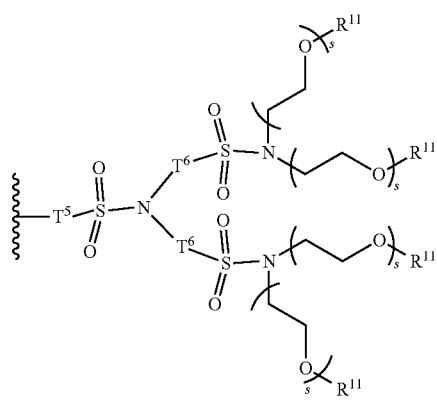

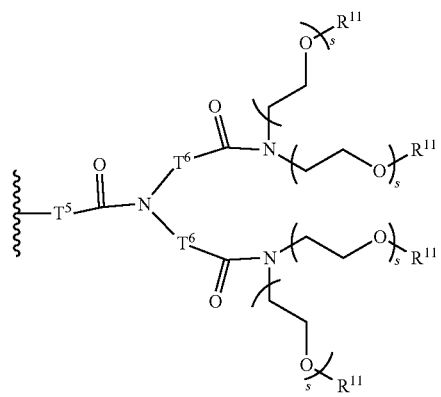

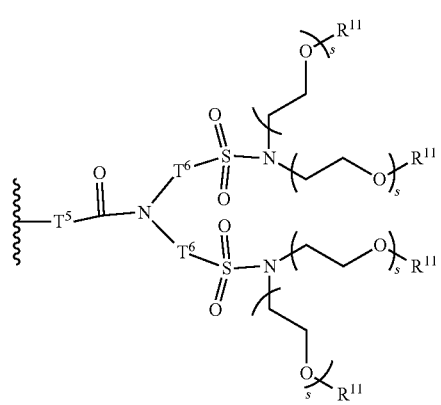

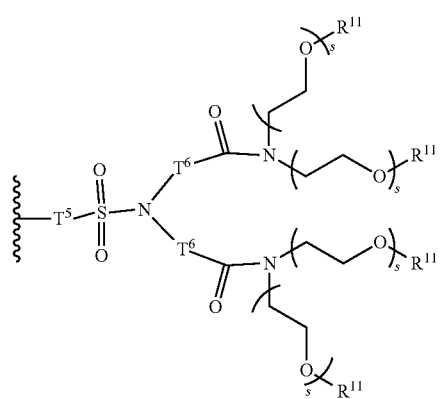

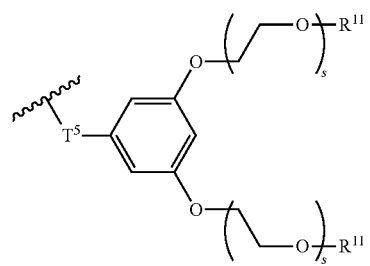

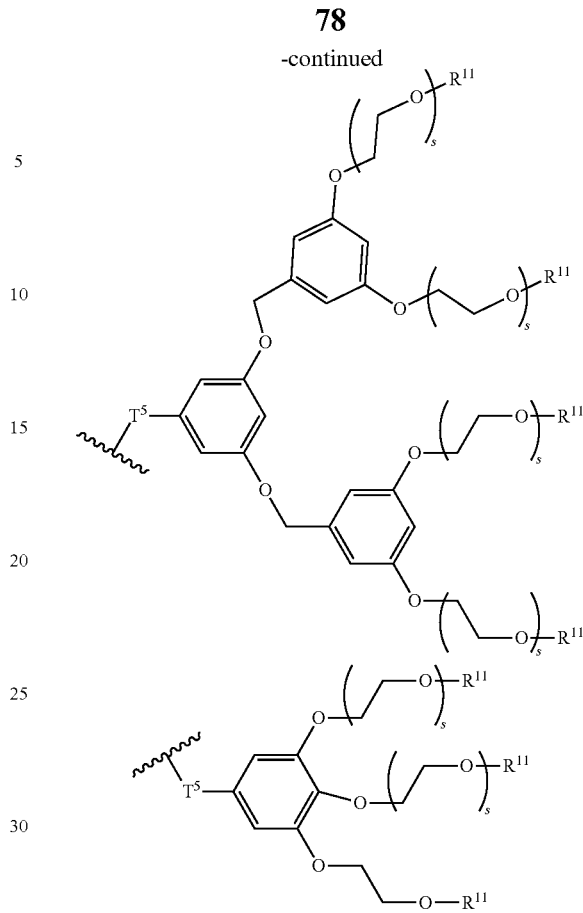

wherein:

T⁵ is an optional linker to the co-monomer (e.g., the fused 6-5-6 tricyclic co-monomer);

T⁶ is a linker;

each s is independently an integer from 6 to 100 (e.g., 6 to 50); and each $R^{11}$ is independently hydrogen, an alkyl or a substituted alkyl.

In certain instances, each s is independently 6 to 30, such as 6 to 24, 6 to 20, 11 to 20, 12 to 20, 12 to 18 or 12 to 16. In certain instances, each s is independently 6 to 30, such as 6 to 24, 8 to 24, 10 to 24, 12 to 24, 13 to 24, 14 to 24, 15 to 22 or 16 to 20. In some cases, each s is independently 11, 12, 13, 14, 15, 16, 17, 18, 19, 20, 21, 22, 23 or 24. In some embodiments, each s is independently 7 or more, such as 8, 9 or more, 10 or more, 11 or more, 12 or more, 13 or more, 14 or more, 15 or more, or even more, and in some cases, have up to 50 monomeric units, such as up to 40, up to 30 or up to 24 monomeric units. In some instances, each s is independently 6-30 monomeric units, such as 6-24 or 10-30, 10-24 or 10-20, 12-24, 12-20, 12-16 or 16-20 monomeric units. In some cases, each s is the same. In some embodiments of the branched non-ionic WSG, T⁵ and/or T⁶ is a C1-C12-alkyl linker, e.g., a C1-C6-alkyl linker, wherein one or more backbone atoms are optionally substituted with a heteroatom (e.g., an —O—). In some embodiments of the branched non-ionic WSG, each $R^{11}$ is H. In some embodiments of the branched non-ionic WSG, each $R^{11}$ is methyl.

In some embodiments, the π-conjugated segment includes a fluorene co-monomer substituted with two branched non-ionic WSG groups (e.g., as described herein) (e.g., disubstituted at the 9 position). In some embodiments of formula (I), $F^1$ is a fluorene co-monomer substituted with two linear non-ionic WSG groups (e.g., as described herein) (e.g., disubstituted at the 9 position). In some embodiments, the fluorene co-monomer is of the structure:

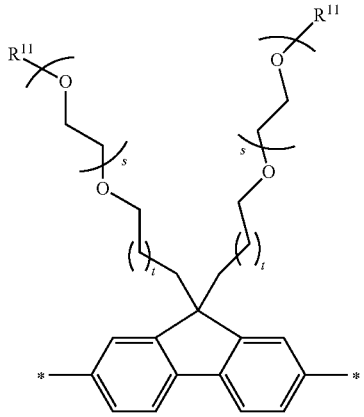

wherein s is 6-60; t is 0-10 (e.g., 0-6 such as 0, 1, 2, or 3); and $R^{11}$ is H, alkyl or substituted alkyl. In certain cases, each $R^{11}$ is methyl.

In some embodiments of the formulae, the co-monomer includes a substituent selected from $(CH_2)_x(OCH_2CH_2)_yOCH_3$ where each x is independently an integer from 0-20, each y is independently an integer from 0 to 50; and a benzyl optionally substituted with one or more halogen, hydroxyl, $C_1$-$C_{12}$ alkoxy, or $(OCH_2CH_2)_zOCH_3$ where each z is independently an integer from 0 to 50. In some instances, the substituent is $(CH_2)_3(OCH_2CH_2)_{11}OCH_3$. In some embodiments, one or more of the substituents is a benzyl substituted with at least one WSG groups (e.g., one or two WSG groups) selected from $(CH_2)_x(OCH_2CH_2)_yOCH_3$ where each x is independently an integer from 0-20 and each y is independently an integer from 0 to 50.

Multiple WSGs may be included at a single location in the subject multichromophores via a branching linker. In certain embodiments, the branching linker is an aralkyl substituent, further di-substituted with water solubilizing groups. As such, in some cases, the branching linker group is a substituent of the multichromophore that connects the multichromophore to two or more water solubilizing groups. In certain embodiments, the branching linker is an amino acid, e.g., a lysine amino acid that is connected to three groups via the amino and carboxylic acid groups. In some cases, the incorporation of multiple WSGs via branching linkers imparts a desirable solubility on the multichromophore. In some instances, the WSG is a non-ionic sidechain group capable of imparting solubility in water in excess of 50 mg/mL. In some instances, the WSG is a non-ionic sidechain group capable of imparting solubility in water in excess of 100 mg/mL. In some embodiments, the multichromophore includes substituent(s) selected from the group consisting of, an alkyl, an aralkyl and a heterocyclic group, each group further substituted with a include water solubilizing groups hydrophilic polymer group, such as a polyethylglycol (PEG) (e.g., a PEG group of 2-20 units).

In certain instances of any one of the formulae described herein, one or more of the co-monomers is substituted with a WSG and/or a linked signaling chromophore. Any convenient WSG can adapted for inclusion into a co-monomer of the subject polymeric dyes. In certain instances of any one of the formulae described herein, one or more of the co-monomers is substituted with a WSG that is independently selected from one of the following structures:

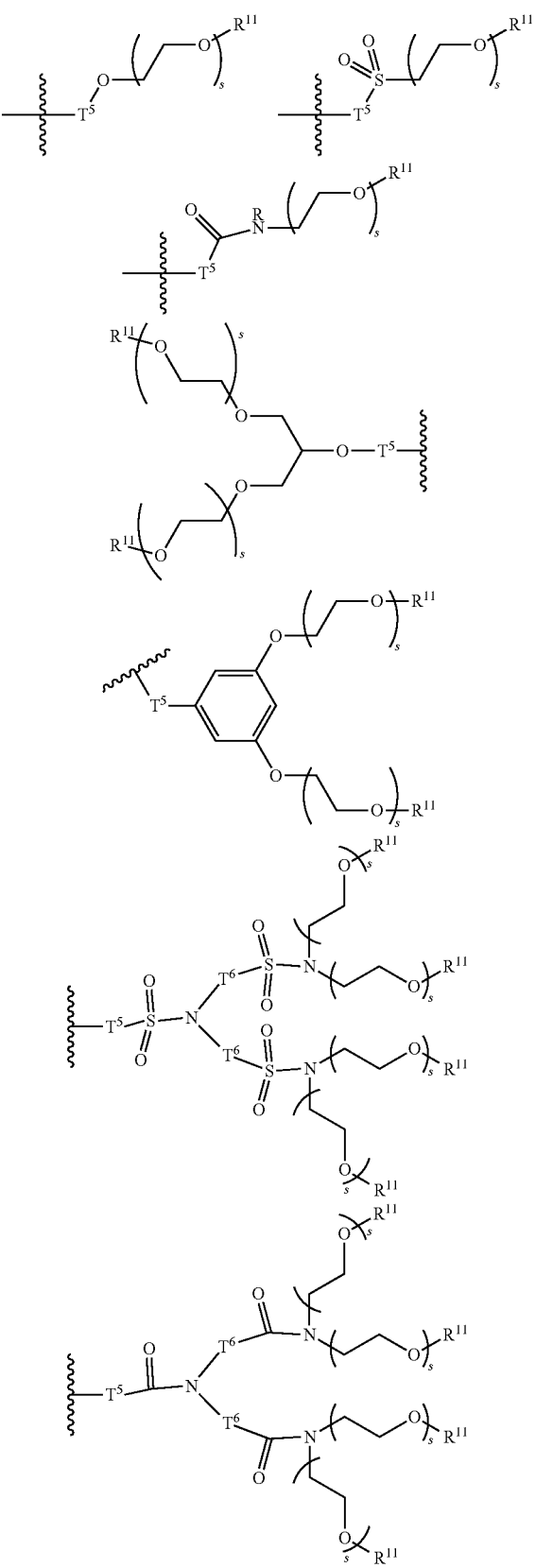

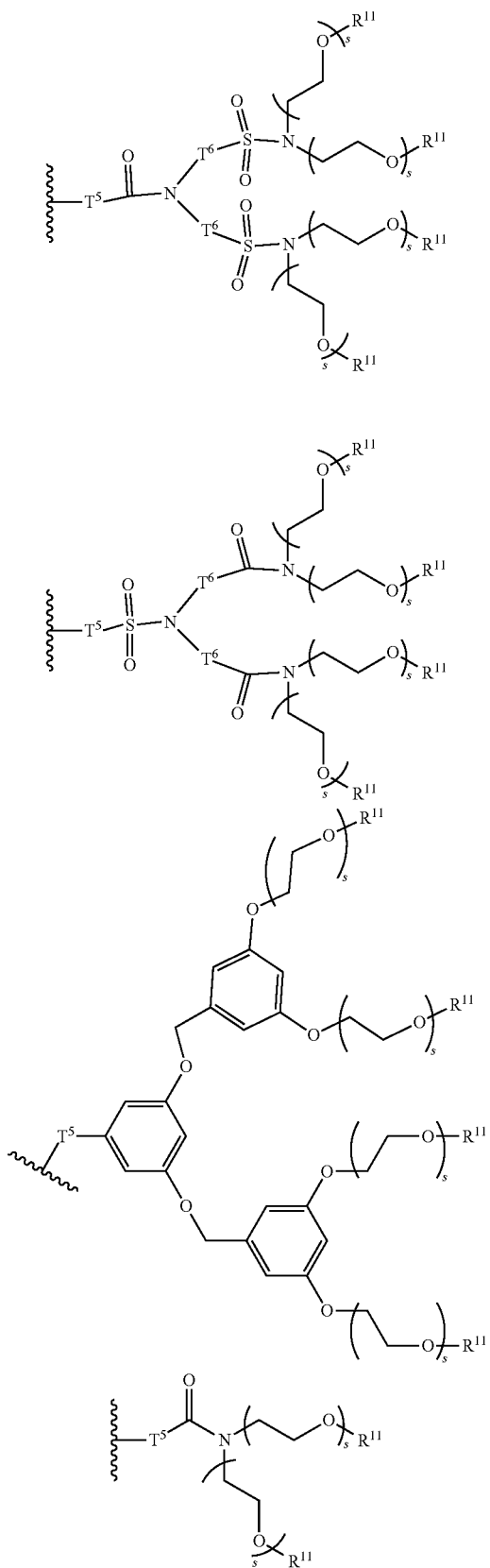

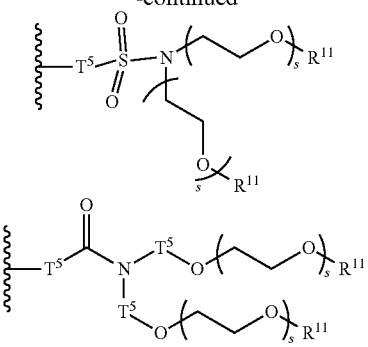

wherein: each $R^{11}$ is H, an alkyl (e.g., methyl) or a substituted alkyl; $T^5$ is an optional linker; $T^6$ is an linker; and each s is independently an integer from 1 to 100 (e.g., 1 to 50, or 6 to 50). In certain instances, each s is independently 1 to 50, such as 3 to 40, 3 to 30, 3 to 20, 3 to 15, 3 to 12, or 6 to 12. In certain cases, each s is independently 1, 2, 3, 4, 5, 6, 7, 8, 9, 10, 11, 12, 13, 14, 15, 16, 17, 18, 19 or 20. In some cases, each s is 3. In some cases, each s is 4. In some cases, each s is 5. In some cases, each s is 6. In some cases, each s is 7. In some cases, each s is 8. In some cases, each s is 9. In some cases, each s is 10. In some cases, each s is 11. In some cases, each s is 12. In some cases, each s is 14. In some cases, each s is 16. In some embodiments, $T^5$ is an alkyl linker, such as a C1-C12 or C1-C6 alkyl linker. In some embodiments, $T^5$ is a substituted alkyl linker. In some embodiments, $T^5$ is an alkoxy linker (e.g., —O-alkyl-). In some embodiments, $T^5$ is a substituted alkoxy. It is understood that hydroxy-terminated PEG chains instead of methoxy-terminated PEG chains may be utilized in any of the WSG groups described herein. In some embodiments, each $R^{11}$ is H. In some embodiments, each $R^{11}$ is methyl.

In certain instances of any one of the formulae described herein, one or more of the co-monomers is substituted with a WSG that is independently selected from one of the following structures:

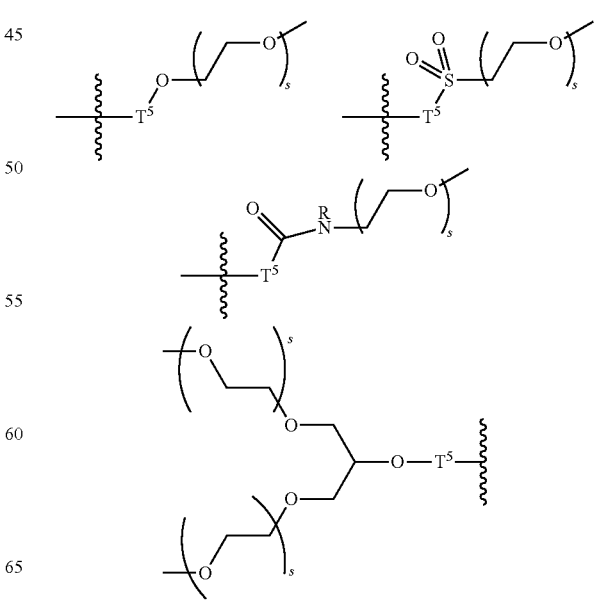

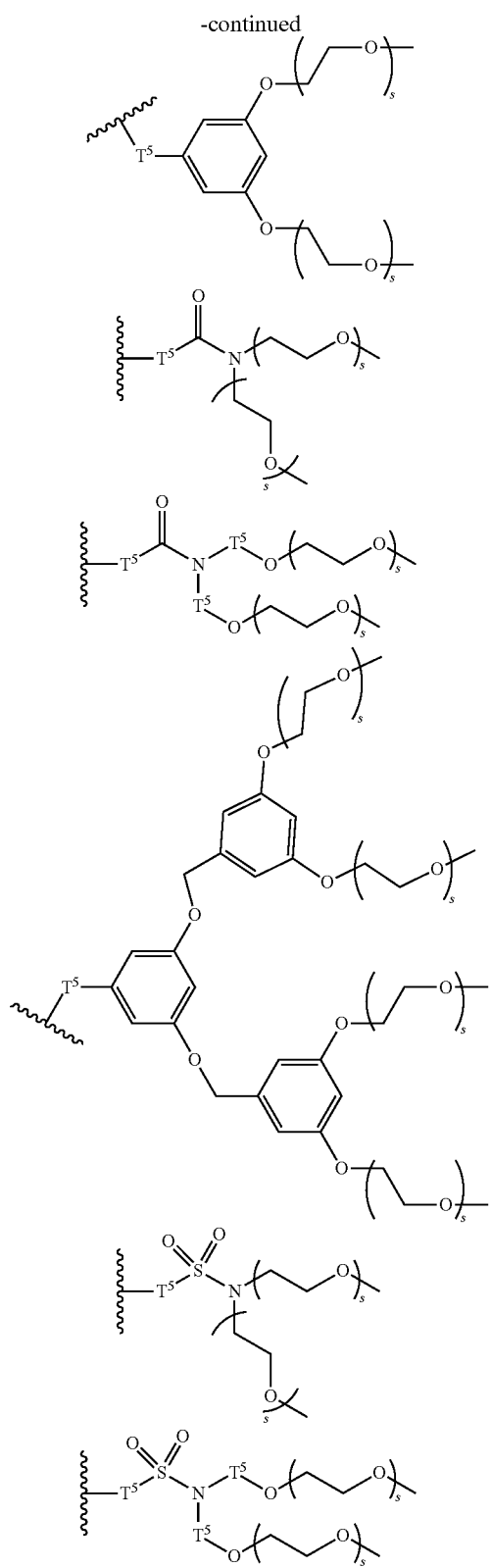

8, 9, 10, 11 or 12. In some cases, each s of the WSG is 3. In some cases, each s of the WSG is 4. In some cases, each s of the WSG is 5. In some cases, each s is 6. In some cases, each s of the WSG is 7. In some cases, each s of the WSG is 8. In some cases, each s of the WSG is 9. In some cases, each s of the WSG is 10. In some cases, each s of the WSG is 11. In some cases, each s of the WSG is 12. In some cases, each s of the WSG is 14. In some cases, each s of the WSG is 16. In some embodiments, $T^5$ is an alkyl linker, such as a C1-C12 or C1-C6 alkyl linker. In some embodiments, $T^5$ is a substituted alkyl linker. In some embodiments, $T^5$ is an alkoxy linker (e.g., —O-alkyl-). In some embodiments, $T^5$ is a substituted alkoxy. It is understood that hydroxy-terminated PEG chains instead of methoxy-terminated PEG chains may be utilized in any of the WSG groups described above. In certain instances of any one of the formulae described herein, one or more of the co-monomers is substituted with a WSG that is a dendron selected from one of the following structures:

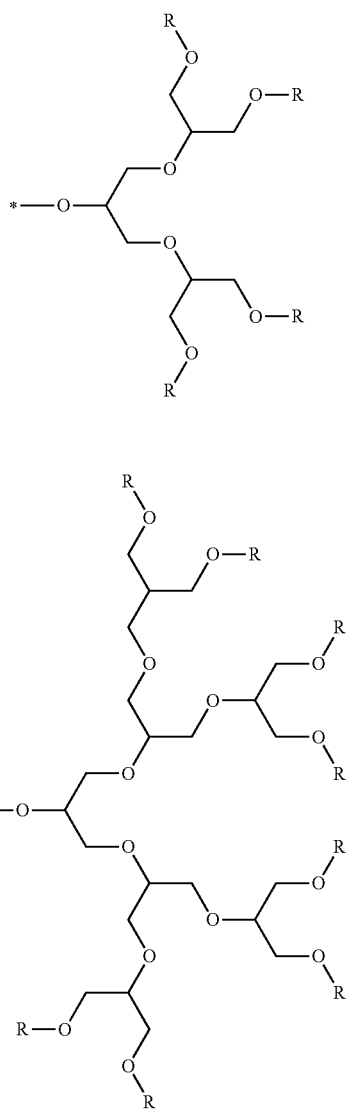

wherein: $T^5$ is an optional linker; and each s is an integer from 1 to 50. In certain instances of the WSG, $T^5$ is absent. In certain instances, each s of the WSG is independently 1 to 20, such as 3 to 20, 3 to 15, 3 to 12, or 6 to 12. In certain cases, each s of the WSG is independently 1, 2, 3, 4, 5, 6, 7,

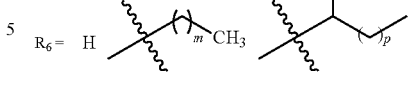

m,p = 0-10.

In certain instances of any one of the formulae described herein, one or more of the co-monomers is substituted with WSG that is an oxazoline of the following structure:

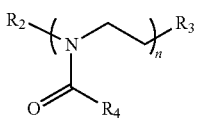

n = 1-50

$R_2$, $R_4$=

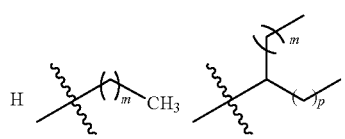

m,p = 0-10

$R_3$=

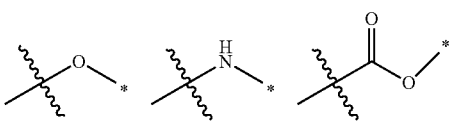

In certain instances of any one of the formulae described herein, one or more of the co-monomers is substituted with a WSG that is a peptoid selected from one of the following structures:

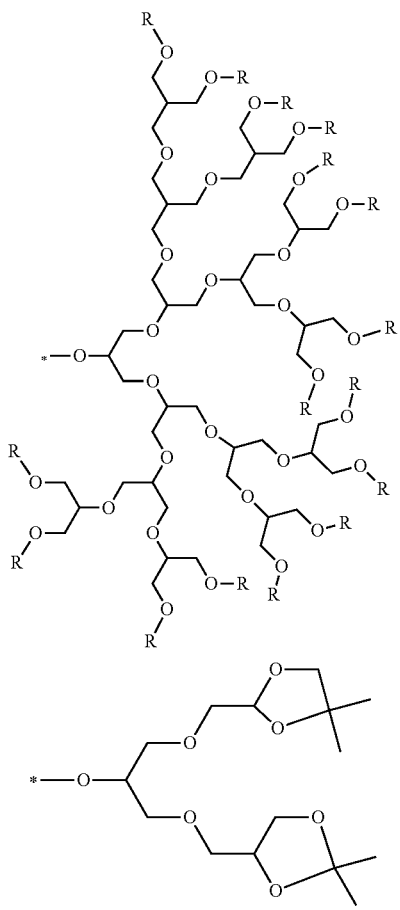

(and higher generations)

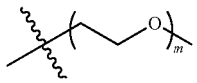

where R = H, CH$_3$
m = 1-16

In certain instances of any one of the formulae described herein, one or more of the co-monomers is substituted with a WSG that is a polyol selected from one of the following structures:

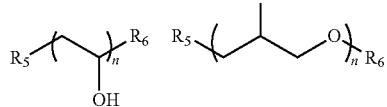

n = 1-50

$R_5$ = 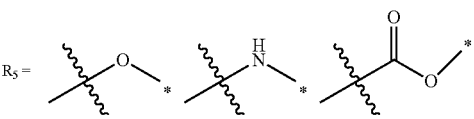

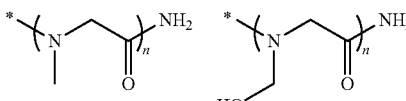

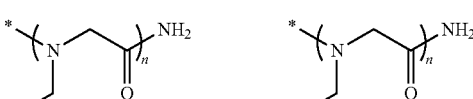

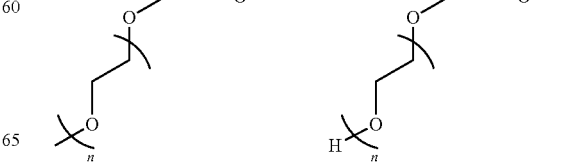

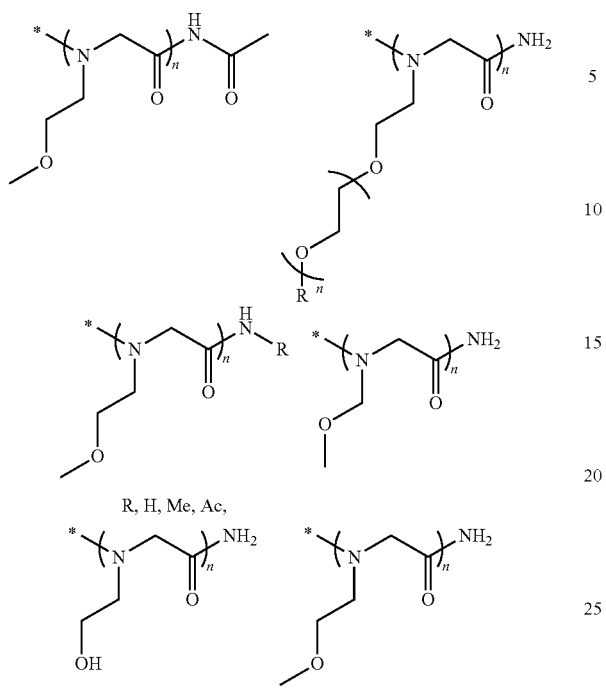

R, H, Me, Ac,

Polymeric Dyes

Further details of the subject polymeric dyes are provided in the exemplary formula below. In some embodiments, the subject polymeric dye has the structure of formula (I):

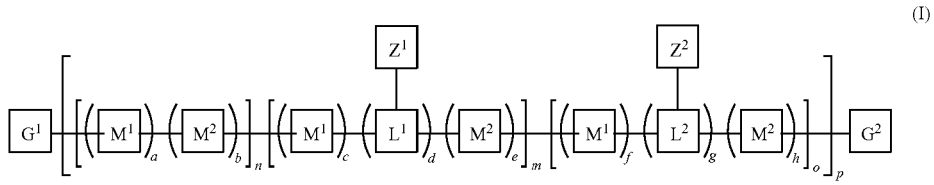

(I)

wherein:

each $M^1$ is independently selected from a substituted or unsubstituted aryl co-monomer, a substituted or unsubstituted heteroaryl co-monomer, an alkynyl co-monomer and a substituted or unsubstituted alkenyl co-monomer (e.g., as described herein);

each $M^2$ is independently a conjugation-modifying repeat unit (e.g., as described herein);

$L^1$ and $L^2$ are each independently a linker unit;

$Z^1$ is a linked chemoselective tag or a linked signaling chromophore ($—Z^1$);

$Z^2$ is a branched π-conjugated segment;

a-h are each independently 0 or 1, wherein a+b≥1 and b+e+h≥1;

n is from 1 to 10,000;

m and o are each independently from 0 to 10,000;

p is from 1 to 100,000; and $G^1$ and $G^2$ are independently selected from a terminal group, a π-conjugated segment, a linker and a linked specific binding member. In certain instances of formula (I), m is 0. In certain instances of formula (I), m is 1 to 10,000, such as 1 to 1000, 1 to 100, or 1 to 10. In certain instances of formula (I), o is 0. In certain instances of formula (I), o is 1 to 10,000, such as 1 to 1000, 1 to 100, or 1 to 10. In certain instances of formula (I), d is 1. In certain instances of formula (I), g is 1. In certain instances of formula (I), a+b=2.

In some embodiments of formula (I), $M^2$ is a conjugation-modifying repeat unit of formula (XI) (e.g., as described herein). As such, in some embodiments of formula (I), the subject polymeric dye has the structure of formula (II):

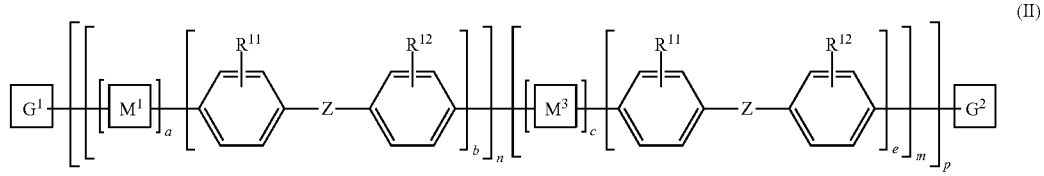

(II)

wherein:

M¹ and M³ are independently selected from an aryl co-monomer, a heteroaryl co-monomer, an alkynyl co-monomer and an alkenyl co-monomer, each substituted or unsubstituted;

Z is selected from a covalent bond, a saturated atom or group and a functional group;

$R^{11}$ and $R^{12}$ are each independently selected from H, alkyl, substituted alkyl, alkoxy, substituted alkoxy, hydroxy, cyano, halogen, sulfonate, sulfonamide, substituted sulfonamide, carboxy, carboxyamide, substituted carboxyamide and a water solubilizing group;

a, b, c and e are each independently 0 or 1, wherein a+b≥1 and c+e≥1.

In certain instances of formula (II), m is 0. In certain instances of formula (II), m is 1 to 10,000, such as 1 to 1000, 1 to 100, or 1 to 10. In certain instances of formula (II), a is 0. In certain instances of formula (II), a is 1. In certain instances of formula (II), b is 1. In certain instances of formula (II), c is 0. In certain instances of formula (II), e is 1. In certain instances of formula (II), c is 1. In certain instances of formula (II), a+b=2. In certain instances of formula (II), b+e=2. In certain instances of formula (II), a+c=0.

In some embodiments of formula (I), the subject polymeric dye has the structure of formula (III):

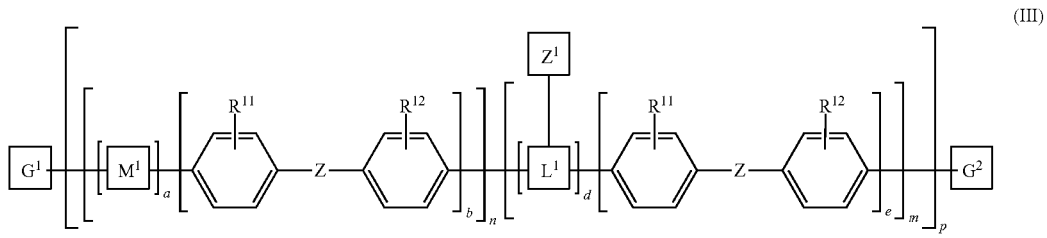

(III)

wherein:

$L^1$ is a linker unit comprising an aryl co-monomer, a heteroaryl co-monomer, an alkynyl co-monomer and an alkenyl co-monomer (e.g., as described herein);

$Z^1$ is a linked chemoselective tag or a linked signaling chromophore;

Z is selected from a covalent bond, a saturated atom or group and a functional group (e.g., as described herein);

$R^{11}$ and $R^{12}$ are each independently selected from H, alkyl, substituted alkyl, alkoxy, substituted alkoxy, hydroxy, cyano, halogen, sulfonate, sulfonamide, substituted sulfonamide, carboxy, carboxyamide, substituted carboxyamide and a water solubilizing group;

a, b, d and e are each independently 0 or 1, wherein a+b≥1 and d+e≥1.

In certain instances of formula (III), m is 0. In certain instances of formula (III), n is 1 to 10,000, such as 1 to 1000, 1 to 100, or 1 to 10. In certain instances of formula (III), m is 1 to 10,000, such as 1 to 1000, 1 to 100, or 1 to 10. In certain instances of formula (III), a is 1. In certain instances of formula (III), b is 1. In certain instances of formula (III), d is 1. In certain instances of formula (III), e is 1. In certain instances of formula (III), a+b=2.

In certain instances of formula (III), $Z^1$ is a linked chemoselective tag. In certain instances of formula (III), $Z^1$ is a linked signaling chromophore, and the polymeric dye can be referred to as a polymeric tandem dye.

Also provided are polymeric dyes that include a branching point in the conjugated polymer backbone, to which a pi-conjugated segment of co-monomers can be linked. This branched pi-conjugated segment of co-monomers can be pi-conjugated to the main backbone of the polymer, or can be separated from the backbone, e.g., via a conjugation-modifying repeat unit. In some embodiments of formula (I), the subject polymeric dye has the structure of formula (I), wherein a, b, g and h are each 1; and $Z^2$ has is a branched π-conjugated segment of formula (IV):

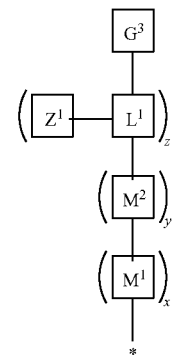

(IV)

wherein $M^1$, $M^2$, $L^1$, $Z^1$ are as defined for formula (I); and $G^3$ is a terminal group, a π-conjugated segment, a linker or a linked specific binding member. In certain instances, the polymeric dye is of formula (I) wherein a, b, d, e, g, h are each 1; and $Z^1$ is a linked functional signaling chromophore.

In some embodiments of formula (I), the subject polymeric dye has the structure of formula (V):

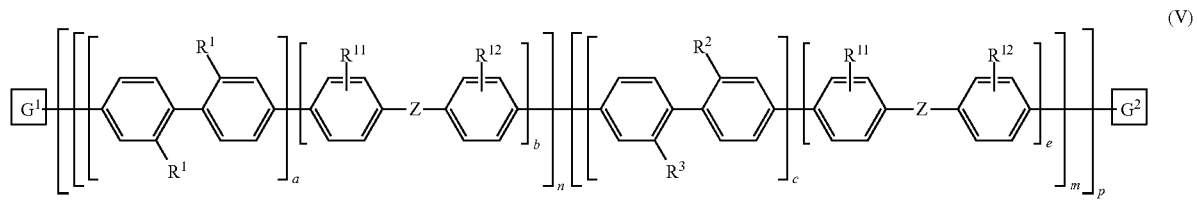

(V)

wherein

Z is selected from a covalent bond, a saturated atom or group and a functional group (e.g., as described herein);

$R^1$-$R^3$, $R^{11}$ and $R^{12}$ are each independently selected from H, alkyl, substituted alkyl, alkoxy, substituted alkoxy, hydroxy, cyano, halogen, sulfonate, sulfonamide, substituted sulfonamide, carboxy, carboxyamide, substituted carboxyamide, a water solubilizing group, a linked chemoselective tag and a linked signalling chromophore;

a, b, c and e are each independently 0 or 1, wherein a+b≥1 and c+d≥1;

n is from 1 to 10,000;

m is from 0 to 10,000;

p is from 1 to 10,000; and $G^1$ and $G^2$ are independently selected from a terminal group, a π-conjugated segment, a linker and a linked specific binding member. In certain instances of formula (V), $R^1$-$R^3$ are each independently a water solubilizing group; and $R^2$ and $R^3$ are the same.

In certain instances of formula (V), $R^1$ and $R^2$ are each independently a water solubilizing group; and $R^3$ is a linked chemoselective tag or a linked signalling chromophore. In certain instances of formula (V), m is 0. In certain instances of formula (V), n is 1 to 10,000, such as 1 to 1000, 1 to 100, or 1 to 10. In certain instances of formula (V), n is 2 to 10,000, such as 2 to 1000, 2 to 100, or 2 to 10. In certain instances of formula (V), m is 1 to 10,000, such as 1 to 1000, 1 to 100, or 1 to 10. In certain instances of formula (V), m is 2 to 10,000, such as 2 to 1000, 2 to 100, or 2 to 10. In certain instances of formula (V), a is 1. In certain instances of formula (V), b is 1. In certain instances of formula (V), c is 1. In certain instances of formula (V), e is 1. In certain instances of formula (V), a+b=2. Any convenient embodiments of the Z groups of a conjugation-modifying repeat unit described herein can be utilized in a polymeric dye of formula (V). Any convenient embodiments of the WSG described herein can be utilized as $R^1$-$R^3$, $R^{11}$ and $R^{12}$ groups in a polymeric dye of formula (V).

In certain instances of formula (V), the subject polymeric dye has the formula (VI):

Z is selected from —S—, —S(O)—, —SO$_2$—, —SO$_2$NR'—, —S(O)O—, —O—, —C(O)—, —C(O)NR'—, —C(O)O—, —OC(O)NR'—, —OC(O)O—, —NR'C(O)NR'—, —C(R$^5$)(R$^6$)—, —Si(R$^5$)(R$^6$)—, —N(R')—, an alkyl linker (e.g., $C_2$-$C_{12}$, such as $C_2$-$C_6$ substituted or unsubstituted alkyl linker) and a polyethylene glycol linker;

each R', $R^5$ and $R^6$ is independently selected from H, alkyl, substituted alkyl, and wherein $R^5$ and/or $R^6$ is optionally cyclically linked to $R^{12}$ or $R^{12}$ to provide a benzo-fused carbocycle or heterocycle ring; and x and y represent mol % values. In some cases, y is 1-25 mol % and x is 99 mol % or less.

In certain instances of formula (VI), Z is selected from —S—, —S(O)—, —SO$_2$—, —O—, —C(O)—, —C(O)NR'—, —OC(O)NR'—, —OC(O)O— and —NR'C(O)NR'—. In certain cases of formula (VI), Z is —SO$_2$—. In some instances of formula (VI), Z is C(R$^5$)(R$^6$)— or —Si(R$^5$)(R$^6$)—. In some instances of formula (VI), each WSG$^1$ and WSG$^2$ are each independently a water solubilizing group selected from:

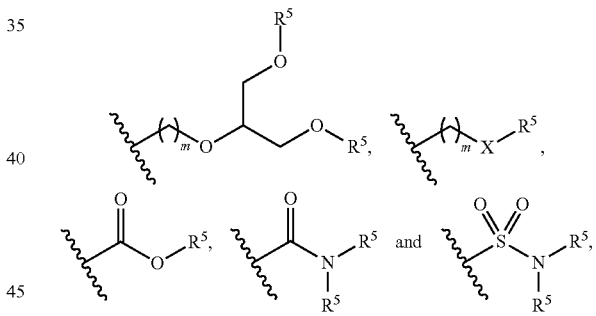

wherein m is 0-10 (such as 1-6, e.g., 1, 2, 3, 4, 5 or 6) and each R$^5$ is independently —(CH$_2$CH$_2$O)$_p$R' wherein p is an integer from 0 to 50 (such as 6-50, 6-40, 6-30, 8-30, 10-30

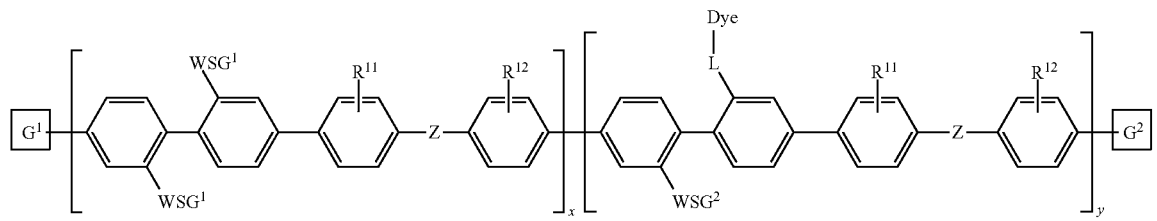

Figure 3:
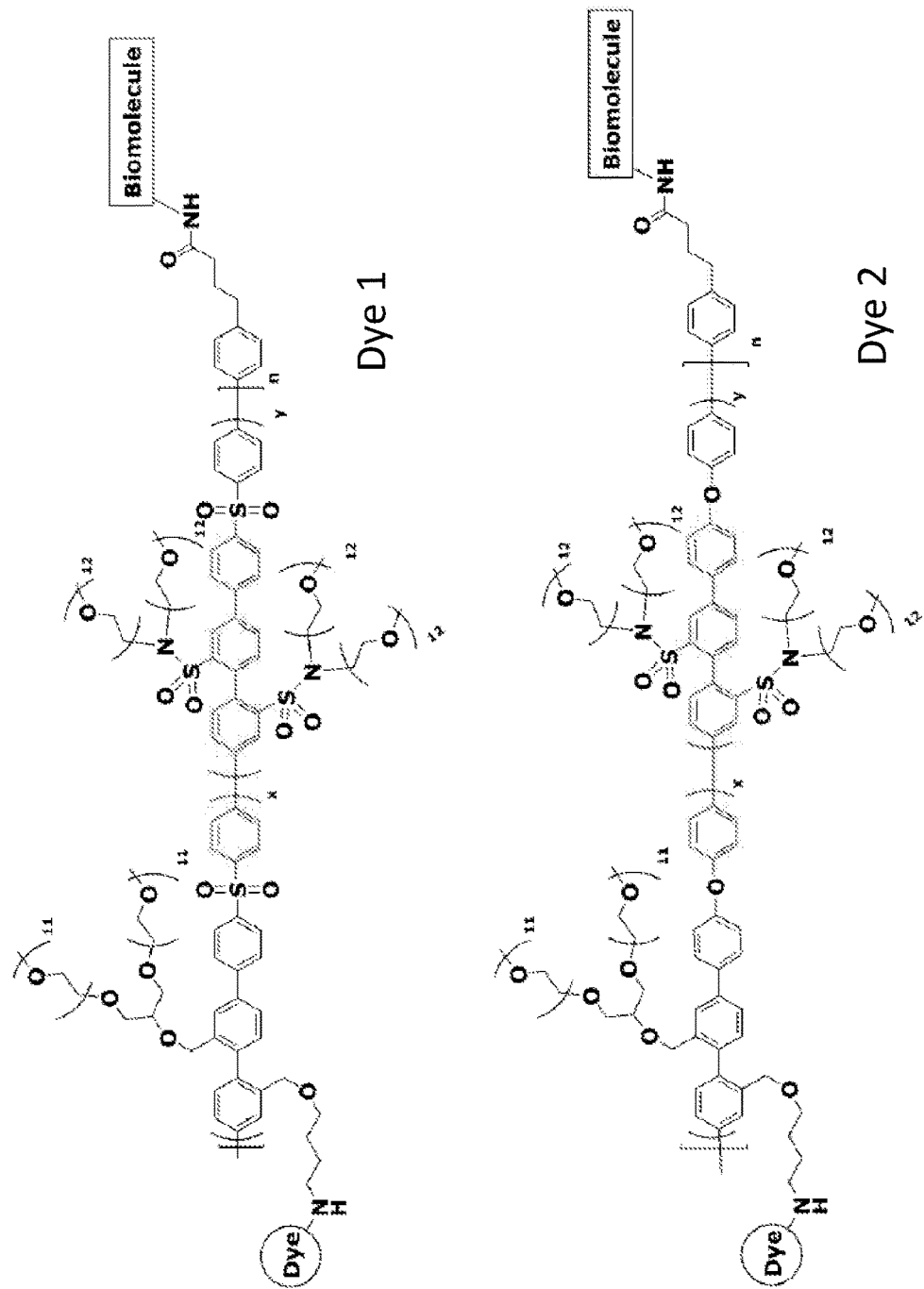
FIG. 3 depicts exemplary polymeric dyes of the present disclosure.
Figure 6A:
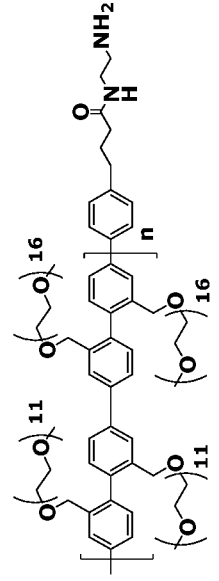
FIG. 6A-6C depict exemplary polymeric dyes of the present disclosure.
Figure 6B:
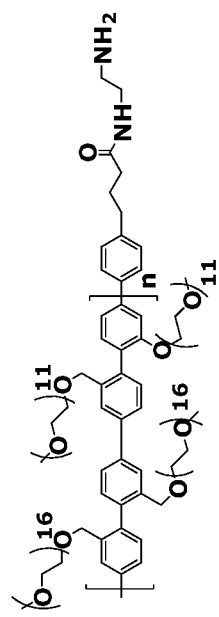
Figure 6C:
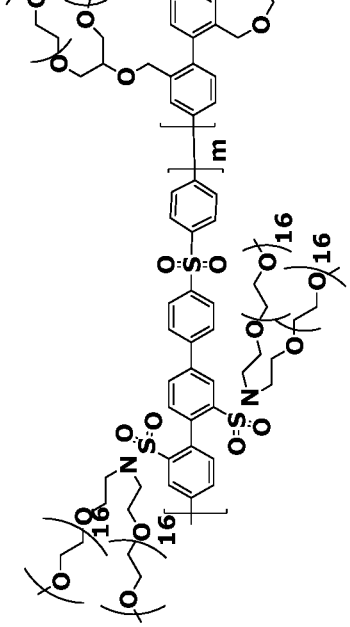

(VI)

wherein:

Dye is the linked signaling chromophore and L is a linker; WSG1 and WSG2 are each independently a water solubilizing group (WSG) (e.g., as described herein);

or 10-20, e.g., 10, 11, 12, 13, 14, 15, 16, 17, 18, 19 or 20) and R' is H, an alkyl or a substituted alkyl; and X is O. FIGS. 3 and 6C show exemplary polymeric dyes of formula (V) and (VI).

In certain instances of formula (V), the subject polymeric dye has the formula (VII):

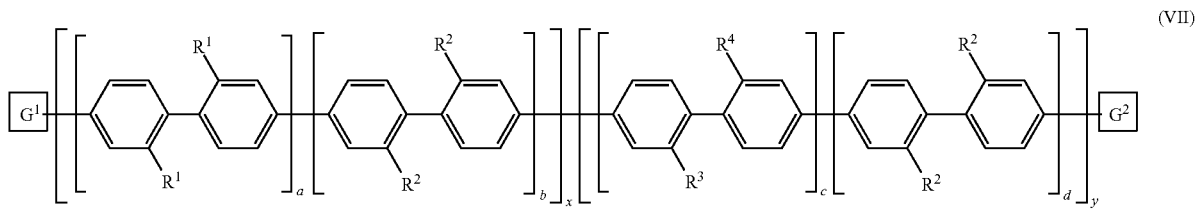

wherein:

$R^1$-$R^4$ are each independently selected from H, alkyl, substituted alkyl, alkoxy, substituted alkoxy, hydroxy, cyano, halogen, sulfonate, sulfonamide, substituted sulfonamide, carboxy, carboxyamide, substituted carboxyamide, a water solubilizing group (WSG) (e.g., as described herein), a linked chemoselective tag and a linked signalling chromophore;

a, b, c and e are each independently 0 or 1, wherein a+b≥1 and c+d≥1;

x and y represent mol % values;

p is from 1 to 10,000; and $G^1$ and $G^2$ are independently selected from a terminal group, a π-conjugated segment, a linker and a linked specific binding member. In certain instances of formula (VII), $R^1$-$R^3$ are each independently a water solubilizing group; and $R^2$ and $R^3$ are the same. In certain instances of formula (VII), $R^3$ or $R^4$ is a linked chemoselective tag or linked signalling chromophore. In some cases, y is 1-25 mol % and x is 99 mol % or less.

Figure 4:
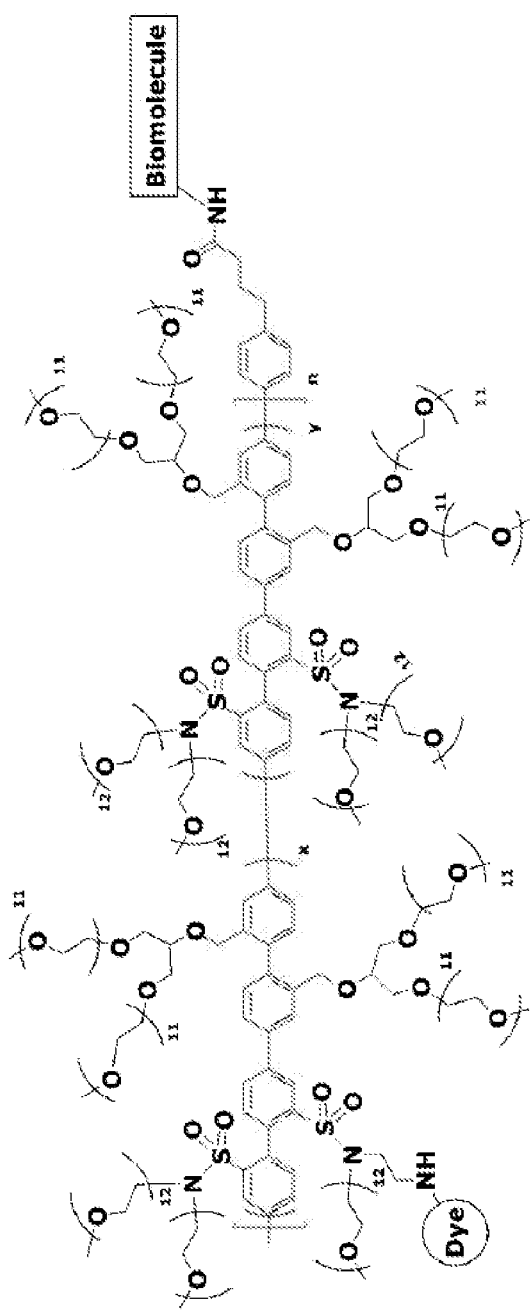
FIG. 4 depicts an exemplary polymeric dye of the present disclosure.
Figure 5:
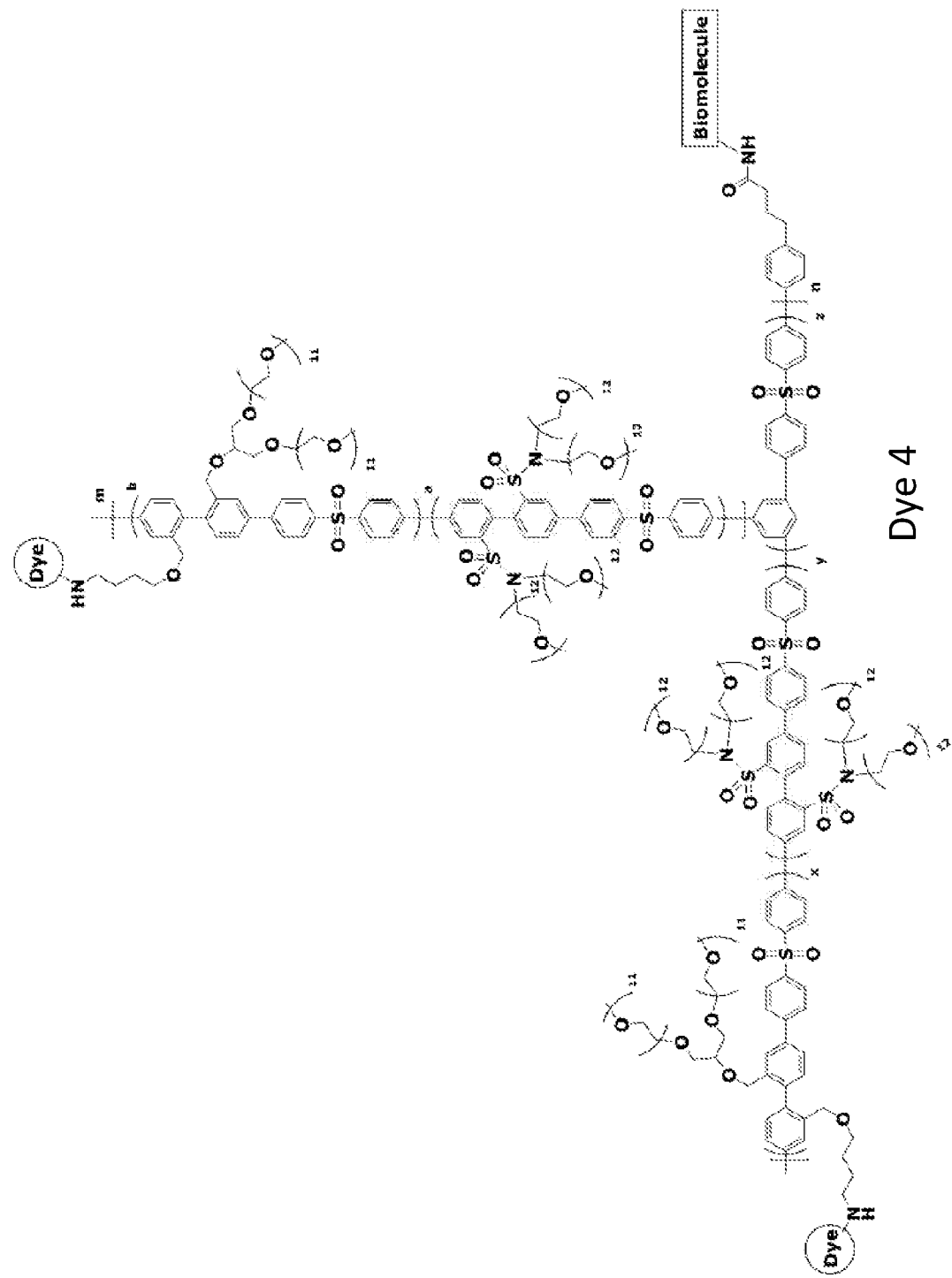
FIG. 5 depicts an exemplary polymeric dye of the present disclosure that includes a branched π-conjugated segment.

In certain instances of formula (V), the subject polymeric dye has the formula (VIII):

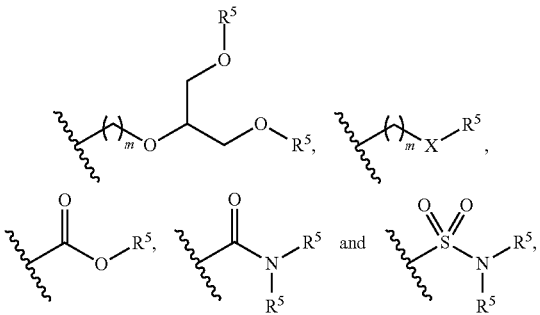

wherein m is 0-10 (such as 1-6, e.g., 1, 2, 3, 4, 5 or 6) and each $R^5$ is independently —$(CH_2CH_2O)_pR'$ wherein p is an integer from 0 to 50 (such as 6-50, 6-40, 6-30, 8-30, 10-30 or 10-20, e.g., 10, 11, 12, 13, 14, 15, 16, 17, 18, 19 or 20) and R' is H, an alkyl or a substituted alkyl; and X is O. FIGS. 4 and 6A-B show exemplary polymeric dyes of formula (V), (VII) and (VIII).

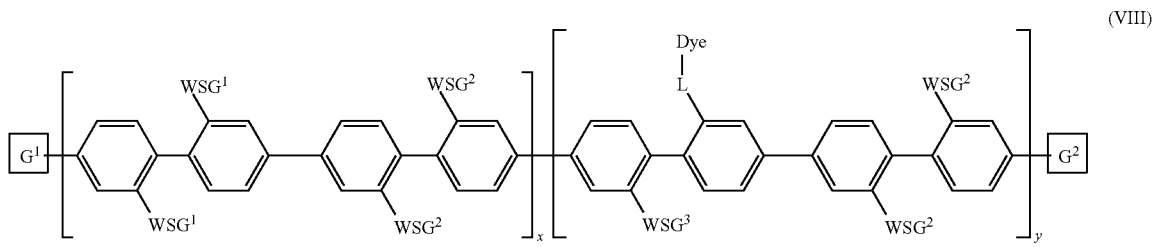

wherein:

Dye is the linked signaling chromophore and L is a linker; each WSG1, each WSG2 and WSG3 are each independently a water solubilizing group (WSG) (e.g., as described herein); and x and y represent mol % values. In some cases, y is 1-25 mol % and x is 99 mol % or less.

In certain instances of formula (VIII), WSG1, each WSG2 and WSG3 are independently a water solubilizing group selected from:

Polymeric Tandem Dyes

The water soluble light harvesting multichromophore can itself be fluorescent and capable of transferring energy to a linked acceptor signaling chromophore. As such, the subject polymeric tandem dyes further include a covalently linked acceptor signaling chromophore in energy-receiving proximity to the donor water solvated light harvesting multichromophore. As such, excitation of the multichromophore donor leads to energy transfer to and emission from the covalently attached acceptor signaling chromophore. The number of signaling chromophore acceptor units that are linked to the donor water solvated light harvesting multichromophore may vary, where in some instances the number ranges from 1 mol % to 50 mol %, such as from 5 mol % to 25 mol % or from 10 mol % to 25 mol %.

Mechanisms for energy transfer from the fluorescent water solvated light harvesting multichromophore donor to the linked acceptor signaling chromophore include, for example, resonant energy transfer (e.g., Forster (or fluorescence) resonance energy transfer, FRET), quantum charge exchange (Dexter energy transfer) and the like. In some instances, these energy transfer mechanisms are relatively short range; that is, close proximity of the light harvesting multichromophore system to the acceptor provides for efficient energy transfer. In some instances, under conditions for efficient energy transfer, amplification of the emission from the acceptor occurs where the emission from the luminescent signaling chromophore is more intense when the incident light (the "pump light") is at a wavelength which is absorbed by the light harvesting multichromophore than when the luminescent signaling chromophore is directly excited by the pump light.

By "efficient" energy transfer is meant 10% or more, such as 20% or more or 30% or more, of the energy harvested by the donor is transferred to the acceptor. By "amplification" is meant that the signal from the signaling chromophore is 1.5× or greater when excited by energy transfer from the donor light harvesting multichromophore as compared to direct excitation with incident light of an equivalent intensity. The signal may be measured using any convenient method. In some cases, the 1.5× or greater signal refers to an intensity of emitted light. In certain cases, the 1.5× or greater signal refers to an increased signal to noise ratio. In certain embodiments of the polymeric tandem dye, the signaling chromophore emission is 1.5 fold greater or more when excited by the multichromophore as compared to direct excitation of the signaling chromophore with incident light, such as 2-fold or greater, 3-fold or greater, 4-fold or greater, 5-fold or greater, 6-fold or greater, 8-fold or greater, 10-fold or greater, 20-fold or greater, 50-fold or greater, 100-fold or greater, or even greater as compared to direct excitation of the signaling chromophore with incident light.

The linked luminescent signaling chromophore emission of the polymeric tandem dye can have a quantum yield of 0.03 or more, such as a quantum yield of 0.04 or more, 0.05 or more, 0.06 or more, 0.07 or more, 0.08 or more, 0.09 or more, 0.1 or more, 0.15 or more, 0.2 or more, 0.3 or more or even more. In some instances, the polymeric tandem dye has an extinction coefficient of $5 \times 10^5$ cm$^{-1}$M$^{-1}$ or more, such as $6 \times 10^5$ cm$^{-1}$M$^{-1}$ or more, $7 \times 10^5$ cm$^{-1}$M$^{-1}$ or more, $8 \times 10^5$ cm$^{-1}$M$^{-1}$ or more, $9 \times 10^5$ cm$^{-1}$M$^{-1}$ or more, such as $1 \times 10^6$ cm$^{-1}$M$^{-1}$ or more, $1.5 \times 10^6$ cm$^{-1}$M$^{-1}$ or more, $2 \times 10^6$ cm$^{-1}$M$^{-1}$ or more, $2.5 \times 10^6$ cm$^{-1}$M$^{-1}$ or more, $3 \times 10^6$ cm$^{-1}$M$^{-1}$ or more, $4 \times 10^6$ cm$^{-1}$M$^{-1}$ or more, $5 \times 10^6$ cm$^{-1}$M$^{-1}$ or more, $6 \times 10^6$ cm$^{-1}$M$^{-1}$ or more, $7 \times 10^6$ cm$^{-1}$M$^{-1}$ or more, or $8 \times 10^6$ cm$^{-1}$M$^{-1}$ or more. In some embodiments, the polymeric tandem dye has a molar extinction coefficient of $5 \times 10^5$ M$^{-1}$cm$^{-1}$ or more. In certain embodiments, the polymeric tandem dye has a molar extinction coefficient of $1 \times 10^6$ M$^{-1}$cm$^{-1}$ or more.

The subject polymeric tandem dyes provide for fluorescence emissions from luminescent signaling chromophore dyes that are brighter than the emissions which are possible from such luminescent dyes in isolation. The linked luminescent signaling chromophore emission of the polymeric tandem dye can have a brightness of 50 mM$^{-1}$cm$^{-1}$ or more, such as 60 mM$^{-1}$cm$^{-1}$ or more, 70 mM$^{-1}$cm$^{-1}$ or more, 80 mM$^{-1}$cm$^{-1}$ or more, 90 mM$^{-1}$cm$^{-1}$ or more, 100 mM$^{-1}$cm$^{-1}$ or more, 150 mM$^{-1}$cm$^{-1}$ or more, 200 mM$^{-1}$cm$^{-1}$ or more, 250 mM$^{-1}$cm$^{-1}$ or more, 300 mM$^{-1}$cm$^{-1}$ or more, or even more. In certain instances, the linked signaling chromophore emission of the polymeric tandem dye has a brightness that is at least 5-fold greater than the brightness of a directly excited luminescent dye, such as at least 10-fold greater, at least 20-fold greater, at least 30-fold greater, at least 50-fold greater, at least 100-fold greater, at least 300-fold greater, or even greater than the brightness of a directly excited luminescent dye.

In some embodiments, a polymeric tandem dye includes: a water solvated polymeric dye having a deep ultraviolet excitation spectrum and comprising a segment of π-conjugated co-monomers and a conjugation-modifying repeat unit; and a signaling chromophore covalently linked to the multichromophore in energy-receiving proximity therewith.

In certain embodiments or the formulae described herein, e.g., formulae (I) and (III), a linked signaling chromophore (e.g., as described herein) is included as a substituent of a co-monomer. Any convenient signaling chromophore can be attached to any convenient polymer dye described herein via coupling of compatible chemoselective functional groups. The signaling chromophore can be selected to provide for a desirable emission spectra and emission maximum wavelength.

As used herein, the terms "chemoselective functional group" and "chemoselective tag" are used interchangeably and refer to a functional group that can selectively react with another compatible functional group to form a covalent bond, in some cases, after optional activation of one of the functional groups. Chemoselective functional groups of interest include, but are not limited to, thiols and maleimide or iodoacetamide, amines and carboxylic acids or active esters thereof, as well as groups that can react with one another via Click chemistry, e.g., azide and alkyne groups (e.g., cyclooctyne groups), as well as hydroxyl, hydrazido, hydrazino, aldehyde, ketone, azido, alkyne, phosphine, epoxide, and the like.

Any convenient linking co-monomers may be incorporated into the subject multichromophores to provide for a linking group to which may be attached any convenient moieties of interest (e.g., a linked signaling chromophore). Linking co-monomers of interest include, but are not limited to, those co-monomers described in the formulae herein, and a fluorene co-monomer, a phenylenevinylene co-monomer, a phenyleneethynylene co-monomer, a carbazole co-monomer, a $C_2$-$C_{12}$ alkyne co-monomer, an arylene-ethynylene co-monomer, a heteroarylene-ethynylene co-monomer, an arylene co-monomer and a heteroarylene co-monomer. As used herein, the terms aryl or heteroaryl co-monomer and arylene or heteroarylene co-monomer are used interchangeably. In certain cases, the linking co-monomer is a substituted aryl co-monomer. In certain cases, the linking co-monomer is a substituted heteroaryl co-monomer. In certain cases, the linking co-monomer is a substituted or unsubstituted 1,4-phenyl, a substituted or unsubstituted 1,3-phenyl, a substituted or unsubstituted 4,4'-biphenyl, a substituted or unsubstituted 2,5-pyridyl, and a substituted or unsubstituted 2,6-pyridyl.

In some instances of any of the formula described herein, the signaling chromophore is linked to a co-monomer comprising 1% to 50% by molarity of the multichromophore, such as 1% to 20%, 1% to 10%, or 11 to 20% by molarity. In certain cases, the multichromophore is a conjugated polymer comprising 5 or more repeat units.

Any convenient chemoselective functional groups may be included in the subject multichromophores (e.g., at the —Z$^1$, —Z$^2$ and/or in the G$^1$ or G$^2$ terminal groups, including, but are not limited to, carboxylic acid, active ester (e.g., NHS or sulfo-NHS ester), amino, hydroxyl, thiol, maleimide, iodoacetyl, hydrazido, hydrazino, aldehyde, ketone, azido, alkyne, phosphine and epoxide. It is understood that in the polymeric tandem dye structures described herein, in some cases, the groups $Z^1$ and $Z^2$ appear at a equivalent position in the structure where these groups can be used interchangeably to refer to either a linked signaling chromophore or a chemoselective functional group that is capable of subsequent conjugation to a convenient chromophore precursor to produce the linked signaling chromophore.

In some cases, the signaling chromophore is a fluorophore. In certain cases, the signaling chromophore is a quencher. Any convenient fluorescent dyes may be utilized in the polymeric tandem dyes as an acceptor chromophore. The terms "fluorescent dye" and "fluorophore" are used interchangeably herein. The signaling chromophore ($Z^1$) can be a dye molecule selected from a rhodamine, a coumarin, a xanthene, a cyanine, a polymethine, a pyrene, a dipyrromethene borondifluoride, a napthalimide, a phycobiliprotein, a peridinum chlorophyll protein, conjugates thereof, and combinations thereof. In certain embodiments, the signaling chromophore ($Z^1$) is a cyanine dye, a xanthene dye, a coumarin dye, a thiazine dye and an acridine dye. In some instances, the signaling chromophore ($Z^1$) is selected from DY 431, DY 485XL, DY 500XL, DY 610, DY 640, DY 654, DY 682, DY 700, DY 701, DY 704, DY 730, DY 731, DY 732, DY 734, DY 752, DY 778, DY 782, DY 800, DY 831, Biotium CF 555, Cy 3.5 and diethylamino coumarin. In some embodiments, the acceptor chromophore is a cyanine dye, a xanthene dye, a coumarin dye, a thiazine dye or an acridine dye. Fluorescent dyes of interest include, but are not limited to, fluorescein, 6-FAM, rhodamine, Texas Red, tetramethylrhodamine, carboxyrhodamine, carboxyrhodamine 6G, carboxyrhodol, carboxyrhodamine 110, Cascade Blue, Cascade Yellow, coumarin, Cy2, Cy3, Cy3.5, Cy5, Cy5.5, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, Alexa Fluor 700, 7-amino-4-methylcoumarin-3-acetic acid, BODIPY FL, BODIPY FL-Br.sub.2, BODIPY 530/550, BODIPY 558/568, BODIPY 564/570, BODIPY 576/589, BODIPY 581/591, BODIPY 630/650, BODIPY 650/665, BODIPY R6G, BODIPY TMR, BODIPY TR, conjugates thereof, and combinations thereof. Lanthanide chelates of interest include, but are not limited to, europium chelates, terbium chelates and samarium chelates. In some embodiments, the polymeric tandem dye includes a polymeric dye linked to an acceptor fluorophore selected from Cy3, Cy3.5, Cy5, Cy5.5, Cy7, Alexa488, Alexa 647 and Alexa700. In certain embodiments, the polymeric tandem dye includes a polymeric dye linked to an acceptor fluorophore selected from Dyomics dyes (such as DY 431, DY 485XL, DY 500XL, DY 530, DY 610, DY 633, DY 640, DY 651, DY 654, DY 682, DY 700, DY 701, DY 704, DY 730, DY 731, DY 732, DY 734, DY 752, DY 754, DY 778, DY 782, DY 800 or DY 831), Biotium CF 555, Cy 3.5, and diethylamino coumarin.

In some embodiments, the signaling chromophore that is selected has an emission maximum wavelength in the range of 300 to 900 nm, such as 350 to 850 nm, 350 to 600 nm, 360 to 500 nm, 370 to 500 nm, 380 to 500 nm, 390 to 500 nm or 400 to 500 nm, where specific examples of emission maxima of signaling chromophore of interest include, but are not limited to: 395 nm±5 nm, 420 nm±5 nm, 430 nm±5 nm, 440 nm±5 nm, 450 nm±5 nm, 460 nm±5 nm, 470 nm±5 nm, 480 nm±5 nm, 490 nm±5 nm, 500 nm±5 nm, 510 nm±5 nm, 520 nm±5 nm, 530 nm±5 nm, 540 nm±5 nm, 550 nm±5 nm, 560 nm±5 nm, 570 nm±5 nm, 580 nm±5 nm, 590 nm±5 nm, 605 nm±5 nm, 650 nm±5 nm, 680 nm±5 nm, 700 nm±5 nm, 805 nm±5 nm.

End Groups

Any convenient end groups (e.g., $G^1$ and $G^2$) may be utilized at the terminals of the subject multichromophores. As used herein, the terms "end group" and "terminal group" are used interchangeably to refer to the groups located at the terminals of the polymeric structure of the multichromophore, e.g., as described herein. $G^1$ and $G^2$ groups of interest include, but are not limited to a terminal capping group, a π conjugated segment, a linker and a linked specific binding member. In some embodiments, a terminal capping groups is a monovalent group which is conjugated to the backbone of the multichromophore after polymerization. In certain instances, the terminal capping group is an aryl, a substituted aryl, a heteroaryl, a substituted heteroaryl, an alkyl or a substituted alkyl. In some cases, the terminal co-monomer is directed linked to a chemoselective tag or linker. In certain cases, the terminal capping group is derived from a monomer used in the method of polymerization, e.g., a terminal group such as a halogen (e.g., Br), a boronic acid or a boronic ester, which is capable of undergoing further conjugation. In some instances, $G^1$ and/or $G^2$ is a π conjugated segment. As used herein, a π conjugated segment refers to any convenient segment of a conjugated polymer to which the multichromophore may be conjugated, i.e., allowing delocalization of pi electron across adjacent units. In certain embodiments, $G^1$ and/or $G^2$ is a linker, such as a linker including a functional group suitable for conjugation to a specific binding moiety. It is understood that linkers located at the $G^1$ and/or $G^2$ positions of the multichromophore may be selected so as to be orthogonal to any other linkers including chemoselective tags (e.g., as described herein) that may be present at a sidechain of the multichromophore (e.g., at $Z^2$). In certain embodiments, an amino functional group or derivative thereof is included at $G^1$ and/or $G^2$ and a carboxylic acid functional group or derivative thereof is included at $Z^2$. In certain embodiments, a carboxylic acid functional group or derivative thereof is included at $G^1$ and/or $G^2$ and an amino functional group or derivative thereof is included at $Z^2$.

In some embodiments of the formulae described herein, at least one of $G^1$ and $G^2$ is -$L^3$-$Z^4$ where $L^3$ is a linker (e.g., as described herein) and $Z^4$ is a specific binding member (e.g., as described herein). In some embodiments of formulae described herein, at least one of $G^1$ and $G^2$ is -$L^3$-$Z^3$ where $L^3$ is a linker (e.g., as described herein) and $Z^3$ is a chemoselective tag (e.g., as described herein). Any convenient chemoselective tag and conjugation chemistries can be adapted for use in the subject multichromophores. Chemoselective tags of interest include, but are not limited to, amine, active ester, maleimide, thiol, sulfur(VI) fluoride exchange chemistry (SuFEX), sulfonyl fluoride, Diers Alder cycloaddition click reagents and click chemistry, tetrazine, transcyclooctene, aldehyde, alkoxylamine, alkynes, cyclooctynes, azide, and the like. In some instances, $Z^3$ is selected from the group consisting of carboxylic acid, active ester (e.g., N-hydroxy succinimidyl ester (NHS) or sulfo-NHS), amino, maleimide, iodoacetyl and thiol. In certain embodiments of formulae described herein, at least one of $G^1$ and $G^2$ is described by the following structure:

where Ar is a π-conjugated aryl group, L is a linker and Z is a chemoselective tag or a specific binding member. In some cases, the L-Z group can be connected directed to a terminal co-monomer. In certain embodiments of formulae described herein, at least one of $G^1$ and $G^2$ is described by the following structure:

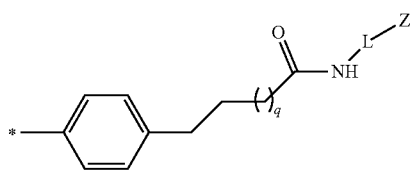

wherein:
q is 0 or an integer from 1-12;
L is an optional linker; and
Z is a chemoselective tag or a specific binding member. In certain embodiments, Z is a biomolecule. Biomolecules of interest include, but are not limited to, polypeptides, polynucleotides, carbohydrates, fatty acids, steroids, purines, pyrimidines, derivatives, structural analogs thereof and combinations thereof. In certain instances, Z is an antibody. In some instances, Z is an antibody fragment or binding derivative thereof. In some cases, the antibody fragment or binding derivative thereof is selected from the group consisting of a Fab fragment, a F(ab')$_2$ fragment, a scFv, a diabody and a triabody.

It is understood that for any of the structures and formula depicted herein that in some cases of the subject multichromophore the end groups depicted may be located at the opposite ends to those shown, e.g., the end groups $G^1$ and -Ph-L-Z may be switched. In some embodiments of the multichromophores described herein (e.g., formulae (II) to (V)), at least one of $G^1$ and $G^2$ is selected from one of the following structures 1-33:

1

*—H

2

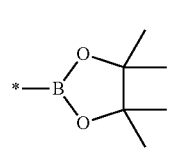

3

*—Cl

4

*—Br

5

*—SH

6

*—I

7

*—B(OH)$_2$

8

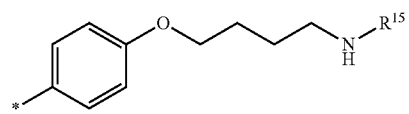

9

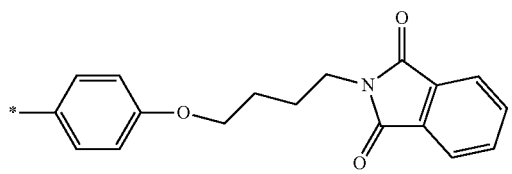

10

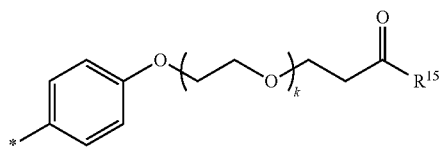

11

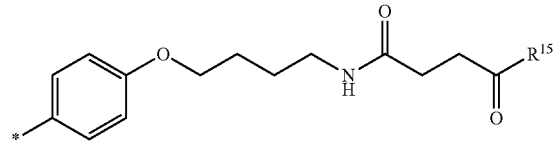

12

13

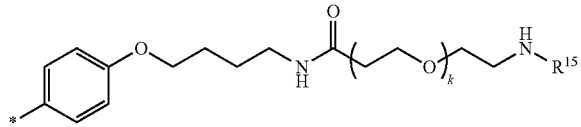

14

15

-continued
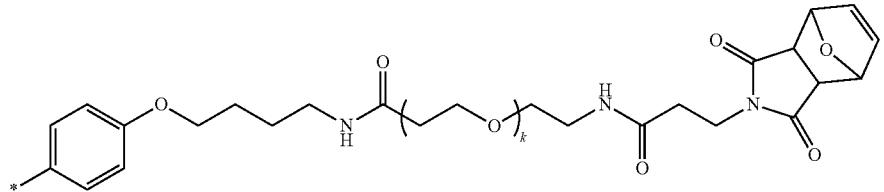
16
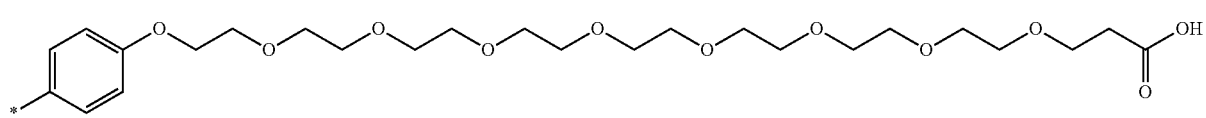
17
18
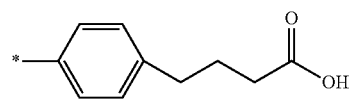
19
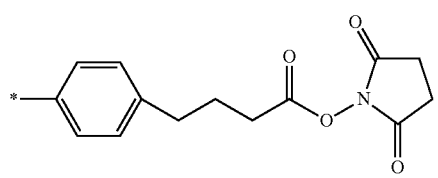
20
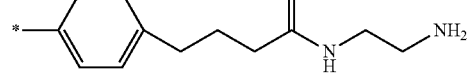
21
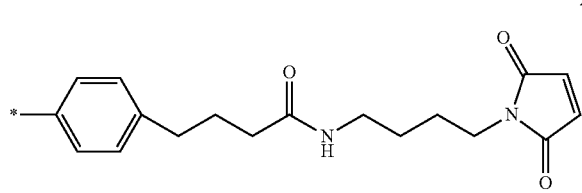
22
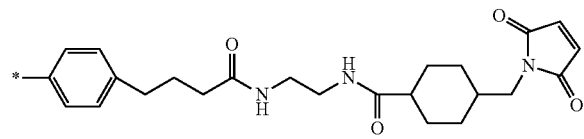
23
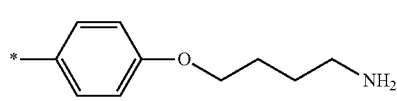
24
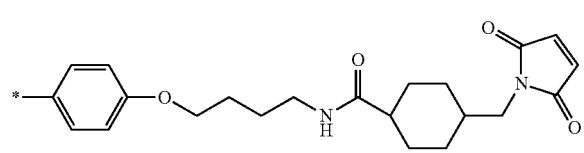
25
26
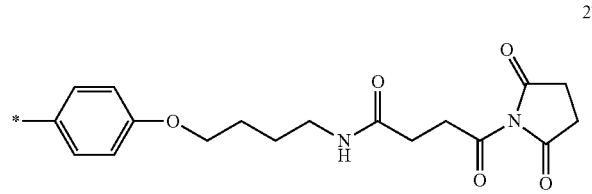
27
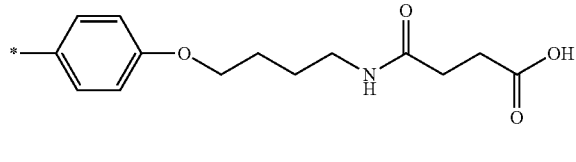
28
29
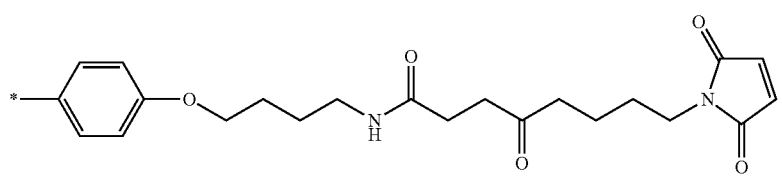

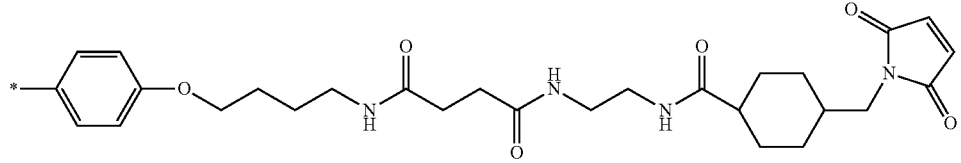

30

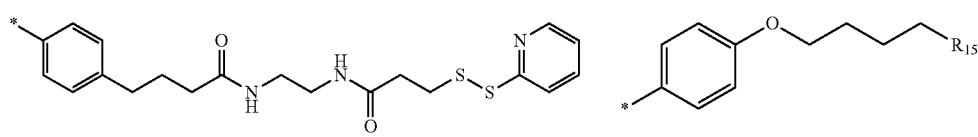

31

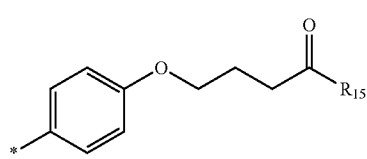

33

*=site for covalent attachment to unsaturated backbone;
wherein R' is independently H, halogen, $C_1$-$C_{12}$ alkyl, ($C_1$-$C_{12}$ alkyl)$NH_2$, $C_2$-$C_{12}$ alkene, $C_2$-$C_{12}$ alkyne, $C_3$-$C_{12}$cycloalkyl, $C_1$-$C_{12}$ haloalkyl, $C_2$-$C_{18}$(hetero)aryl, $C_2$-$C_{18}$(hetero)arylamino, —[$CH_2$—$CH_2$]$_{r'}$—$Z^1$, or ($C_1$-$C_{12}$)alkoxy-$X^1$; and wherein $Z^1$ is —OH or —COOH; $X^1$ is —$NH_2$, —NHCOOH, —NHCOOC($CH_3$)$_3$, —NHCO(C3-C12)cycloalkyl(C1-C4)alkyl-N-maleimide; or —NHCO[$CH_2$—$CH_2$—O]$_{s'}$($CH_2$)$_{s'}$$NH_2$; r' is an integer from 1 to 20; and each s' is independently an integer from 1 to 20, ($CH_2$)$_3$(O$CH_2$$CH_2$)$_{x''}$O$CH_3$ where x" is independently an integer from 0 to 50, or a benzyl optionally substituted with one or more halogen, hydroxyl, $C_1$-$C_{12}$ alkoxy, or (O$CH_2$$CH_2$)$_{y''}$$CH_3$ where each y" is independently an integer from 0 to 50 and R' is different from R;
wherein k is 2, 4, 8, 12 or 24;
wherein $R^{15}$ is selected from the group consisting of I-u having the structure:

*—OH    l

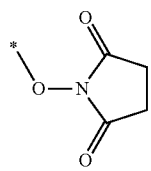    m

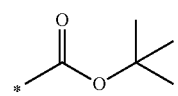    n

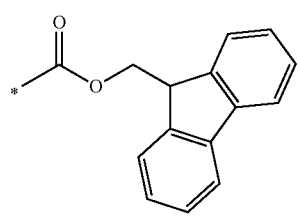    o

-continued

*—NH—O—NH₂    p

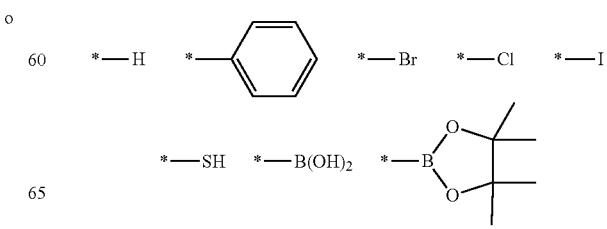

32

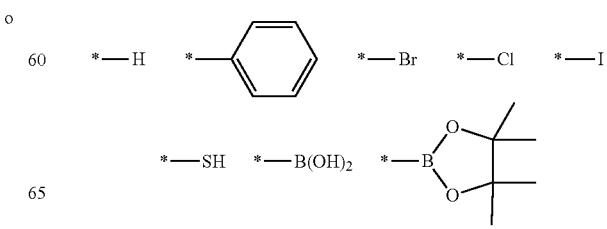

*—C(=O)—OH    r

*—NH₂    s

*—SH    t

*—H    u

*=site for covalent attachment to backbone.

In some embodiments of the multichromophores described herein (e.g., formulae (I)-(V), at least one end group (e.g., $T^2$-$Z^2$, $G^1$, $G^2$, -L-Z, -$L^3$-$Z^3$), or sidechain group, is selected from one of the following structures:

*—H    *—Ph    *—Br    *—Cl    *—I

*—SH    *—B(OH)₂    *—Bpin

-continued

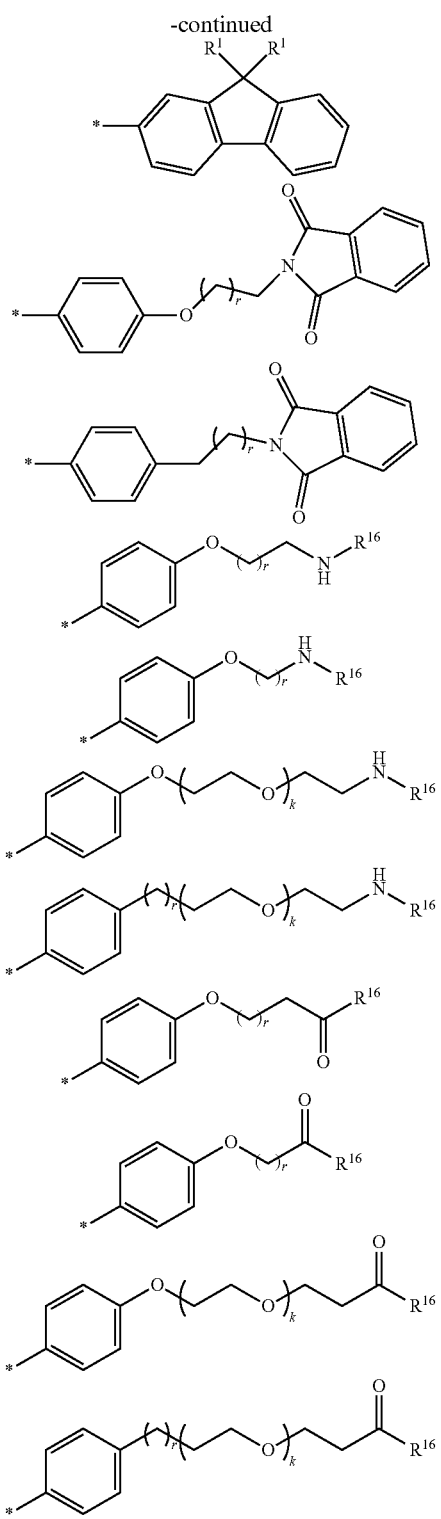

wherein r is 0 or an integer from 1-50; k is 0 or an integer from 1-50 (e.g., 1-20); $R^1$ is as defined for any of the fluorene co-monomers described herein; and $R^{16}$ is selected from H, OH, $NH_2$, —$NH(CH_2)_r$-$NH_2$, and —$NH(CH_2)_r$COOH. In certain instances, r is 1 to 20, such as 3 to 20, 3 to 15, 3 to 12, or 6 to 12. In certain cases, r is 1, 2, 3, 4, 5, 6, 7, 8, 9, 10, 11 or 12. In some cases, r is 3. In some cases, r is 4. In some cases, r is 5. In some cases, r is 6. In some cases, r is 7. In some cases, r is 8. In some cases, r is 9. In some cases, r is 10. In some cases, r is 11.

In some embodiments, the multichromophore includes one or more of the following groups, e.g., as an end group or sidechain group for conjugation to a compatible functional group on another molecule:

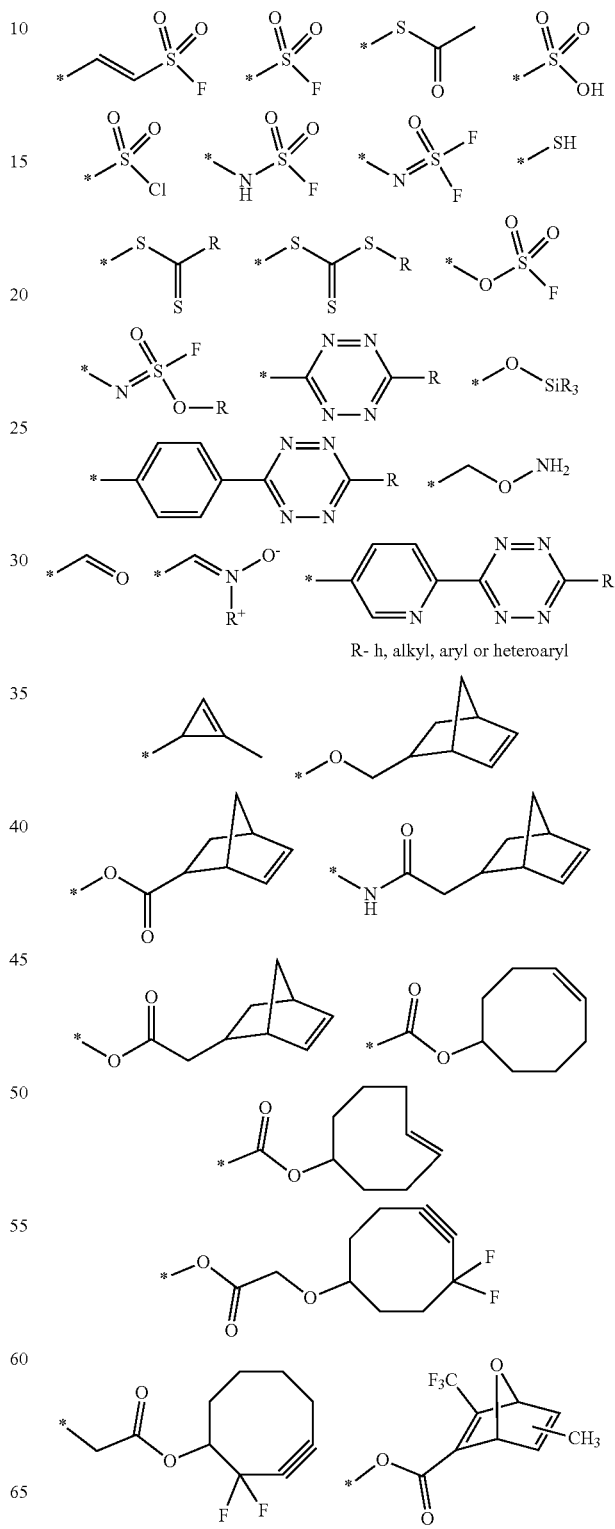

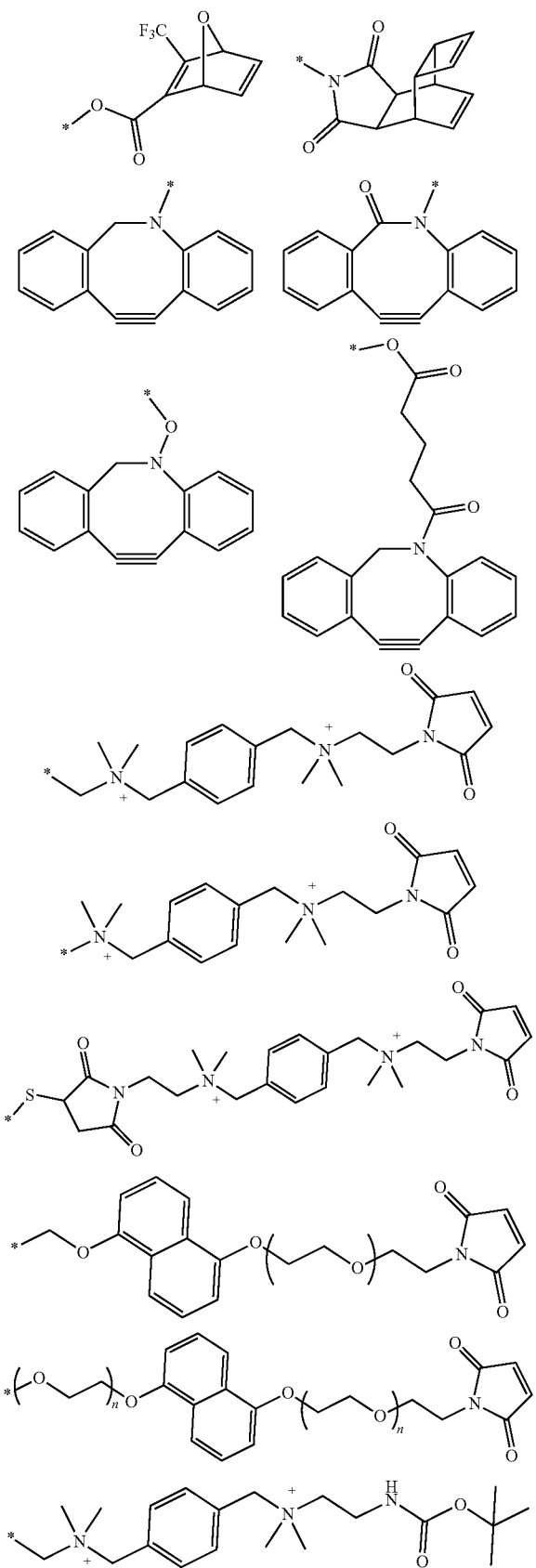
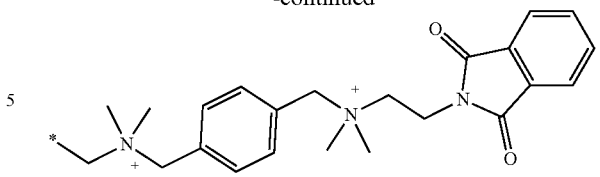

Labelled Specific Binding Members

Aspects of the present disclosure include labelled specific binding members. A labelled specific binding member is a conjugate of a subject polymeric dye (e.g., as described herein) and a specific binding member. Any of the polymeric dyes or polymeric tandem dyes described herein may be conjugated to a specific binding member. The specific binding member and the polymeric dye can be conjugated (e.g., covalently linked) to each other at any convenient locations of the two molecules, via an optional linker. In some embodiments, the labelled specific binding member is aggregation resistant. As used herein, by "aggregation-resistant" is meant a labelled specific binding member capable of forming a homogenous aqueous composition without aggregated precipitate at a concentration of 1 mg/ml or more in an aqueous buffer of interest, such as 2 mg/ml or more, 3 mg/ml or more, 4 mg/ml or more, 5 mg/ml or more, 6 mg/ml or more, 7 mg/ml or more, 8 mg/ml or more, 9 mg/ml or more, 10 mg/mL or more or even more of the labelled specific binding member.

In certain embodiments, the labelled specific binding member comprises: a water solvated polymeric dye having a deep ultraviolet excitation spectrum and comprising a segment of π-conjugated co-monomers and a conjugation-modifying repeat unit; and a specific binding member covalently linked to the multichromophore.

As used herein, the term "specific binding member" refers to one member of a pair of molecules which have binding specificity for one another. One member of the pair of molecules may have an area on its surface, or a cavity, which specifically binds to an area on the surface of, or a cavity in, the other member of the pair of molecules. Thus the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10 \times 10^{-9}$ M or less, such as $1 \times 10^{-9}$ M or less, $3 \times 10^{-10}$ M or less, $1 \times 10^{-10}$ M or less, $3 \times 10^{-11}$ M or less, $1 \times 10^{-11}$ M or less, $3 \times 10^{-12}$ M or less or $1 \times 10^{-12}$ M or less.

The specific binding member can be proteinaceous. As used herein, the term "proteinaceous" refers to a moiety that is composed of amino acid residues. A proteinaceous moiety can be a polypeptide. In certain cases, the proteinaceous specific binding member is an antibody. In certain embodiments, the proteinaceous specific binding member is an antibody fragment, e.g., a binding fragment of an antibody that specific binds to a polymeric dye. As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (k), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. The term antibody is meant to include full length antibodies and may refer to a natural antibody from any organism, an engineered antibody, or an antibody generated recombinantly for experimental, therapeutic, or other purposes as further defined below.

Antibody fragments of interest include, but are not limited to, Fab, Fab', F(ab')2, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions.

In certain embodiments, the specific binding member is a Fab fragment, a $F(ab')_2$ fragment, a scFv, a diabody or a triabody. In certain embodiments, the specific binding member is an antibody. In some cases, the specific binding member is a murine antibody or binding fragment thereof. In certain instances, the specific binding member is a recombinant antibody or binding fragment thereof.

In some embodiments, the labelled specific binding member includes: a water solvated light harvesting multichromophore (e.g., as described herein); and a signaling chromophore covalently linked to the multichromophore in energy-receiving proximity therewith (e.g., as described herein); and a specific binding member covalently linked to the multichromophore. In some instances of the labelled specific binding member, the multichromophore of any of the formula described herein (e.g., formulae (I)-(V)), wherein: $G^1$ and $G^2$ are each independently selected from the group consisting of a terminal group (e.g., end group), a π conjugated segment, a linker and a linked specific binding member, wherein at least one of $G^1$ and $G^2$ is a linked specific binding member.

Methods

As summarized above, aspects of the invention include methods of evaluating a sample for the presence of a target analyte. Aspects of the method include contacting the sample with a polymeric dye conjugate that specifically binds the target analyte to produce a labelling composition contacted sample. As used herein, the terms "polymeric dye conjugate" and "labelled specific binding member" are used interchangeably. As such, the polymeric dye conjugate can include: (i) a water solvated polymeric dye (e.g., as described herein); and (ii) a specific binding member (e.g., as described herein). In some instances, the polymeric dye conjugate further comprises a signaling chromophore covalently linked to a multichromophore of the polymeric dye in energy-receiving proximity therewith.

Any convenient method may be used to contact the sample with a polymeric dye conjugate that specifically binds to the target analyte to produce the labelling composition contacted sample. In some instances, the sample is contacted with the polymeric dye conjugate under conditions in which the specific binding member specifically binds to the target analyte, if present. For specific binding of the specific binding member of the conjugate with the target analyte, an appropriate solution may be used that maintains the biological activity of the components of the sample and the specific binding member. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. Convenient buffers include HEPES, phosphate buffers, lactate buffers, etc. Various media are commercially available and may be used according to the nature of the target analyte, including dMEM, HBSS, dPBS, RPMI, Iscove's medium, etc., in some cases supplemented with fetal calf serum or human platelet lysate. The final components of the solution may be selected depending on the components of the sample which are included.

The temperature at which specific binding of the specific binding member of the conjugate to the target analyte takes place may vary, and in some instances may range from 5° C. to 50° C., such as from 10° C. to 40° C., 15° C. to 40° C., 20° C. to 40° C., e.g., 20° C., 25° C., 30° C., 35° C. or 37° C. (e.g., as described above). In some instances, the temperature at which specific binding takes place is selected to be compatible with the biological activity of the specific binding member and/or the target analyte. In certain instances, the temperature is 25° C., 30° C., 35° C. or 37° C. In certain cases, the specific binding member is an antibody or fragment thereof and the temperature at which specific binding takes place is room temperature (e.g., 25° C.), 30° C., 35° C. or 37° C. Any convenient incubation time for specific binding may be selected to allow for the formation of a desirable amount of binding complex, and in some instances, may be 1 minute (min) or more, such as 2 min or more, 10 min or more, 30 min or more, 1 hour or more, 2 hours or more, or even 6 hours or more.

Any convenient specific binding members may be utilized in the conjugate. Specific binding members of interest include, but are not limited to, those agents that specifically bind cell surface proteins of a variety of cell types, including but not limited to, stem cells, e.g., pluripotent stem cells, hematopoietic stem cells, T cells, T regulator cells, dendritic cells, B Cells, e.g., memory B cells, antigen specific B cells, granulocytes, leukemia cells, lymphoma cells, virus cells (e.g., HIV cells) NK cells, macrophages, monocytes, fibroblasts, epithelial cells, endothelial cells, and erythroid cells. Target cells of interest include cells that have a convenient cell surface marker or antigen that may be captured by a convenient specific binding member conjugate. In some embodiments, the target cell is selected from HIV containing cell, a Treg cell, an antigen-specific T-cell populations, tumor cells or hematopoetic progenitor cells (CD34+) from whole blood, bone marrow or cord blood. Any convenient cell surface proteins or cell markers may be targeted for specific binding to polymeric dye conjugates in the subject methods. In some embodiments, the target cell includes a cell surface marker selected from a cell receptor and a cell surface antigen. In some cases, the target cell may include a cell surface antigen such as CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, T cell receptor alpha/beta, T cell receptor gamma/delta, CD253, CD95, CD20, CD105, CD117, CD120b, Notch4, Lgr5 (N-Terminal), SSEA-3, TRA-1-60 Antigen, Disialoganglioside GD2 and CD71.

Any convenient targets may be selected for evaluation utilizing the subject methods. Targets of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term "a target protein" refers to all members of the target family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially. In some embodiments, the polymeric dye conjugates include an antibody or antibody fragment. Any convenient target analyte that specifically binds an antibody or antibody fragment of interest may be targeted in the subject methods.

In some embodiments, the target analyte is associated with a cell. In certain instances, the target analyte is a cell surface marker of the cell. In certain cases, the cell surface marker is selected from the group consisting of a cell receptor and a cell surface antigen. In some instances, the target analyte is an intracellular target, and the method further includes lysing the cell.

In some embodiments, the sample may include a heterogeneous cell population from which target cells are isolated. In some instances, the sample includes peripheral whole blood, peripheral whole blood in which erythrocytes have been lysed prior to cell isolation, cord blood, bone marrow, density gradient-purified peripheral blood mononuclear cells or homogenized tissue. In some cases, the sample includes hematopoetic progenitor cells (e.g., CD34+ cells) in whole blood, bone marrow or cord blood. In certain embodiments, the sample includes tumor cells in peripheral blood. In certain instances, the sample is a sample including (or suspected of including) viral cells (e.g., HIV).

The labelled specific binding members find use in the subject methods, e.g., for labeling a target cell, particle, target or analyte with a polymeric dye or polymeric tandem dye. For example, labelled specific binding members find use in labeling cells to be processed (e.g., detected, analyzed, and/or sorted) in a flow cytometer. The labelled specific binding members may include antibodies that specifically bind to, e.g., cell surface proteins of a variety of cell types (e.g., as described herein). The labelled specific binding members may be used to investigate a variety of biological (e.g., cellular) properties or processes such as cell cycle, cell proliferation, cell differentiation, DNA repair, T cell signaling, apoptosis, cell surface protein expression and/or presentation, and so forth. Labelled specific binding members may be used in any application that includes (or may include) antibody-mediated labeling of a cell, particle or analyte.

In some instances of the method, the labelled specific binding member includes a multichromophore as described herein (eg., according to any one of formulae (I)-(IV)). In certain cases, $G^1$ and $G^2$ are each independently selected from the group consisting of a terminal group, a π conjugated segment, a linker and a linked specific binding member, wherein at least one of $G^1$ and $G^2$ is a linked specific binding member.

Aspects of the method include assaying the labelling composition contacted sample for the presence of a polymeric dye conjugate-target analyte binding complex to evaluate whether the target analyte is present in the sample. Once the sample has been contacted with the polymeric dye conjugate, any convenient methods may be utilized in assaying the labelling composition contacted sample that is produced for the presence of a polymeric dye conjugate-target analyte binding complex. The polymeric dye conjugate-target analyte binding complex is the binding complex that is produced upon specific binding of the specific binding member of the conjugate to the target analyte, if present. Assaying the labelling composition contacted sample can include detecting a fluorescent signal from the binding complex, if present. In some cases, the assaying includes a separating step where the target analyte, if present, is separated from the sample. A variety of methods can be utilized to separate a target analyte from a sample, e.g., via immobilization on a support. Assay methods of interest include, but are not limited to, any convenient methods and assay formats where pairs of specific binding members such as avidin-biotin or hapten-anti-hapten antibodies find use, are of interest. Methods and assay formats of interest that may be adapted for use with the subject compositions include, but are not limited to, flow cytometry methods, in-situ hybridization methods, enzyme-linked immunosorbent assays (ELISAs), western blot analysis, magnetic cell separation assays and fluorochrome purification chromatography.

In certain embodiments, the method further includes contacting the sample with a second specific binding member that specifically binds the target analyte. In certain instances, the second specific binding member is support bound. Any convenient supports may be utilized to immobilize a component of the subject methods (e.g., a second specific binding member). In certain instances, the support is a particle, such as a magnetic particle. In some instances, the second specific binding member and the polymeric dye conjugate produce a sandwich complex that may be isolated and detected, if present, using any convenient methods. In some embodiments, the method further includes flow cytometrically analyzing the polymeric dye conjugate-target analyte binding complex, i.e., a fluorescently labelled target analyte. Assaying for the presence of a polymeric dye conjugate-target analyte binding complex may provide assay results (e.g., qualitative or quantitative assay data) which can be used to evaluate whether the target analyte is present in the sample.

Any convenient supports may be utilized in the subject methods to immobilize any convenient component of the methods, e.g., labelled specific binding member, target, secondary specific binding member, etc. Supports of interest include, but are not limited to: solid substrates, where the substrate can have a variety of configurations, e.g., a sheet, bead, or other structure, such as a plate with wells; beads, polymers, particle, a fibrous mesh, hydrogels, porous matrix, a pin, a microarray surface, a chromatography support, and the like. In some instances, the support is selected from the group consisting of a particle, a planar solid substrate, a fibrous mesh, a hydrogel, a porous matrix, a pin, a microarray surface and a chromatography support. The support may be incorporated into a system that it provides for cell isolation assisted by any convenient methods, such as a manually-operated syringe, a centrifuge or an automated liquid handling system. In some cases, the support finds use in an automated liquid handling system for the high throughput isolation of cells, such as a flow cytometer.

In some embodiments of the method, the separating step includes applying an external magnetic field to immobilize a magnetic particle. Any convenient magnet may be used as a source of the external magnetic field (e.g., magnetic field gradient). In some cases, the external magnetic field is generated by a magnetic source, e.g. by a permanent magnet or electromagnet. In some cases, immobilizing the magnetic particles means the magnetic particles accumulate near the surface closest to the magnetic field gradient source, i.e. the magnet.

The separating may further include one or more optional washing steps to remove unbound material of the sample from the support. Any convenient washing methods may be used, e.g., washing the immobilized support with a biocompatible buffer which preserves the specific binding interaction of the polymeric dye and the specific binding member. Separation and optional washing of unbound material of the sample from the support provides for an enriched population of target cells where undesired cells and material may be removed.

In certain embodiments, the method further includes detecting the labelled target. Detecting the labelled target may include exciting the multichromophore with one or more lasers and subsequently detecting fluorescence emission from the polymeric tandem dye using one or more optical detectors. Detection of the labelled target can be performed using any convenient instruments and methods, including but not limited to, flow cytometry, FACS systems, fluorescence microscopy; fluorescence, luminescence, ultraviolet, and/or visible light detection using a plate reader; high performance liquid chromatography (HPLC); and mass spectrometry. When using fluorescently labeled components in the methods and compositions of the present disclosure, it is recognized that different types of fluorescence detection systems can be used to practice the subject methods. In some cases, high throughput screening can be performed, e.g., systems that use 96 well or greater microtiter plates. A variety of methods of performing assays on fluorescent materials can be utilized, such as those methods described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

Fluorescence in a sample can be measured using a fluorimeter. In some cases, excitation radiation, from an excitation source having a first wavelength, passes through excitation optics. The excitation optics cause the excitation radiation to excite the sample. In response, fluorescently labelled targets in the sample emit radiation which has a wavelength that is different from the excitation wavelength. Collection optics then collect the emission from the sample. The device can include a temperature controller to maintain the sample at a specific temperature while it is being scanned. In certain instances, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In some embodiments, the method of evaluating a sample for the presence of a target analyte further includes detecting fluorescence in a flow cytometer. In some embodiments, the method of evaluating a sample for the presence of a target analyte further includes imaging the labelling composition contacted sample using fluorescence microscopy. Fluorescence microscopy imaging can be used to identify a polymeric dye conjugate-target analyte binding complex in the contacted sample to evaluate whether the target analyte is present. Microscopy methods of interest that find use in the subject methods include laser scanning confocal microscopy.

Also provided are methods of labelling a target molecule. The subject polymeric dyes, find use in a variety of methods of labelling, separation, detection and/or analysis. In some embodiments, the method includes: contacting the target molecule with a polymeric dye (e.g., as described herein) to produce a labelled target molecule, wherein the polymeric dye includes a conjugation tag that covalently links to the target molecule. In some cases, the polymeric dye further includes a signaling chromophore covalently linked to the multichromophore of the polymeric dye in energy-receiving proximity therewith. In some instances of the method, the polymeric dye member includes a multichromophore according to any one of formulae (I)-(IV) (e.g., as described herein), where one of $G^1$ and $G^2$ is a terminal group and the other of $G^1$ and $G^2$ is the conjugation tag.

As used herein the term "conjugation tag" refers to a group that includes a chemoselective functional group (e.g., as described herein) that can covalently link with a compatible functional group of a target molecule, after optional activation and/or deprotection. Any convenient conjugation tags may be utilized in the subject polymeric dyes in order to conjugate the dye to a target molecule of interest. In some embodiments, the conjugation tag includes a terminal functional group selected from an amino, a carboxylic acid or a derivative thereof, a thiol, a hydroxyl, a hydrazine, a hydrazide, a azide, an alkyne and a protein reactive group (e.g. amino-reactive, thiol-reactive, hydroxyl-reactive, imidazolyl-reactive or guanidinyl-reactive).

Any convenient methods and reagent may be adapted for use in the subject labelling methods in order to covalently link the conjugation tag to the target molecule. Methods of interest for labelling a target, include but are not limited to, those methods and reagents described by Hermanson, Bioconjugate Techniques, Third edition, Academic Press, 2013. The contacting step may be performed in an aqueous solution. In some instances, the conjugation tag includes an amino functional group and the target molecule includes an activated ester functional group, such as a NHS ester or sulfo-NHS ester, or vice versa. In certain instances, the conjugation tag includes a maleimide functional group and the target molecule includes a thiol functional group, or vice versa. In certain instances, the conjugation tag includes an alkyne (e.g., a cyclooctyne group) functional group and the target molecule includes an azide functional group, or vice versa, which can be conjugated via Click chemistry.

Any convenient target molecules may be selected for labelling utilizing the subject methods. Target molecules of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term "a target protein" refers to all members of the target family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially. In some embodiments, the target molecule is a specific binding member (e.g., as described herein). In certain instances, the specific binding member is an antibody. In some instances, the specific binding member is an antibody fragment or binding derivative thereof. In some case, the antibody fragment or binding derivative thereof is selected from the group consisting of a Fab fragment, a F(ab')$_2$ fragment, a scFv, a diabody and a triabody.

In some cases, the method includes a separating step where the labelled target molecule is separated from the reaction mixture, e.g., excess reagents or unlabeled target. A variety of methods may be utilized to separate a target from a sample, e.g., via immobilization on a support, precipitation, chromatography, and the like.

In some instances, the method further includes detecting and/or analyzing the labelled target molecule. In some instances, the method further includes fluorescently detecting the labelled target molecule. Any convenient methods may be utilized to detect and/or analyze the labelled target molecule in conjunction with the subject methods and compositions. Methods of analyzing a target of interest that find use in the subject methods, include but are not limited to, flow cytometry, fluorescence microscopy, in-situ hybridization, enzyme-linked immunosorbent assays (ELISAs), western blot analysis, magnetic cell separation assays and fluorochrome purification chromatography. Detection methods of interest include but are not limited to fluorescence spectroscopy, fluorescence microscopy, nucleic acid sequencing, fluorescence in-situ hybridization (FISH), protein mass spectroscopy, flow cytometry, and the like.

Detection may be achieved directly via the polymeric dye or polymeric tandem dye, or indirectly by a secondary detection system. The latter may be based on any one or a combination of several different principles including, but not limited to, antibody labelled anti-species antibody and other forms of immunological or non-immunological bridging and signal amplification systems (e.g., biotin-streptavidin technology, protein-A and protein-G mediated technology, or nucleic acid probe/anti-nucleic acid probes, and the like). Suitable reporter molecules may be those known in the field of immunocytochemistry, molecular biology, light, fluorescence, and electron microscopy, cell immunophenotyping, cell sorting, flow cytometry, cell visualization, detection, enumeration, and/or signal output quantification. More than one antibody of specific and/or non-specific nature might be labelled and used simultaneously or sequentially to enhance target detection, identification, and/or analysis.

Systems

Aspects of the invention further include systems for use in practicing the subject methods and compositions. A sample analysis system can include sample field of view or a flow channel loaded with a sample and a labelled specific binding member. In some embodiments, the system is a flow cytometric system including: a flow cytometer including a flow path; a composition in the flow path, wherein the composition includes: a sample; and a labelled specific binding member (e.g., as described herein).

In some embodiments, the system for analyzing a sample is a fluorescence microscopy system, including: a fluorescence microscope comprising a sample field of view; and a composition disposed in the sample field of view, wherein the composition comprises a sample; and a labelled specific binding member (e.g., as described herein).

In some instances of the systems, the labelled specific binding member includes: a water solvated light harvesting multichromophore (e.g., as described herein) and a specific binding member that specifically binds a target analyte covalently linked to the multichromophore. In some cases, the labelled specific binding member further comprises a signaling chromophore covalently linked to the multichromophore of the polymeric dye in energy-receiving proximity therewith. In some instances of the subject systems, the labelled specific binding member, the multichromophore is described by any one of formulae (I)-(IV) (e.g., as described herein), wherein: $G^1$ and $G^2$ are each independently selected from the group consisting of a terminal group, a $\pi$ conjugated segment, a linker and a linked specific binding member, wherein at least one of $G^1$ and $G^2$ is a linked specific binding member.

In certain embodiments of the systems, the composition further includes a second specific binding member that is support bound and specifically binds the target analyte. In some cases, the support includes a magnetic particle. As such, in certain instances, the system may also include a controllable external paramagnetic field configured for application to an assay region of the flow channel.

The sample may include a cell. In some instances, the sample is a cell-containing biological sample. In some instances, the sample includes a labelled specific binding member specifically bound to a target cell. In certain instances, the target analyte that is specifically bound by the specific binding member is a cell surface marker of the cell. In certain cases, the cell surface marker is selected from the group consisting of a cell receptor and a cell surface antigen.

In certain aspects, the system may also include a light source configured to direct light to an assay region of the flow channel or sample field of view. The system may include a detector configured to receive a signal from an assay region of the flow channel or a sample field of view, wherein the signal is provided by the fluorescent composition. Optionally further, the sample analysis system may include one or more additional detectors and/or light sources for the detection of one or more additional signals.

In certain aspects, the system may further include computer-based systems configured to detect the presence of the fluorescent signal. A "computer-based system" refers to the hardware means, software means, and data storage means used to analyze the information of the present invention. The minimum hardware of the computer-based systems of the present invention includes a central processing unit (CPU), input means, output means, and data storage means. A skilled artisan can readily appreciate that any one of the currently available computer-based system are suitable for use in the subject systems. The data storage means may include any manufacture including a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g., word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

In certain aspects, the system includes a flow cytometer. Flow cytometers of interest include, but are not limited, to those devices described in U.S. Pat. Nos. 4,704,891; 4,727,029; 4,745,285; 4,867,908; 5,342,790; 5,620,842; 5,627,037; 5,701,012; 5,895,922; and 6,287,791; the disclosures of which are herein incorporated by reference.

Other systems may find use in practicing the subject methods. In certain aspects, the system may be a fluorimeter or microscope loaded with a sample having a fluorescent composition of any of the embodiments discussed herein. The fluorimeter or microscope may include a light source configured to direct light to the assay region of the flow channel or sample field of view. The fluorimeter or microscope may also include a detector configured to receive a signal from an assay region of the flow channel or field of view, wherein the signal is provided by the fluorescent composition.

Kits

Aspects of the invention further include kits for use in practicing the subject methods and compositions. The compositions of the invention can be included as reagents in kits either as starting materials or provided for use in, for example, the methodologies described above.

A kit can include a polymeric dye including a water solvated light harvesting multichromophore (e.g., as described herein) and a container. Any convenient containers can be utilized, such as tubes, bottles, or wells in a multi-well strip or plate, a box, a bag, an insulated container, and the like. The subject kits can further include one or more components selected from a polymeric tandem dye, a fluorophore, a specific binding member, a specific binding member conjugate, a support bound specific binding member, a cell, a support, a biocompatible aqueous elution buffer, and instructions for use. In some embodiments of the kit, the multichromophore is covalently linked to a specific binding member. In some instances, the specific binding member is an antibody. In certain instances, the specific binding member is an antibody fragment or binding derivative thereof. In certain cases, the antibody fragment or binding derivative thereof is selected from the group consisting of a Fab fragment, a F(ab')2 fragment, a scFv, a diabody and a triabody.

In certain embodiments, the kit finds use in evaluating a sample for the presence of a target analyte, such as an intracellular target. As such, in some instances, the kit includes one or more components suitable for lysing cells. The one or more additional components of the kit may be provided in separate containers (e.g., separate tubes, bottles, or wells in a multi-well strip or plate).

In certain aspects, the kit further includes reagents for performing a flow cytometric assay. Reagents of interest include, but are not limited to, buffers for reconstitution and dilution, buffers for contacting a cell sample the multichromophore, wash buffers, control cells, control beads, fluorescent beads for flow cytometer calibration and combinations thereof. The kit may also include one or more cell fixing reagents such as paraformaldehyde, glutaraldehyde, methanol, acetone, formalin, or any combinations or buffers thereof. Further, the kit may include a cell permeabilizing reagent, such as methanol, acetone or a detergent (e.g., triton, NP-40, saponin, tween 20, digitonin, leucoperm, or any combinations or buffers thereof. Other protein transport inhibitors, cell fixing reagents and cell permeabilizing reagents familiar to the skilled artisan are within the scope of the subject kits.

The compositions of the kit may be provided in a liquid composition, such as any suitable buffer. Alternatively, the compositions of the kit may be provided in a dry composition (e.g., may be lyophilized), and the kit may optionally include one or more buffers for reconstituting the dry composition. In certain aspects, the kit may include aliquots of the compositions provided in separate containers (e.g., separate tubes, bottles, or wells in a multi-well strip or plate).

In addition, one or more components may be combined into a single container, e.g., a glass or plastic vial, tube or bottle. In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site. Any convenient means may be present in the kits.

Utility

The polymeric dyes, compositions, methods and systems as described herein may find use in a variety of applications, including diagnostic and research applications, in which the labelling, detection and/or analysis of a target of interest is desirable. Such applications include methodologies such as cytometry, microscopy, immunoassays (e.g. competitive or non-competitive), assessment of a free analyte, assessment of receptor bound ligand, and so forth. The compositions, system and methods described herein may be useful in analysis of any of a number of samples, including but not limited to, biological fluids, cell culture samples, and tissue samples. In certain aspects, the compositions, system and methods described herein may find use in methods where analytes are detected in a sample, if present, using fluorescent labels, such as in fluorescent activated cell sorting or analysis, immunoassays, immunostaining, and the like. In certain instances, the compositions and methods find use in applications where the evaluation of a sample for the presence of a target analyte is of interest.

In some cases, the methods and compositions find use in any assay format where the detection and/or analysis of a target from a sample is of interest, including but not limited to, flow cytometry, fluorescence microscopy, in-situ hybridization, enzyme-linked immunosorbent assays (ELISAs), western blot analysis, magnetic cell separation assays and fluorochrome purification chromatography. In certain instances, the methods and compositions find use in any application where the fluorescent labelling of a target molecule is of interest. The subject compositions may be adapted for use in any convenient applications where pairs of specific binding members find use, such as biotin-streptavidin and hapten-anti-hapten antibody.

Additional Embodiments

Notwithstanding the appended claims, the disclosure set forth herein is also defined by the following clauses:
Clause 1. A water solvated polymeric dye comprising:
 a segment of π-conjugated co-monomers; and
 a conjugation-modifying repeat unit;
 wherein the polymeric dye has a deep ultraviolet excitation spectrum.
Clause 2. The polymeric dye according to clause 1, wherein the polymeric dye comprises a plurality of π-conjugated segments separated by conjugation-modifying repeat units.
Clause 3. The polymeric dye according to clause 2, wherein the plurality of π-conjugated segments each have a conjugation length of 20 or less.
Clause 4. The polymeric dye according to any one of clauses 1-3, wherein the excitation spectrum of the polymeric dye has a $\lambda_{max}$ of 350 nm or less.
Clause 5. The polymeric dye according to any one of clauses 1-4, wherein the conjugation-modifying repeat unit comprises the structure:

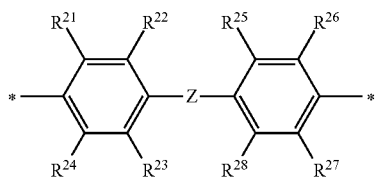

wherein:
 Z is selected from a covalent bond, a saturated atom, a saturated group and a functional group, with the proviso that when Z is a covalent bond at least two of $R^{22}$, $R^{23}$, $R^{25}$ and $R^{28}$ are not H (e.g., at least one of $R^{22}$ and $R^{23}$, and at least one of $R^{25}$ and $R^{28}$ is not H);
 $R^{21}$-$R^{28}$ are independently selected from H, alkyl, substituted alkyl, aryl, substituted aryl, heteroaryl, substituted heteroaryl, alkoxy, substituted alkoxy, hydroxy, cyano, halogen, sulfonate, sulfonamide, substituted sulfonamide, carboxy, carboxyamide, substituted carboxyamide, and a water solubilizing group, and wherein one or more of $R^{22}$, $R^{23}$, $R^{25}$ and $R^{28}$ is optionally cyclically linked to Z to provide a benzo-fused carbocycle or heterocycle ring; and
 each * is a site for covalent attachment to the backbone of the polymeric dye.
Clause 6. The polymeric dye according to clause 5, wherein Z is selected from a saturated carbon atom, a saturated heteroatom, a functional group and a saturated linker.
Clause 7. The polymeric dye according to any one of clauses 5-6, wherein:
 Z is selected from —S—, —S(O)—, —SO$_2$—, —SO$_2$NR'—, —S(O)O—, —O—, —C(O)—, —C(O)NR'—, —C(O)O—, —OC(O)NR'—, —OC(O)O—, —NR'C(O)NR'—, —C(R$^5$)(R$^6$)—, —Si(R$^5$)(R$^6$)—, —N(R')—, an alkyl linker and a polyethylene glycol linker; and
 each R', $R^5$ and $R^6$ is independently selected from H, alkyl, substituted alkyl, or wherein $R^5$ and/or $R^6$ is optionally cyclically linked to $R^{22}$, $R^{23}$, $R^{25}$ or $R^{28}$ provide the benzo-fused carbocycle or heterocycle ring.
Clause 8. The polymeric dye according to clause 7, wherein Z is selected from —S—, —S(O)—, —SO$_2$—, —O—, —C(O)—, —C(O)NR'—, —OC(O)NR'—, —OC(O)O— and —NR'C(O)NR'—.
Clause 9. The polymeric dye according to clause 7, wherein Z is C(R$^5$)(R$^6$)— or —Si(R$^5$)(R$^6$)—.
Clause 10. The polymeric dye according to clause 9, wherein the conjugation-modifying repeat unit comprises the structure:

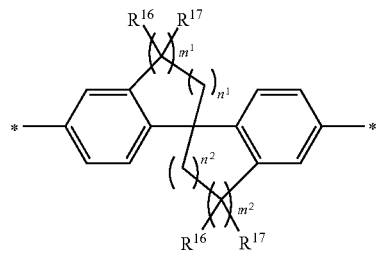

wherein:
 $n^1$, $n^2$, $m^1$ and $m^2$ are independently 0-3, wherein $n^1$+$m^1$ and $n^2$+$m^2$ are each independently 2-3;
 $R^{16}$ and $R^{17}$ are each independently selected from H, alkyl, substituted alkyl, alkoxy, substituted alkoxy, hydroxy, cyano, halogen, sulfonate, sulfonamide, substituted sulfonamide, carboxy, carboxyamide, substituted carboxyamide and a water solubilizing group; and
 each * is a site for covalent attachment to the backbone of the polymeric dye.
Clause 11. The polymeric dye according to clause 5, wherein Z is a covalent bond and the conjugation-modifying repeat unit comprises the structure:

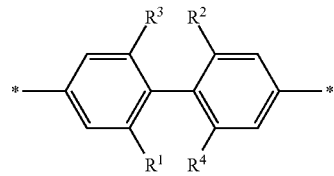

wherein:

R$^1$ to R$^4$ are independently selected from hydrogen, alkyl, substituted alkyl, halogen (e.g., fluoro), cyano,

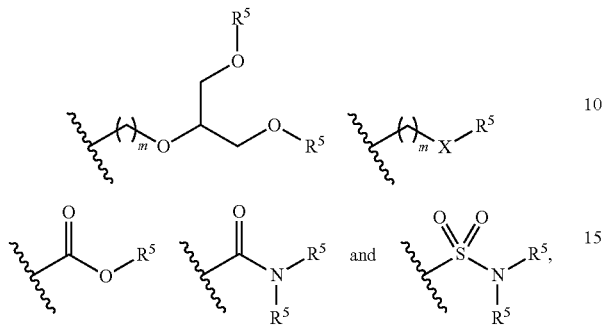

with the proviso that R$^1$ and R$^2$ are not hydrogen;

each R$^5$ is independently —(CH$_2$CH$_2$O)$_p$R' wherein each p is independently an integer from 0 to 50 (such as 6-50, 6-40, 6-30, 8-30, 10-30 or 10-20, e.g., 10, 11, 12, 13, 14, 15, 16, 17, 18, 19 or 20) and R' is H, an alkyl or a substituted alkyl;

X is O or S; and m is an integer from 0 to 10.

Clause 12. The polymeric dye according to any one of clauses 1-11, wherein the polymeric dye comprises a plurality of π-conjugated segments, each comprising one or more co-monomers selected from a substituted or unsubstituted aryl or heteroaryl co-monomer, an alkynyl co-monomer and a substituted or unsubstituted alkenyl co-monomer.

Clause 13. The polymeric dye according to clause 12, wherein the polymeric dye comprises a plurality of π-conjugated segments, each comprising one or more co-monomers selected from substituted or unsubstituted poly(p-phenylene), substituted or unsubstituted biphenyl, substituted or unsubstituted phenylene, substituted or unsubstituted fluorene, substituted or unsubstituted carbazole, substituted or unsubstituted silole, substituted or unsubstituted benzooxazole, substituted or unsubstituted benzothiazole, alkynyl, and substituted or unsubstituted alkenyl.

Clause 14. The polymeric dye according to any one of clauses 1-13, wherein the polymeric dye comprises a plurality of π-conjugated segments, each comprising one or more co-monomers selected from the following structures (a)-(k):

(a) 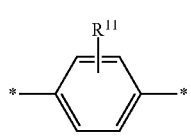

(b) 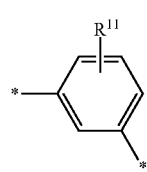

(c) 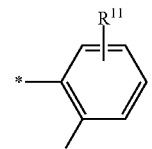

(d) 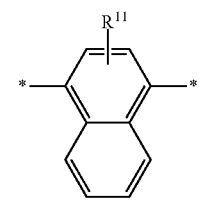

(e) 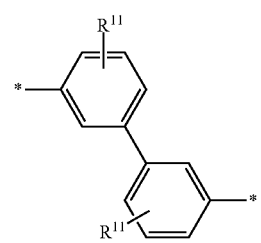

(f) 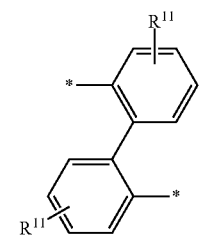

(g) 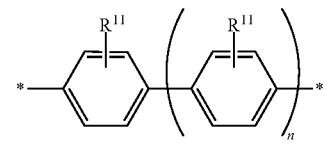

(h) 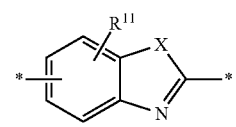

(i) 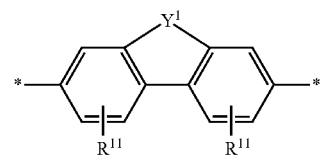

(j) 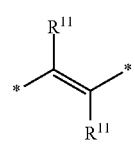

(k) 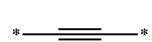

wherein:

X is O or S;

n is 1-6 (e.g., 1, 2 or 3)

R$^{11}$ is one or more optional substituents each independently selected from hydrogen, aryl, substituted aryl, heteroaryl, substituted heteroaryl, alkyl, substituted alkyl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide and a water solubilizing group; and each * is a site for covalent attachment to the backbone of the polymer.

Clause 15. The polymeric dye according to clause 14, wherein:

structure (a) is selected from:

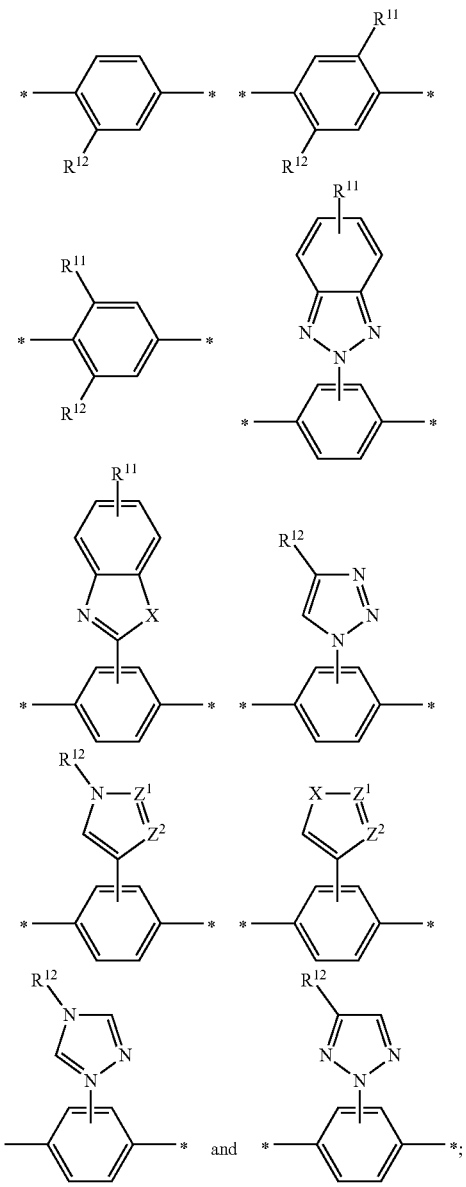

structure (g) is selected from:

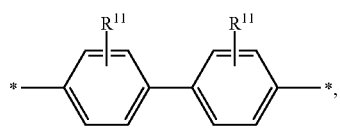

-continued

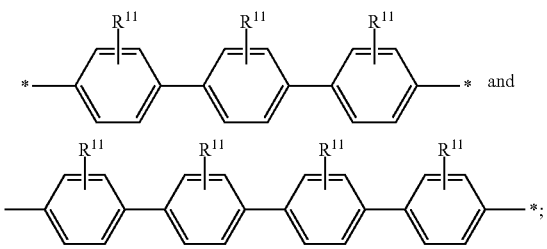

and structure (h) is selected from:

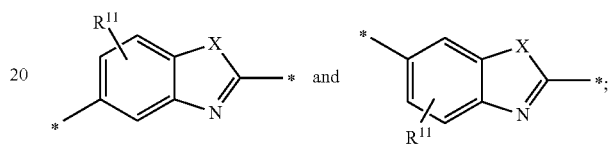

structure (i) is selected from:

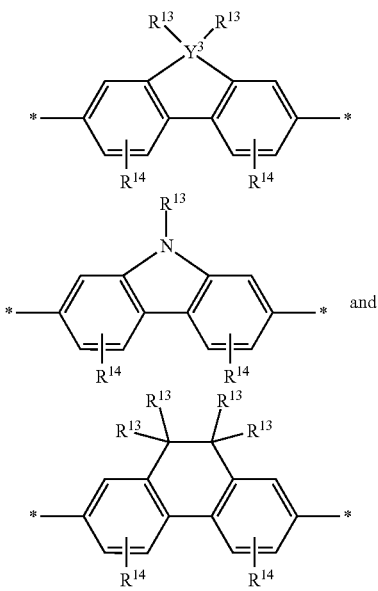

and wherein:

X is O or S;

$Z^1$ and $Z^2$ are independently selected from $CR^{12}$ and N;

$Y^3$ is C or Si; and each $R^{11}$ to $R^{14}$ is independently hydrogen, aryl, substituted aryl, heteroaryl, substituted heteroaryl, alkyl, substituted alkyl, alkoxy, substituted alkoxy, hydroxy, cyano, halogen, sulfonate, sulfonamide, substituted sulfonamide, carboxy, carboxyamide, substituted carboxyamide and a water solubilizing group, and wherein two $R^{14}$ groups are optionally cyclically linked to form a fused carbocyclic or heterocyclic ring (e.g., a partially saturated seven membered heterocyclic ring).

Clause 16. The polymeric dye according to clause 15, wherein each $R^{11}$ to $R^{14}$ is independently selected from H, F, methyl, trifluoromethyl, cyano,

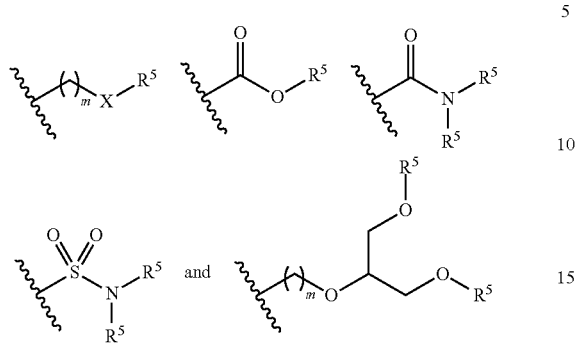

wherein:
X is O or S;
m is an integer from 0-10; and
$R^5$ is —$(CH_2CH_2O)_pR'$ wherein R' is H, alkyl or substituted alkyl (e.g., methyl) and each p is independently an integer from 0-40 (such as 6-40, 6-30, 8-30, 10-30 or 10-20, e.g., 10, 11, 12, 13, 14, 15, 16, 17, 18, 19 or 20).

Clause 17. The polymeric dye according to any one of clauses 1-16, wherein the polymeric dye is of formula (I):

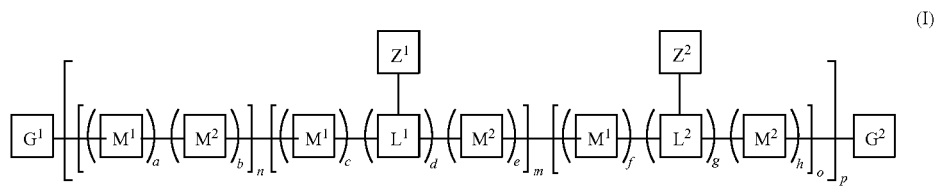

wherein:
each $M^1$ is independently selected from a substituted or unsubstituted aryl co-monomer, a substituted or unsubstituted heteroaryl co-monomer, an alkynyl co-monomer and a substituted or unsubstituted alkenyl co-monomer;
each $M^2$ is independently a conjugation-modifying repeat unit;
$L^1$ and $L^2$ are each independently a linker unit;
$Z^1$ is a linked chemoselective tag or a linked signaling chromophore (—$Z^1$);
$Z^2$ is a branched π-conjugated segment;
a-h are each independently 0 or 1, wherein a+b≥1 and b+e+h≥1;

n is from 1 to 10,000 (such as 1 to 1,000, 1 to 500 or 1 to 250, e.g., 2 to 250, 5 to 250 or 10 to 250);
m and o are each independently from 0 to 10,000 (such as 0 to 1,000, 0 to 500 or 0 to 250, e.g., 1 to 150, 2 to 250, 5 to 250 or 10 to 250);
p is from 1 to 100,000 (such as 1 to 10,000, 1 to 1,000, 1 to 500 or 1 to 250, e.g., 2 to 250, 5 to 250 or 10 to 250); and
$G^1$ and $G^2$ are independently selected from a terminal group, a π-conjugated segment, a linker and a linked specific binding member.

Clause 18. The polymeric dye according to clause 17, wherein the polymeric dye is of formula (II):

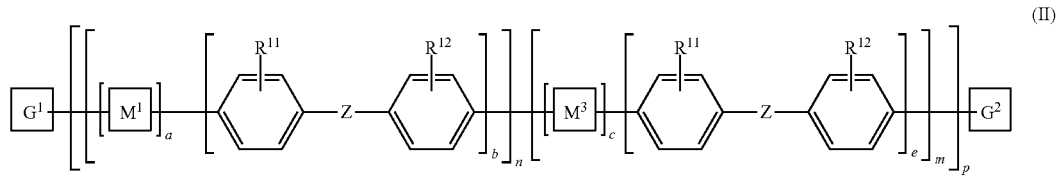

wherein:

$M^1$ and $M^3$ are independently selected from an aryl co-monomer, a heteroaryl co-monomer, an alkynyl co-monomer and an alkenyl co-monomer;

Z is selected from a covalent bond, a saturated atom or group and a functional group;

$R^{11}$ and $R^{12}$ are each independently selected from H, alkyl, substituted alkyl, alkoxy, substituted alkoxy, hydroxy, cyano, halogen, sulfonate, sulfonamide, substituted sulfonamide, carboxy, carboxyamide, substituted carboxyamide and a water solubilizing group;

a, b, c and e are each independently 0 or 1, wherein a+b≥1 and c+d≥1;

n is from 1 to 10,000 (such as 1 to 1,000, 1 to 500 or 1 to 250, e.g., 2 to 250, 5 to 250 or 10 to 250);

m is from 0 to 10,000 (such as 0 to 1,000, 0 to 500 or 0 to 250, e.g., 1 to 150, 2 to 250, 5 to 250 or 10 to 250);

p is from 1 to 100,000 (such as 1 to 10,000, 1 to 1,000, 1 to 500 or 1 to 250, e.g., 2 to 250, 5 to 250 or 10 to 250); and $G^1$ and $G^2$ are independently selected from a terminal group, a π-conjugated segment, a linker and a linked specific binding member.

Clause 19. The polymeric dye according to clause 17, wherein the polymeric dye is of formula (III):

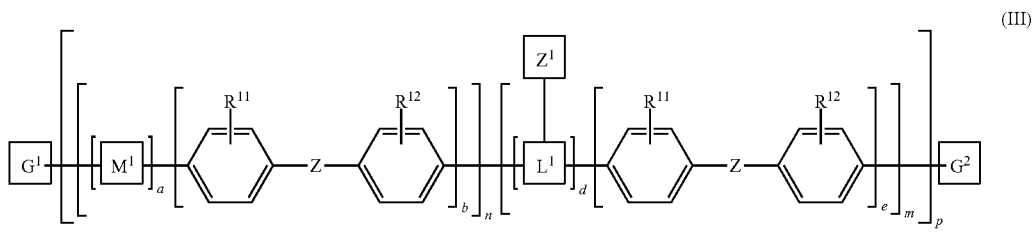

(III)

wherein:

$M^1$ is selected from an aryl co-monomer, a heteroaryl co-monomer, an alkynyl co-monomer and an alkenyl co-monomer;

$L^1$ is a linker unit comprising an aryl co-monomer, a heteroaryl co-monomer, an alkynyl co-monomer and an alkenyl co-monomer;

$Z^1$ is a linked chemoselective tag or a linked signaling chromophore ($-Z^1$);

Z is selected from a covalent bond, a saturated atom or group and a functional group;

$R^{11}$ and $R^{12}$ are each independently selected from H, alkyl, substituted alkyl, alkoxy, substituted alkoxy, hydroxy, cyano, halogen, sulfonate, sulfonamide, substituted sulfonamide, carboxy, carboxyamide, substituted carboxyamide and a water solubilizing group;

a, b, d and e are each independently 0 or 1, wherein a+b≥1 and d+e≥1;

n is from 1 to 10,000 (such as 1 to 1,000, 1 to 500 or 1 to 250, e.g., 2 to 250, 5 to 250 or 10 to 250);

m is from 0 to 10,000 (such as 0 to 1,000, 0 to 500 or 0 to 250, e.g., 1 to 150, 2 to 250, 5 to 250 or 10 to 250);

p is from 1 to 10,000 (such as 1 to 1,000, 1 to 500 or 1 to 250, e.g., 2 to 250, 5 to 250 or 10 to 250); and $G^1$ and $G^2$ are independently selected from a terminal group, a π-conjugated segment, a linker and a linked specific binding member.

Clause 20. The polymeric dye according to clause 17, wherein:

the polymeric dye is of formula (I) wherein a, b, g and h are each 1;

$Z^2$ has is a branched π-conjugated segment of formula (IV):

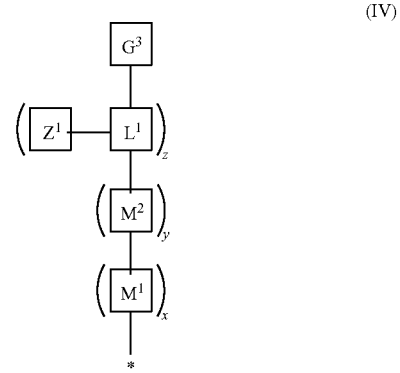

(IV)

wherein $M^1$, $M^2$, $L^1$, $Z^1$ are as defined in clause 17; and $G^3$ is a terminal group, a π-conjugated segment, a linker or a linked specific binding member.

Clause 21. The polymeric dye according to clause 20, wherein:

the polymeric dye is of formula (I) wherein a, b, d, e, g, h are each 1; and $Z^1$ is a linked functional signaling chromophore.

Clause 22. The polymeric dye according to any one of clauses 17-19, wherein the polymeric dye is of formula (V):

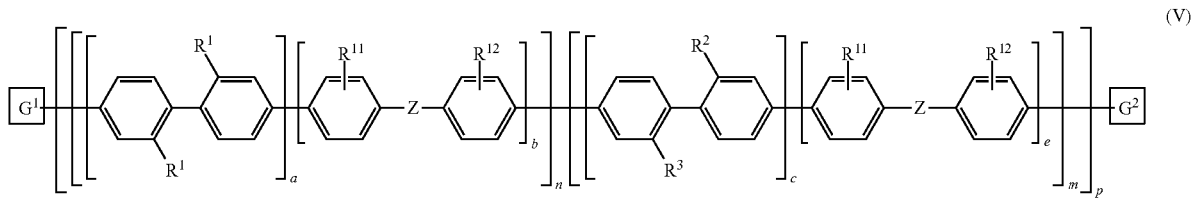

(V)

wherein

Z is selected from a covalent bond, a saturated atom or group and a functional group;

$R^1$-$R^3$, $R^{11}$ and $R^{12}$ are each independently selected from H, alkyl, substituted alkyl, alkoxy, substituted alkoxy, hydroxy, cyano, halogen, sulfonate, sulfonamide, substituted sulfonamide, carboxy, carboxyamide, substituted carboxyamide, a water solubilizing group, a linked chemoselective tag and a linked signalling chromophore;

a, b, c and e are each independently 0 or 1, wherein a+b≥1 and c+d≥1;

n is from 1 to 10,000 (such as 1 to 1,000, 1 to 500 or 1 to 250, e.g., 2 to 250, 5 to 250 or 10 to 250);

m is from 0 to 10,000 (such as 0 to 1,000, 0 to 500 or 0 to 250, e.g., 1 to 150, 2 to 250, 5 to 250 or 10 to 250);

p is from 1 to 10,000 (such as 1 to 1,000, 1 to 500 or 1 to 250, e.g., 2 to 250, 5 to 250 or 10 to 250); and $G^1$ and $G^2$ are independently selected from a terminal group, a π-conjugated segment, a linker and a linked specific binding member.

Clause 23. The polymeric dye according to clause 22, wherein:

$R^1$-$R^3$ are each independently a water solubilizing group; and $R^2$ and $R^3$ are the same.

Clause 24. The polymeric dye according to clause 22, wherein:

each $R^1$ and $R^2$ are each independently a water solubilizing group; and $R^3$ is a linked chemoselective tag or a linked signalling chromophore.

Clause 25. The polymeric dye according to any one of clauses 18-24, wherein Z is selected from a saturated carbon atom, a saturated heteroatom, a functional group (e.g., an oxygen and/or nitrogen-containing functional group, such as a sulfonyl, a keto, an amide, ester, carbonate, carbamate or urea) and a saturated linker.

Clause 26. The polymeric dye according to clause 25, wherein:

Z is selected from —S—, —S(O)—, —SO$_2$—, —SO$_2$NR'—, —S(O)O—, —O—, —C(O)—, —C(O)NR'—, —C(O)O—, —OC(O)NR'—, —OC(O)O—, —NR'C(O)NR'—, —C($R^5$)($R^6$)—, —Si($R^5$)($R^6$)—, —N(R')—, an alkyl linker (e.g., $C_2$-$C_{12}$, such as $C_2$-$C_6$ substituted or unsubstituted alkyl linker) and a polyethylene glycol linker; and each R', $R^5$ and $R^6$ is independently selected from H, alkyl, substituted alkyl, and wherein $R^5$ and/or $R^6$ is optionally cyclically linked to $R^{12}$ or $R^{12}$ to provide a benzo-fused carbocycle or heterocycle ring.

Clause 27. The polymeric dye according to clause 26, wherein Z is selected from —S—, —S(O)—, —SO$_2$—, —O—, —C(O)—, —C(O)NR'—, —OC(O)NR'—, —OC(O)O— and —NR'C(O)NR'—.

Clause 28. The polymeric dye according to clause 27, wherein each Z is —SO$_2$—.

Clause 29. The polymeric dye according to clause 26, wherein Z is C($R^5$)($R^6$)— or —Si($R^5$)($R^6$)—.

Clause 30. The polymeric dye according to any one of clauses 22-29, wherein each $R^1$ and $R^2$ are each independently a water solubilizing group selected from:

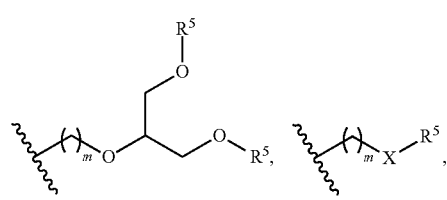

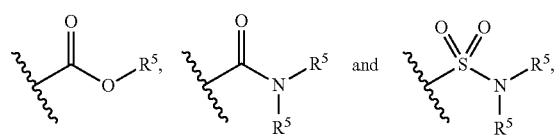

wherein m is 0-10 (such as 1-6, e.g., 1, 2, 3, 4, 5 or 6) and each $R^5$ is independently —(CH$_2$CH$_2$O)$_p$R' wherein p is an integer from 0 to 50 (such as 6-50, 6-40, 6-30, 8-30, 10-30 or 10-20, e.g., 10, 11, 12, 13, 14, 15, 16, 17, 18, 19 or 20) and R' is H, an alkyl or a substituted alkyl; and X is O.

Clause 31. The polymeric dye according to clause 22, wherein the polymeric dye has the formula (VI):

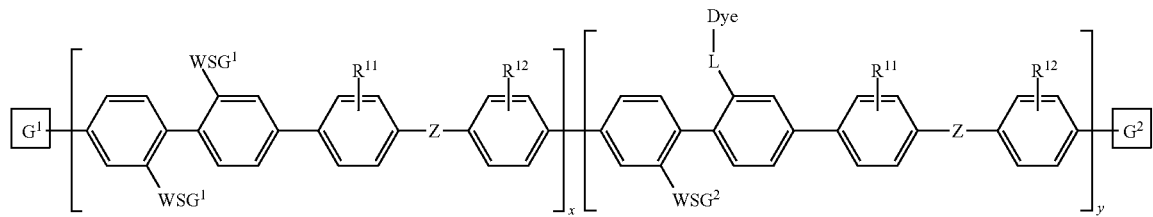

(VI)

wherein:

Dye is the linked signaling chromophore and L is a linker; WSG1 and WSG2 are each independently a water solubilizing group (WSG) (e.g., as described herein);

Z is selected from —S—, —S(O)—, —SO$_2$—, —SO$_2$NR'—, —S(O)O—, —O—, —C(O)—, —C(O)NR'—, —C(O)O—, —OC(O)NR'—, —OC(O)O—, —NR'C(O)NR'—, —C(R$^5$)(R$^6$)—, —Si(R$^5$)(R$^6$)—, —N(R')—, an alkyl linker (e.g., C$_2$-C$_{12}$, such as C$_2$-C$_6$ substituted or unsubstituted alkyl linker) and a polyethylene glycol linker;

each R', R$^5$ and R$^6$ is independently selected from H, alkyl, substituted alkyl, and wherein R$^5$ and/or R$^6$ is optionally cyclically linked to R$^{12}$ or R$^{12}$ to provide a benzo-fused carbocycle or heterocycle ring; and x and y represent mol % values (e.g., y is 1-25 mol % and x is 99 mol % or less).

Clause 33. The polymeric dye according to clause 32, wherein Z is selected from —S—, —S(O)—, —SO$_2$—, —O—, —C(O)—, —C(O)NR'—, —OC(O)NR'—, —OC(O)O— and —NR'C(O)NR'—.

Clause 34. The polymeric dye according to clause 32, wherein Z is —SO$_2$—.

Clause 35. The polymeric dye according to clause 32, wherein Z is C(R$^5$)(R$^6$)— or —Si(R$^5$)(R$^6$)—.

Clause 36. The polymeric dye according to any one of clauses 32-35, wherein each WSG$^1$ and WSG$^2$ are each independently a water solubilizing group selected from:

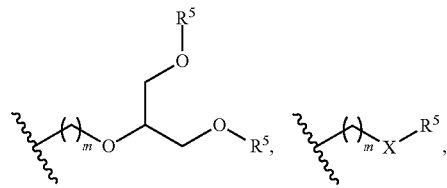

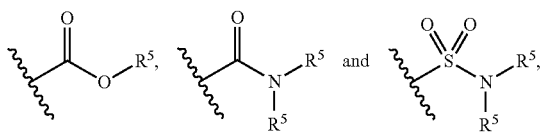

wherein m is 0-10 (such as 1-6, e.g., 1, 2, 3, 4, 5 or 6) and each R$^5$ is independently —(CH$_2$CH$_2$O)$_p$R' wherein p is an integer from 0 to 50 (such as 6-50, 6-40, 6-30, 8-30, 10-30 or 10-20, e.g., 10, 11, 12, 13, 14, 15, 16, 17, 18, 19 or 20) and R' is H, an alkyl or a substituted alkyl; and X is O.

Clause 37. The polymeric dye according to clause 22, wherein the polymeric dye has the formula (VII):

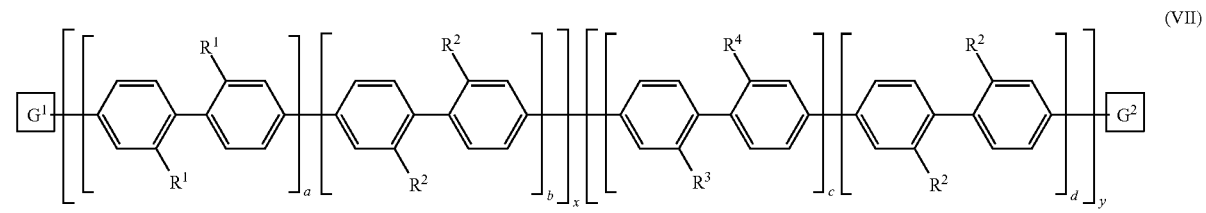

(VII)

wherein:

R¹-R⁴ are each independently selected from H, alkyl, substituted alkyl, alkoxy, substituted alkoxy, hydroxy, cyano, halogen, sulfonate, sulfonamide, substituted sulfonamide, carboxy, carboxyamide, substituted carboxyamide, a water solubilizing group (WSG) (e.g., as described herein), a linked chemoselective tag and a linked signalling chromophore;

a, b, c and e are each independently 0 or 1, wherein a+b≥1 and c+d≥1;

x and y represent mol % values (e.g., y is 1-25 mol % and x is 99 mol % or less);

p is from 1 to 10,000 (such as 1 to 1,000, 1 to 500 or 1 to 250, e.g., 2 to 250, 5 to 250 or 10 to 250); and G¹ and G² are independently selected from a terminal group, a π-conjugated segment, a linker and a linked specific binding member.

Clause 38. The polymeric dye according to clause 37, wherein R¹-R³ are each independently a water solubilizing group; and R² and R³ are the same.

Clause 39. The polymeric dye according to clause 37, wherein the subject polymeric dye has the formula (VIII):

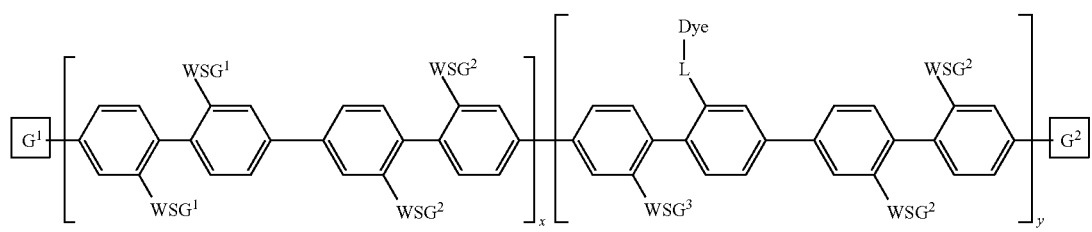

(VIII)

wherein:

Dye is the linked signaling chromophore and L is a linker; each WSG1, each WSG2 and WSG3 are each independently a water solubilizing group (WSG) (e.g., as described herein); and x and y represent mol % values. In some cases, y is 1-25 mol % and x is 99 mol % or less.

Clause 40. The polymeric dye according to clause 39, wherein WSG1, each WSG2 and WSG3 are independently a water solubilizing group selected from:

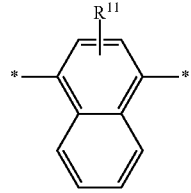

wherein m is 0-10 (such as 1-6, e.g., 1, 2, 3, 4, 5 or 6) and each R⁵ is independently —(CH₂CH₂O)ₚR' wherein p is an integer from 0 to 50 (such as 6-50, 6-40, 6-30, 8-30, 10-30 or 10-20, e.g., 10, 11, 12, 13, 14, 15, 16, 17, 18, 19 or 20) and R' is H, an alkyl or a substituted alkyl; and X is O.

Clause 41. The polymeric dye according to any one of clauses 17-21, wherein each M¹ and each M³ is independently selected from the following structures (a)-(k):

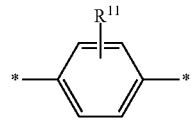

(a)

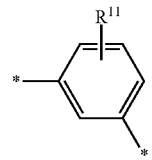

(b)

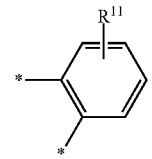

(c)

-continued

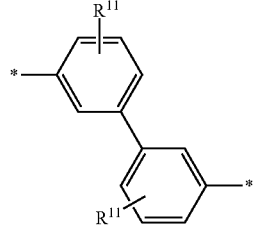

(d)

(e)

(f)

-continued

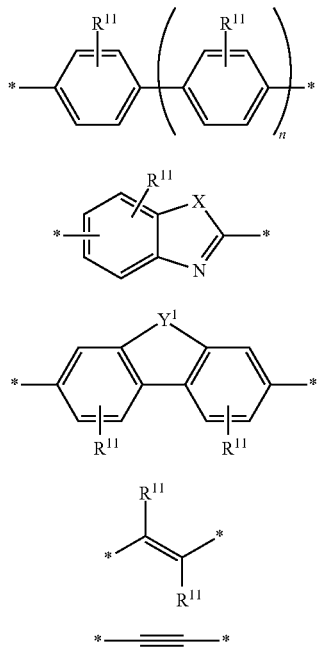

(g)
(h)
(i)
(j)
(k)

wherein:
X is O or S;
n is 1-6 (e.g., 1, 2 or 3);
$Y^1$ is selected from —C($R^{11}$)$_2$—, —Si($R^{11}$)$_2$—, —N$R^{11}$—, —C($R^{11}$)$_2$C($R^{11}$)$_2$— and —C($R^{11}$)$_2$C($R^{11}$)$_2$—;
$R^{11}$ is one or more optional substituents each independently selected from hydrogen, aryl, substituted aryl, heteroaryl, substituted heteroaryl, alkyl, substituted alkyl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide and a water solubilizing group or wherein any two adjacent $R^{11}$ groups are optionally cyclically linked (e.g., to provide a carbocycle or heterocycle ring); and
each * is a site for covalent attachment to the backbone of the polymer.

Clause 42. The polymeric dye according to clause 41, wherein:

structure (a) is selected from:

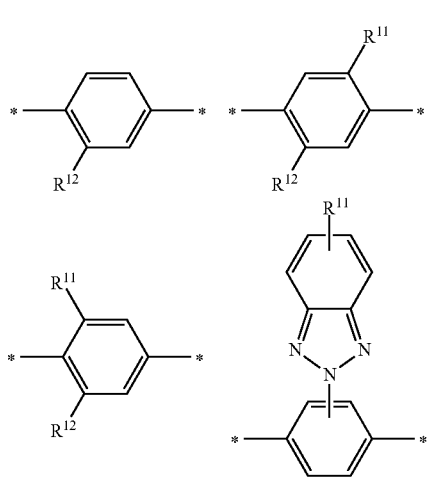

-continued

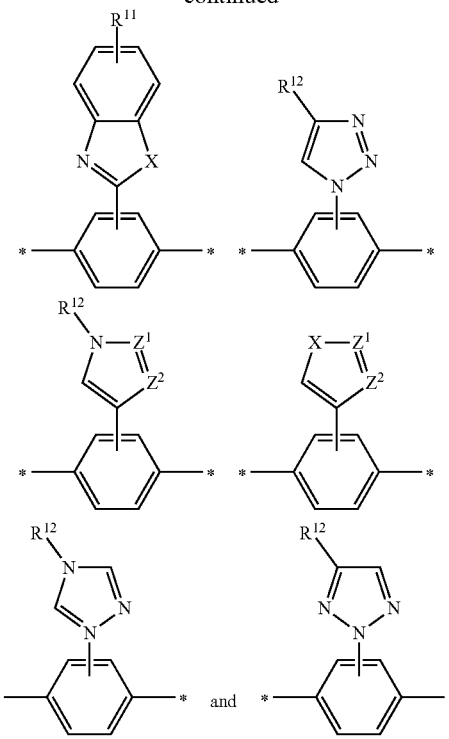

structure (g) is selected from:

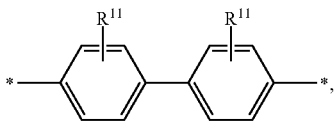

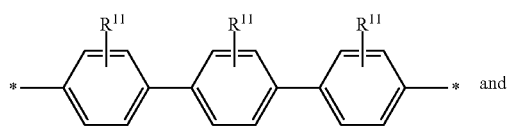

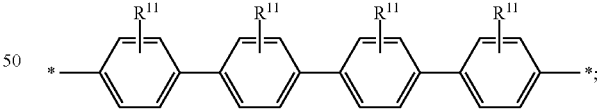

and structure (h) is selected from:

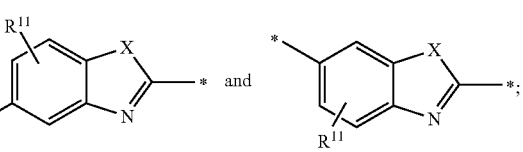

structure (i) is selected from:

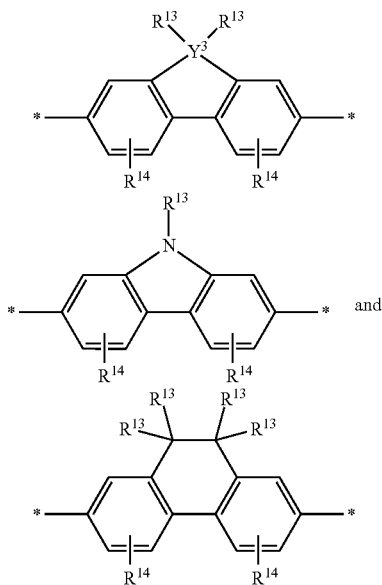

and
wherein:
X is O or S;
$Z^1$ and $Z^2$ are independently selected from $CR^{12}$ and N;
$Y^3$ is C or Si; and
each $R^{11}$ to $R^{14}$ is independently hydrogen, aryl, substituted aryl, heteroaryl, substituted heteroaryl, alkyl, substituted alkyl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide and a water solubilizing group, and wherein two $R^{14}$ groups are optionally cyclically linked to form a fused carbocyclic or heterocyclic ring (e.g., a partially saturated seven membered heterocyclic ring).

Clause 43. A polymeric tandem dye comprising:
a water solvated polymeric dye having a deep ultraviolet excitation spectrum and comprising a segment of π-conjugated co-monomers and a conjugation-modifying repeat unit; and
a signaling chromophore covalently linked to the water solvated polymeric dye in energy-receiving proximity therewith.

Clause 44. The polymeric tandem dye according to clause 43, wherein the conjugation-modifying repeat unit comprises the structure:

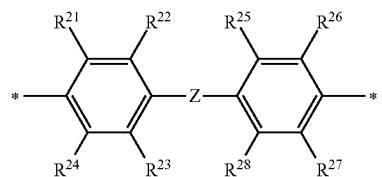

wherein:
Z is selected from a covalent bond, a saturated atom, a saturated group and a functional group, with the proviso that when Z is a covalent bond at least two of $R^{22}$, $R^{23}$, $R^{25}$ and $R^{28}$ are not H (e.g., at least one of $R^{22}$ and $R^{23}$, and at least one of $R^{25}$ and $R^{28}$ is not H);

$R^{21}$-$R^{28}$ are independently selected from H, alkyl, substituted alkyl, aryl, substituted aryl, heteroaryl, substituted heteroaryl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide, and a water solubilizing group, and wherein one or more of $R^{22}$, $R^{23}$, $R^{25}$ and $R^{28}$ is optionally cyclically linked to Z to provide a benzo-fused carbocycle or heterocycle ring; and
each * is a site for covalent attachment to the backbone of the polymeric dye.

Clause 45. The polymeric tandem dye according to clause 43, wherein the signaling chromophore emission has a quantum yield of 0.1 or more.

Clause 46. The polymeric tandem dye according to clause 43, wherein the polymeric dye has an extinction coefficient of $1\times10^6$ $M^{-1}cm^{-1}$ or more.

Clause 47. The polymeric tandem dye according to any one of clauses 43-46, wherein the multichromophore is substituted with non-ionic side groups capable of imparting solubility in water in excess of 10 mg/mL.

Clause 48. The polymeric tandem dye according to any one of clauses 43-47, wherein the signaling chromophore is a fluorophore.

Clause 49. The polymeric tandem dye according to any one of clauses 43-47, wherein the signaling chromophore is a quencher.

Clause 50. The polymeric tandem dye according to any one of clauses 43-49, wherein the signaling chromophore is selected from a rhodamine, a coumarin, a xanthene, a cyanine, a polymethine, a pyrene, a dipyrromethene borondifluoride, a napthalimide, a phycobiliprotein, a peridinum chlorophyll protein, conjugates thereof, and combinations thereof.

Clause 51. The polymeric tandem dye according to any one of clauses 43-48 and 50, wherein the signaling chromophore is selected from fluorescein, 6-FAM, rhodamine, Texas Red, California Red, iFluor594, tetramethylrhodamine, a carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy7®, Cy-Chrome, DyLight 350, DyLight 405, DyLight 488, DyLight 549, DyLight 594, DyLight 633, DyLight 649, DyLight 680, DyLight 750, DyLight 800, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br2, BODIPY® 530/550, BODIPY® 558/568, BODIPY® 564/570, BODIPY® 576/589, BODIPY® 581/591, BODIPY® 630/650, BODIPY® 650/665, BODIPY® R6G, BODIPY® TMR, BODIPY® TR, conjugates thereof and combinations thereof.

Clause 52. The polymeric tandem dye according to any one of clauses 43-51, wherein:
the signaling chromophore is linked to a co-monomer comprising 1% to 20% by molarity of the multichromophore; and
the polymeric dye is a conjugated polymer comprising 5 or more repeat units.

Clause 53. The polymeric tandem dye according to any one of clauses 43-48 and 50-52, wherein the signaling chromophore emission is 1.5-fold greater or more when excited by the polymeric dye as compared to direct excitation of the acceptor chromophore with incident light.

Clause 54. The polymeric tandem dye according to any one of clauses 43-53, wherein the polymeric dye comprises a terminal group -L³-Z where L³ is a linker and Z is a specific binding member.

Clause 55. The polymeric tandem dye according to clause 54, wherein the linker is selected from the group consisting of an alkyl, a substituted alkyl, an alkyl-amido, an alkyl-amido-alkyl and a PEG moiety.

Clause 56. The polymeric tandem dye according to clause 55, wherein -L³-Z is described by the following structure:

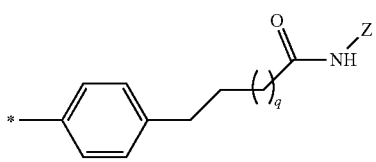

wherein: q is 0-12; and Z is the specific binding member.

Clause 57. The polymeric tandem dye according to any one of clauses 54-56, wherein Z is a biomolecule.

Clause 58. The polymeric tandem dye according to clause 57, wherein Z is an antibody.

Clause 59. The polymeric tandem dye according to clause 57, wherein Z is an antibody fragment or binding derivative thereof.

Clause 60. The polymeric tandem dye according to clause 59, wherein the antibody fragment or binding derivative thereof is selected from the group consisting of a Fab fragment, a F(ab')₂ fragment, a scFv, a diabody and a triabody.

Clause 61. The polymeric tandem dye according to any one of clauses 53-60, wherein the water solvated polymeric dye is a polymeric dye according to any one of clauses 2-42.

Clause 62. A labelled specific binding member, comprising:
a water solvated polymeric dye having a deep ultraviolet excitation spectrum and comprising a segment of π-conjugated co-monomers and a conjugation-modifying repeat unit; and
a specific binding member covalently linked to the polymeric dye.

Clause 63. The labelled specific binding member according to clause 62, wherein the conjugation-modifying repeat unit comprises the structure:

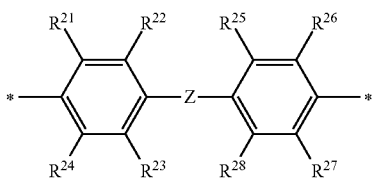

wherein:
Z is selected from a covalent bond, a saturated atom, a saturated group and a functional group, with the proviso that when Z is a covalent bond at least two of $R^{22}$, $R^{23}$, $R^{25}$ and $R^{28}$ are not H (e.g., at least one of $R^{22}$ and $R^{23}$, and at least one of $R^{25}$ and $R^{28}$ is not H);

$R^{21}$-$R^{28}$ are independently selected from H, alkyl, substituted alkyl, aryl, substituted aryl, heteroaryl, substituted heteroaryl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide, and a water solubilizing group, and wherein one or more of $R^{22}$, $R^{23}$, $R^{25}$ and $R^{28}$ is optionally cyclically linked to Z to provide a benzo-fused carbocycle or heterocycle ring; and
each * is a site for covalent attachment to the backbone of the polymeric dye.

Clause 64. The labelled specific binding member according to any one of clauses 62-63, wherein the polymeric dye comprises a signaling chromophore covalently linked to the polymeric dye in energy-receiving proximity therewith.

Clause 65. The labelled specific binding member according to any one of clauses 62-64, wherein the specific binding member is an antibody.

Clause 66. The labelled specific binding member according to any one of clauses 62-64, wherein the specific binding member is an antibody fragment or binding derivative thereof.

Clause 67. The labelled specific binding member according to clause 66, wherein the antibody fragment or binding derivative thereof is selected from the group consisting of a Fab fragment, a F(ab')₂ fragment, a scFv, a diabody and a triabody.

Clause 68. The labelled specific binding member according to clause 64, wherein the signaling chromophore is selected from a rhodamine, a coumarin, a xanthene, a cyanine, a polymethine, a pyrene, a dipyrromethene borondifluoride, a napthalimide, a phycobiliprotein, a peridinum chlorophyll protein, conjugates thereof, and combinations thereof.

Clause 69. The labelled specific binding member according to any one of clauses 62-68, wherein the water solvated polymeric dye is a polymeric dye according to any one of clauses 2-42.

Clause 70. A method of evaluating a sample for the presence of a target analyte, the method comprising:
(a) contacting the sample with a polymeric dye conjugate that specifically binds the target analyte to produce a labelling composition contacted sample, wherein the polymeric dye conjugate comprises:
(i) a polymeric dye having a deep ultraviolet excitation spectrum according to any one of clauses 1-42; and
(ii) a specific binding member covalently linked to the polymeric dye; and
(b) assaying the labelling composition contacted sample for the presence of a polymeric dye conjugate-target analyte binding complex to evaluate whether the target analyte is present in the sample.

Clause 71. The method according to clause 70, wherein the polymeric dye comprises a signaling chromophore covalently linked to the multichromophore in energy-receiving proximity therewith.

Clause 72. The method according to any one of clauses 70-71, further comprising contacting the sample with a second specific binding member that is support bound and specifically binds the target analyte.

Clause 73. The method according to clause 72, wherein the support comprises a magnetic particle.

Clause 74. The method according to any one of clauses 70-73, wherein the target analyte is associated with a cell.

Clause 75. The method according to clause 75, wherein the target analyte is a cell surface marker of the cell.

Clause 76. The method according to clause 75, wherein the cell surface marker is selected from the group consisting of a cell receptor and a cell surface antigen Clause 77. The method according to clause 74, wherein the target analyte is an intracellular target, and the method further comprises lysing the cell.

Clause 78. The method according to any one of clauses 70-77, wherein the method further comprises flow cytometrically analyzing the fluorescently labelled target analyte.

Clause 79. A method of labelling a target molecule, the method comprising:
contacting the target molecule with a water solvated polymeric dye to produce a labelled target molecule, wherein the water solvated polymeric dye has a deep ultraviolet excitation spectrum and comprises:
a segment of π-conjugated co-monomers;
a conjugation-modifying repeat unit; and
a conjugation tag that covalently links to the target molecule.

Clause 80. The method according to clause 79, wherein the conjugation-modifying repeat unit comprises the structure:

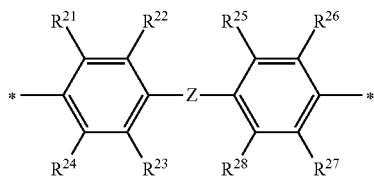

wherein:
Z is selected from a covalent bond, a saturated atom, a saturated group and a functional group, with the proviso that when Z is a covalent bond at least two of $R^{22}$, $R^{23}$, $R^{25}$ and $R^{28}$ are not H (e.g., at least one of $R^{22}$ and $R^{23}$, and at least one of $R^{25}$ and $R^{28}$ is not H);
$R^{21}$-$R^{28}$ are independently selected from H, alkyl, substituted alkyl, aryl, substituted aryl, heteroaryl, substituted heteroaryl, alkoxy, substituted alkoxy, hydroxy, cyano, halogen (e.g., fluoro, chloro or bromo), sulfonate, sulfonamide, substituted sulfonamide, carboxy, carboxyamide, substituted carboxyamide, and a water solubilizing group, and wherein one or more of $R^{22}$, $R^{23}$, $R^{25}$ and $R^{28}$ is optionally cyclically linked to Z to provide a benzo-fused carbocycle or heterocycle ring; and
each * is a site for covalent attachment to the backbone of the polymeric dye.

Clause 81. The method according to any one of clauses 79-80, wherein the polymeric dye comprises a signaling chromophore covalently linked to the polymeric dye in energy-receiving proximity therewith.

Clause 82. The method according to any one of clauses 79-81, further comprising fluorescently detecting the labelled target molecule.

Clause 83. The method according to any one of clauses 79-82, wherein the conjugation tag comprises a terminal functional group selected from an amino, a thiol, a hydroxyl, a hydrazine, a hydrazide, an azide, an alkyne, maleimide, iodoacetyl, amine, an active ester and a protein reactive group.

Clause 84. The method according to any one of clauses 79-83, wherein the target molecule is a specific binding member.

Clause 85. The method according to clause 84, wherein the specific binding member is an antibody.

Clause 86. The method according to clause 85, wherein the specific binding member is an antibody fragment or binding derivative thereof.

Clause 87. The method according to clause 86, wherein the antibody fragment or binding derivative thereof is selected from the group consisting of a Fab fragment, a $F(ab')_2$ fragment, a scFv, a diabody and a triabody.

Clause 88. A flow cytometric system, comprising:
a flow cytometer comprising a flow path;
a composition in the flow path, wherein the composition comprises:
a sample; and
a labelled specific binding member comprising:
a water solvated polymeric dye having a deep ultraviolet excitation spectrum according to any one of clauses 1-30; and
a specific binding member that specifically binds a target analyte and is covalently linked to the water solvated polymeric dye.

Clause 89. The system according to clause 88, wherein the labelled specific binding member further comprises a signaling chromophore covalently linked to the polymeric dye in energy-receiving proximity therewith.

Clause 90. The system according to any one of clauses 88-89, wherein the composition further comprises a second specific binding member that is support bound and specifically binds the target analyte.

Clause 91. The system according to clause 90, wherein the support comprises a magnetic particle.

Clause 92. The system according to any one of clauses 88-91, wherein the sample comprises a cell.

Clause 93. The system according to clause 92, wherein the target analyte is a cell surface marker of the cell.

Clause 94. The system according to clause 93, wherein the cell surface marker is selected from the group consisting of a cell receptor and a cell surface antigen.

Clause 95. A kit comprising: a polymeric dye having a deep ultraviolet excitation spectrum according to any one of clauses 1-42; and a container.

Clause 96. The kit according to clause 95, further comprising one or more components selected from the group consisting of a polymeric tandem dye, a fluorophore, a specific binding member, a specific binding member conjugate, a cell, a support, a biocompatible aqueous elution buffer and instructions for use.

Clause 97. The kit according to any one of clauses 95-96, wherein the polymeric dye is covalently linked to a specific binding member.

Clause 98. The kit according to clause 97, wherein the specific binding member is an antibody.

Clause 99. The kit according to clause 97, wherein the specific binding member is an antibody fragment or binding derivative thereof.

Clause 100. The kit according to clause 99, wherein the antibody fragment or binding derivative thereof is selected from the group consisting of a Fab fragment, a $F(ab')_2$ fragment, a scFv, a diabody and a triabody.

Clause 101. The kit according to any one of clauses 95-100, wherein polymeric dye further comprises an acceptor signaling chromophore covalently linked to the polymeric due in energy-receiving proximity therewith.

EXAMPLES

Example 1: Synthesis of Conjugated Polymer Via C—H Bond Arylation

The synthesis of the subject polymeric dyes can be achieved by a technique called C—H bond arylation (Scheme 1). Other methods such as a Suzuki coupling method (Scheme 2) or a Stille coupling method (Scheme 3) can also be utilized. The following exemplary synthetic schemes can be adapted for the synthesis of the subject polymeric dyes having a variety of co-monomers, as described herein.

Scheme 1: C—H Bond Arylation Method

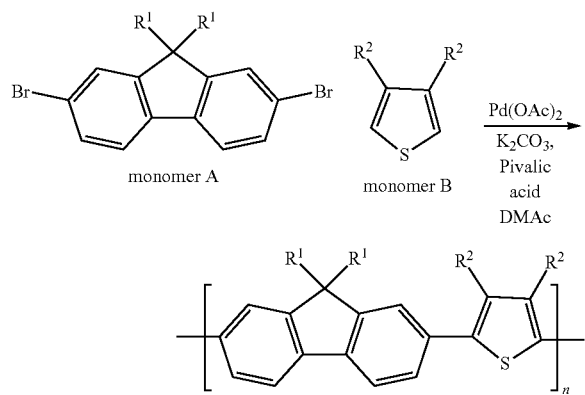

Scheme 2: Suzuki Coupling Method

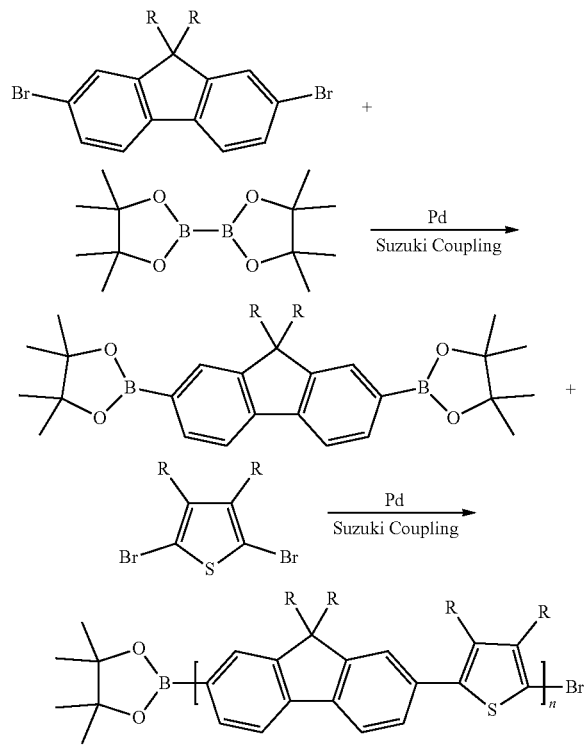

Scheme 3: Stille Coupling Method

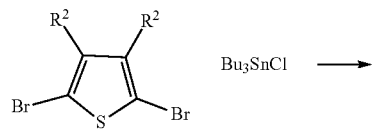

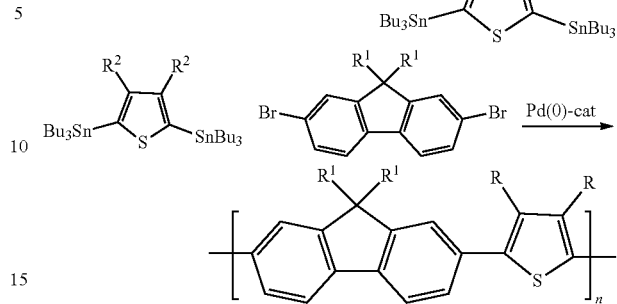

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of evaluating a sample for the presence of a target analyte, the method comprising:
    (a) contacting the sample with a polymeric dye conjugate that specifically binds the target analyte to produce a labelling composition contacted sample, wherein the polymeric dye conjugate comprises:
        (i) a polymeric dye having a deep ultraviolet excitation spectrum and comprising: a segment of π-conjugated co-monomers; and a conjugation-modifying repeat unit; and (ii) a specific binding member covalently linked to the polymeric dye; and (b) assaying the labelling composition contacted sample for the presence of a polymeric dye conjugate-target analyte binding complex to evaluate whether the target analyte is present in the sample, wherein the conjugation-modifying repeat unit comprises the structure:

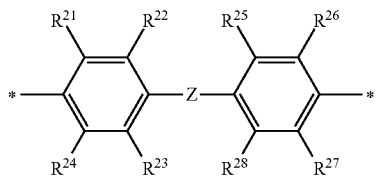

wherein:

Z is selected from a covalent bond, a saturated atom, a saturated group and a functional group, with the proviso that when Z is a covalent bond at least two of $R^{22}$, $R^{23}$, $R^{25}$ and $R^{28}$ are not H; $R^{21}$-$R^{28}$ are independently selected from H, alkyl, substituted alkyl, aryl, substituted aryl, heteroaryl, substituted heteroaryl, alkoxy, substituted alkoxy, hydroxy, cyano, halogen, sulfonate, sulfonamide, substituted sulfonamide, carboxy, carboxyamide, substituted carboxyamide, and a water solubilizing group, and wherein one or more of $R^{22}$, $R^{23}$, $R^{25}$ and $R^{28}$ is optionally cyclically linked to Z to provide a benzo-fused carbocycle or heterocycle ring; and each * is a site for covalent attachment to the backbone of the polymeric dye.

2. The method according to claim 1, wherein the polymeric dye comprises a signaling chromophore covalently linked to the multichromophore in energy-receiving proximity therewith.

3. The method according to claim 1, further comprising contacting the sample with a second specific binding member that is support bound and specifically binds the target analyte.

4. The method according to claim 3, wherein the support comprises a magnetic particle.

5. The method according to claim 1, wherein the target analyte is associated with a cell.

6. The method according to claim 5, wherein the target analyte is a cell surface marker of the cell.

7. The method according to claim 5, wherein the cell surface marker is selected from the group consisting of a cell receptor and a cell surface antigen.

8. The method according to claim 5, wherein the target analyte is an intracellular target, and the method further comprises lysing the cell.

9. The method according to claim 1, wherein the method further comprises flow cytometrically analyzing the fluorescently labelled target analyte.

10. A method of labelling a target molecule, the method comprising:

contacting the target molecule with a water solvated polymeric dye to produce a labelled target molecule, wherein the water solvated polymeric dye has a deep ultraviolet excitation spectrum and comprises:

a segment of π-conjugated co-monomers;

a conjugation-modifying repeat unit; and a conjugation tag that covalently links to the target molecule, wherein the conjugation-modifying repeat unit comprises the structure:

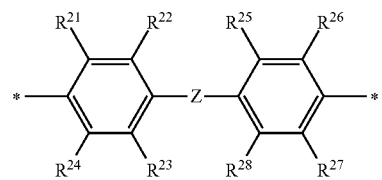

wherein:

Z is selected from a covalent bond, a saturated atom, a saturated group and a functional group, with the proviso that when Z is a covalent bond at least two of $R^{22}$, $R^{23}$, $R^{25}$ and $R^{28}$ are not H; $R^{21}$-$R^{28}$ are independently selected from H, alkyl, substituted alkyl, aryl, substituted aryl, heteroaryl, substituted heteroaryl, alkoxy, substituted alkoxy, hydroxy, cyano, halogen, sulfonate, sulfonamide, substituted sulfonamide, carboxy, carboxyamide, substituted carboxyamide, and a water solubilizing group, and wherein one or more of $R^{22}$, $R^{23}$, $R^{25}$ and $R^{28}$ is optionally cyclically linked to Z to provide a benzo-fused carbocycle or heterocycle ring; and each * is a site for covalent attachment to the backbone of the polymeric dye.

11. The method according to claim 10, wherein the polymeric dye comprises a signaling chromophore covalently linked to the polymeric dye in energy-receiving proximity therewith.

12. The method according to claim 10, further comprising fluorescently detecting the labelled target molecule.

13. The method according to claim 10, wherein the conjugation tag comprises a terminal functional group selected from an amino, a thiol, a hydroxyl, a hydrazine, a hydrazide, an azide, an alkyne, maleimide, iodoacetyl, amine, an active ester and a protein reactive group.

14. The method according to claim 10, wherein the target molecule is a specific binding member.

15. The method according to claim 14, wherein the specific binding member is an antibody.

16. The method according to claim 14, wherein the specific binding member is an antibody fragment or binding derivative thereof.

17. The method according to claim 16, wherein the antibody fragment or binding derivative thereof is selected from the group consisting of a Fab fragment, a $F(ab')_2$ fragment, a scFv, a diabody and a triabody.

18. A kit comprising:

(a) a polymeric dye having a deep ultraviolet excitation spectrum and comprising: a segment of π-conjugated co-monomers; and a conjugation-modifying repeat unit; and (b) a container, wherein the conjugation-modifying repeat unit comprises the structure:

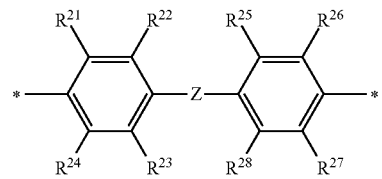

wherein:

Z is selected from a covalent bond, a saturated atom, a saturated group and a functional group, with the proviso that when Z is a covalent bond at least two of $R^{22}$, $R^{23}$, $R^{25}$ and $R^{28}$ are not H; $R^{21}$-$R^{28}$ are independently selected from H, alkyl, substituted alkyl, aryl, substituted aryl, heteroaryl, substituted heteroaryl, alkoxy, substituted alkoxy, hydroxy, cyano, halogen, sulfonate, sulfonamide, substituted sulfonamide, carboxy, carboxyamide, substituted carboxyamide, and a water solubilizing group, and wherein one or more of $R^{22}$, $R^{23}$, $R^{25}$ and $R^{28}$ is optionally cyclically linked to Z to provide a benzo-fused carbocycle or heterocycle ring; and each * is a site for covalent attachment to the backbone of the polymeric dye.

19. The kit according to claim 18, further comprising one or more components selected from the group consisting of a polymeric tandem dye, a fluorophore, a specific binding member, a specific binding member conjugate, a cell, a support, a biocompatible aqueous elution buffer and instructions for use.

\* \* \* \* \*